(12) United States Patent
Bentwich et al.

(10) Patent No.: US 7,795,419 B2
(45) Date of Patent: Sep. 14, 2010

(54) VIRAL AND VIRAL ASSOCIATED MIRNAS AND USES THEREOF

(75) Inventors: Itzhak Bentwich, Misgav (IL); Amir Avniel, Henderson, NV (US); Yael Karov, Tel Aviv (IL); Ranit Aharonov, Tel Aviv (IL)

(73) Assignee: Rosetta Genomics Ltd., Rehovot (IL)

( * ) Notice: Subject to any disclaimer, the term of this patent is extended or adjusted under 35 U.S.C. 154(b) by 0 days.

(21) Appl. No.: 11/511,035

(22) Filed: Aug. 28, 2006

(65) Prior Publication Data

US 2007/0003575 A1 Jan. 4, 2007

Related U.S. Application Data

(63) Continuation of application No. PCT/IB2005/002352, filed on May 26, 2005, which is a continuation-in-part of application No. 10/709,739, filed on May 26, 2004.

(60) Provisional application No. 60/522,459, filed on Oct. 4, 2004, provisional application No. 60/665,094, filed on Mar. 25, 2005, provisional application No. 60/522,450, filed on Oct. 3, 2004, provisional application No. 60/522,451, filed on Oct. 3, 2004.

(51) Int. Cl.
C07H 21/04 (2006.01)

(52) U.S. Cl. .................................. 536/24.5; 536/24.32

(58) Field of Classification Search ...................... None
See application file for complete search history.

(56) References Cited

U.S. PATENT DOCUMENTS

| | | | | |
|---|---|---|---|---|
| 6,001,806 | A * | 12/1999 | Hilbert et al. .................. 514/12 |
| 6,018,036 | A * | 1/2000 | Mosmann et al. ........... 536/23.5 |
| 6,451,977 | B1 * | 9/2002 | de Sauvage et al. .......... 530/350 |
| 6,458,943 | B1 * | 10/2002 | Byrne ........................ 536/23.5 |
| 6,573,099 | B2 | 6/2003 | Graham |
| 6,720,138 | B2 | 4/2004 | Sharma et al. |
| 6,753,139 | B1 | 6/2004 | Baulcombe et al. |
| 7,056,704 | B2 * | 6/2006 | Tuschl et al. ............... 435/91.1 |
| 2002/0086356 | A1 | 7/2002 | Tuschl et al. |
| 2003/0108923 | A1 | 6/2003 | Tuschl et al. |
| 2003/0204075 | A9 * | 10/2003 | Wang ........................ 536/24.3 |
| 2003/0228691 | A1 | 12/2003 | Lewis et al. |
| 2004/0053411 | A1 | 3/2004 | Cullen et al. |
| 2004/0086884 | A1 | 5/2004 | Beach et al. |
| 2004/0102412 | A1 * | 5/2004 | Broschat et al. ............... 514/44 |
| 2004/0106566 | A1 | 6/2004 | Lin et al. |
| 2004/0152112 | A1 | 8/2004 | Croce et al. |
| 2004/0171037 | A1 | 9/2004 | Li et al. |
| 2004/0175732 | A1 | 9/2004 | Rana |
| 2004/0210951 | A1 | 10/2004 | Baulcombe et al. |
| 2004/0221337 | A1 | 11/2004 | Baulcombe et al. |
| 2004/0229266 | A1 | 11/2004 | Tuschl et al. |
| 2004/0253604 | A1 | 12/2004 | Lin et al. |
| 2004/0259247 | A1 | 12/2004 | Tuschl et al. |
| 2004/0259248 | A1 | 12/2004 | Tuschl et al. |
| 2004/0268441 | A1 | 12/2004 | Vance et al. |
| 2005/0026278 | A1 | 2/2005 | Tuschl et al. |
| 2005/0037988 | A1 | 2/2005 | Zamore et al. |
| 2005/0059005 | A1 | 3/2005 | Tuschl et al. |
| 2005/0059011 | A1 | 3/2005 | Sin et al. |
| 2005/0074788 | A1 | 4/2005 | Dahlberg et al. |
| 2005/0075492 | A1 | 4/2005 | Chen et al. |
| 2005/0079614 | A1 | 4/2005 | Reinhart et al. |

FOREIGN PATENT DOCUMENTS

| | | |
|---|---|---|
| EP | 1 281 758 A2 * | 5/2003 |
| WO | WO 01/68836 | 9/2001 |
| WO | WO 02/44321 | 6/2002 |
| WO | WO 02/094185 | 11/2002 |
| WO | WO 01/75164 | 2/2003 |
| WO | WO 03/029459 | 4/2003 |
| WO | WO 03/070884 | 8/2003 |
| WO | WO 03/070903 | 8/2003 |
| WO | WO 03/070918 | 8/2003 |
| WO | WO 03/074654 | 9/2003 |
| WO | WO 2004/009779 | 1/2004 |
| WO | WO 2004/031412 | 4/2004 |
| WO | WO 2004/057017 | 7/2004 |
| WO | WO 2004/066183 | 8/2004 |
| WO | WO 2004/072248 | 8/2004 |
| WO | WO 2004/111191 | 12/2004 |
| WO | WO 2005/012523 | 2/2005 |
| WO | WO 2005/017111 | 2/2005 |
| WO | WO 2005/019453 | 3/2005 |

(Continued)

OTHER PUBLICATIONS

Krutzfeldt et al (2006) Nature Genetics 38:514-519.*
Parker et al (Virology 179: 339-346, 1990).*
Buck et al. (Biotechniques, 1999, 27:528-536).*
Edwards et al (J. Virol. 82(18): 9094-9106, 2008).*
MacDiarmid, R. RNA Silencing in Productive Virus Infections Annu Rev Phytopathol Apr. 12, 2004.
Chen, J., W. X. Li, D. Xie, J. R. Peng and S. W. Ding. Viral virulence protein suppresses RNA silencing-mediated defense but upregulates the role of microrna in host gene expression Plant Cell May (Epub Apr. 20, 2004) 2004 1302-1313 16.
Yekta, S., I. H. Shih and D. P. Bartel. MicroRNA-directed cleavage of HOXB8 mRNA Science Apr. 23, 2004 594-596 304.

(Continued)

*Primary Examiner*—Richard Schnizer
(74) *Attorney, Agent, or Firm*—Polsinelli Shughart PC; Teddy C. Scott, Jr.; Paul A. Jenny

(57) ABSTRACT

Described herein are novel polynucleotides associated with viral infections. The polynucleotides are miRNAs and miRNA precursors. Related methods and compositions that can be used for diagnosis, prognosis, and treatment of those medical conditions are disclosed. Also described herein are methods that can be used to identify modulators of viral infections.

2 Claims, 6 Drawing Sheets

FOREIGN PATENT DOCUMENTS

| WO | WO 2005/023986 | 3/2005 |
|----|----------------|--------|
| WO | WO 2005/033271 | 4/2005 |
| WO | WO 2005/035769 | 4/2005 |
| WO | WO 2005/041859 | 5/2005 |
| WO | WO 2005/042705 | 5/2005 |

OTHER PUBLICATIONS

Lamontagne, B., R. N. Hannoush, M. J. Damha and S. Abou Elela. Molecular requirements for duplex recognition and cleavage by eukaryotic RNase III: discovery of an RNA-dependent DNA cleavage activity of yeast Rnt1p J Mol Biol Apr. 23, 2004 401-418 338.

Barrick, J. E., K. A. Corbino, W. C. Winkler, A. Nahvi, M. Mandal, J. Collins, M. Lee, A. Roth, N. Sudarsan, I. Jona, J. K. Wickiser and R. R. Breaker. New RNA motifs suggest an expanded scope for riboswitches in bacterial genetic control Proc Natl Acad Sci U S A Apr. 27, 2004 6421-6426 101.

Pfeffer, S., M. Zavolan, F. A. Grasser, M. Chien, J. J. Russo, J. Ju, B. John, A. J. Enright, D. Marks, C. Sander and T. Tuschl. Identification of virus-encoded microRNAs Science Apr. 30, 2004 734-736 304.

Dorsett, Y. and T. Tuschl. siRNAs: applications in functional genomics and potential as therapeutics Nat Rev Drug Discov Apr. 2004 318-329 3.

Mallory, A. C. and H. Vaucheret. MicroRNAs: something important between the genes Curr Opin Plant Biol Apr. 2004 120-125 7.

Ogita, S., H. Uefuji, M. Morimoto and H. Sano. Application of RNAi to confirm theobromine as the major intermediate for caffeine biosynthesis in coffee plants with potential for construction of decaffeinated varieties Plant Mol Biol Apr. 2004 931-941 54.

Storz, G., J. A. Opdyke and A. Zhang. Controlling mRNA stability and translation with small, noncoding RNAs Curr Opin Microbiol Apr. 2004 140-144 7.

Kim, V. N. MicroRNA precursors in motion: exportin-5 mediates their nuclear export Trends Cell Biol Apr. 2004 156-159 14.

Jabri, E. RISCy business Nat Struct Mol Biol Apr. 2004 300 11.

Nakahara, K. and R. W. Carthew. Expanding roles for miRNAs and siRNAs in cell regulation Curr Opin Cell Biol Apr. 2004 127-133 16.

Ota, A., H. Tagawa, S. Karnan, S. Tsuzuki, A. Karpas, S. Kira, Y. Yoshida and M. Seto. Identification and characterization of a novel gene, C13orf25, as a target for 13q31-q32 amplification in malignant lymphoma Cancer Res May 1, 2004 3087-3095 64.

Marillonnet, S., A. Giritch, M. Gils, R. Kandzia, V. Klimyuk and Y. Gleba. In planta engineering of viral RNA replicons: efficient assembly by recombination of DNA modules delivered by Agrobacterium Proc Natl Acad Sci U S A May 4, 2004 6852-6857 101.

Kiriakidou, M., P. T. Nelson, A. Kouranov, P. Fitziev, C. Bouyioukos, Z. Mourelatos and A. Hatzigeorgiou. A combined computational-experimental approach predicts human microRNA targets Genes Dev May 15, 2004 1165-1178 18.

Vaucheret, H., F. Vazquez, P. Crete and D. P. Bartel. The action of ARGONAUTE1 in the miRNA pathway and its regulation by the miRNA pathway are crucial for plant development Genes Dev May 15, 2004 1187-1197 18.

Chapman, E. J., A. I. Prokhnevsky, K. Gopinath, V. V. Dolja and J. C. Carrington. Viral RNA silencing suppressors inhibit the microRNA pathway at an intermediate step Genes Dev May 15, 2004 1179-1186 18.

Bejerano, G., M. Pheasant, I. Makunin, S. Stephen, W. J. Kent, J. S. Mattick and D. Haussler. Ultraconserved elements in the human genome Science May 28, 2004 1321-1325 304.

Tanzer, A. and P. F. Stadler. Molecular evolution of a microRNA cluster J Mol Biol May 28, 2004 327-335 339.

Pooggin, M. and T. Hohn. Fighting geminiviruses by RNAi and vice versa Plant Mol Biol May 2004 149-152 55.

Bartel, D. P. and C. Z. Chen. Micromanagers of gene expression: the potentially widespread influence of metazoan microRNAs Nat Rev Genet May 2004 396-400 5.

Dunoyer, P., C. H. Lecellier, E. A. Parizotto, C. Himber and O. Voinnet. Probing the microRNA and small interfering RNA pathways with virus-encoded suppressors of RNA silencing Plant Cell May (Epub Apr. 14, 2004(2004 1235-1250 16.

Arias, C. F., M. A. Dector, L. Segovia, T. Lopez, M. Camacho, P. Isa, R. Espinosa and S. Lopez. RNA silencing of rotavirus gene expression Virus Res Jun. 1, 2004 43-51 102.

Takamizawa, J., H. Konishi, K. Yanagisawa, S. Tomida, H. Osada, H. Endoh, T. Harano, Y. Yatabe, M. Nagino, Y. Nimura, T. Mitsudomi and T. Takahashi. Reduced expression of the let-7 microRNAs in human lung cancers in association with shortened postoperative survival Cancer Res Jun. 1, 2004 3753-3756 64.

Ge, Q., L. Filip, a. Bai, T. Nguyen, H. N. Eisen and J. Chen. Inhibition of influenza virus production in virus-infected mice by RNA interference Proc Natl Acad Sci U S A Jun. 8, 2004 8676- 8681 101.

Suh, M. R., Y. Lee, J. Y. Kim, S. K. Kim, S. H. Moon, J. Y. Lee, K. Y. Cha, H. M. Chung, H. S. Yoon, S. Y. Moon, V. N. Kim and K. S. Kim. Human embryonic stem cells express a unique set of microRNAs Dev Biol Jun. 15, 2004 488-498 270.

Cole, K., V. Truong, D. Barone and G. Mcgall. Direct labeling of Rna with multiple biotins allows sensitive expression profiling of acute leukemia class predictor genes Nucleic Acids Res Jun. 17, 2004 e86 32.

Jones-Rhoades, M. W. and D. P. Bartel. Computational identification of plant microRNAs and their targets, including a stress-induced miRNA Mol Cell Jun.18, 2004 787-799 14.

Mallory, A. C., D. V. Dugas, D. P. Bartel and B. Bartel. MicroRNA regulation of NAC-domain targets is required for proper formation and separation of adjacent embryonic, vegetative, and floral organs Curr Biol Jun. 22, 2004 1035-1046 14.

Liu, C. G., G. A. Calin, B. Meloon, N. Gamliel, C. Sevignani, M. Ferracin, C. D. Dumitru, M. Shimizu, S. Zupo, M. Dono, H. Alder, F. Bullrich, M. Negrini and C. M. Croce. An oligonucleotide microchip for genome-wide microRNA profiling in human and mouse tissues Proc Natl Acad Sci U S A Jun. 29, 2004 9740-9744 101.

Brandenberger, R., H. Wei, S. Zhang, S. Lei, J. Murage, G. J. Fisk, Y. Li, C. Xu, R. Fang, K. Guegler, M. S. Rao, R. Mandalam, J. Lebkowski and L. W. Stanton. Transcriptome characterization elucidates signaling networks that control human ES cell growth and differentiation Nat Biotechnol Jun. 2004 707-716 22.

Engstrom, E. M., A. Izhaki and J. L. Bowman. Promoter bashing, microRNAs, and Knox genes. New insights, regulators, and targets-of-regulation in the establishment of lateral organ polarity in Arabidopsis Plant Physiol Jun. 2004 685-694 135.

Murchison, E. P. and G. J. Hannon. miRNAs on the move: miRNA biogenesis and the RNAi machinery Curr Opin Cell Biol Jun. 2004 223-229 16.

Novina, C. D. and P. A. Sharp. The RNAi revolution Nature Jul. 8, 2004 161-164 430.

Ji, Y., X. Xu and G. D. Stormo. A graph theoretical approach for predicting common RNA secondary structure motifs including pseudoknots in unaligned sequences Bioinformatics Jul. 10, 2004 1591-1602 20.

Okamura, K., A. Ishizuka, H. Siomi and M. C. Siomi. Distinct roles for Argonaute proteins in small RNA-directed RNA cleavage pathways Genes Dev Jul. 15, 2004 1655-1666 18.

Karlas, A., R. Kurth and J. Denner. Inhibition of porcine endogenous retroviruses by RNA interference: increasing the safety of xenotransplantation Virology Jul. 20, 2004 18-23 325.

Kent, O. A. and A. M. MacMillan. RNAi: running interference for the cell Org Biomol Chem Jul. 21, 2004 1957-1961 2.

Souret, F. F., J. P. Kastenmayer and P. J. Green. AtXRN4 degrades mRNA in Arabidopsis and its substrates include selected miRNA targets Mol Cell Jul. 23, 2004 173-183 15.

Meister, G., M. Landthaler, A. Patkaniowska, Y. Dorsett, G. Teng and T. Tuschl. Human Argonaute2 mediates RNA cleavage targeted by miRNAs and siRNAs Mol Cell Jul. 23, 2004 185-197 15.

Allawi, H. T., J. E. Dahlberg, S. Olson, E. Lund, M. Olson, W. P. Ma, T. Takova, B. P. Neri and V. I. Lyamichev. Quantitation of microRNAs using a modified Invader assay Rna Jul. 2004 1153-1161 10.

Hall, J. Opinion: Unravelling the general properties of siRNAs: strength in numbers and lessons from the past Nat Rev Genet Jul. 2004 552-557 5.

Silvestri, L. S., Z. F. Taraporewala and J. T. Patton. Rotavirus replication: plus-sense templates for double-stranded RNA synthesis are made in viroplasms J Virol Jul. 2004 7763-7774 78.

He, L. and G. J. Hannon. MicroRNAs: small RNAs with a big role in gene regulation Nat Rev Genet Jul. 2004 522-531 5.

Achard, P., A. Herr, D. C. Baulcombe and N. P. Harberd. Modulation of floral development by a gibberellin-regulated microRNA Development Jul. 2004 3357-3365 131.

McHale, N. A. and R. E. Koning. MicroRNA-directed cleavage of Nicotiana sylvestris Phavoluta mRNA regulates the vascular cambium and structure of apical meristems Plant Cell Jul (Epub Jun. 11, 2004) 2004 1730-1740 16.

Bonnet, E., J. Wuyts, P. Rouze and Y. Van De Peer. Detection of 91 potential conserved plant microRNAs in Arabidopsis thaliana and Oryza sativa identifies important target genes Proc Natl Acad Sci U S A Aug. 3, 2004 11511-11516 101.

Calin, G. A., C. G. Liu, C. Sevignani, M. Ferracin, N. Felli, C. D. Dumitru, M. Shimizu, A. Cimmino, S. Zupo, M. Dono, M. L. Dell'Aquila, H. Alder, L. Rassenti, T. J. Kipps, F. Bullrich, M. Negrini and C. M. Croce. MicroRNA profiling reveals distinct signatures in B cell chronic lymphocytic leukemias Proc Natl Acad Sci U S A Aug. 10, 2004 11755-11760 101.

Chang, S., R. J. Johnston, Jr., C. Frokjaer-Jensen, S. Lockery and O. Hobert. MicroRNAs act sequentially and asymmetrically to control chemosensory laterality in the nematode Nature Aug. 12, 2004 785-789 430.

Mallory, A. C., B. J. Reinhart, M. W. Jones-Rhoades, G. Tang, P. D. Zamore, M. K. Barton and D. P. Bartel. MicroRNA control of Phabulosa in leaf development: importance of pairing to the microRNA 5' region Embo J Aug. 18, 2004 3356-3364 23.

Kurihara, Y. and Y. Watanabe. Arabidopsis micro-RNA biogenesis through Dicer-like 1 protein functions Proc Natl Acad Sci U S A Aug. 24, 2004 12753-12758 101.

Famulok, M. Chemical biology: green fluorescent Rna Nature Aug. 26, 2004 976-977 430.

Morris, K. V., S. W. Chan, S. E. Jacobsen and D. J. Looney. Small interfering RNA-induced transcriptional gene silencing in human cells Science Aug. 27, 2004 1289-1292 305.

Miska, E. A., E. Alvarez-Saavedra, M. Townsend, A. Yoshii, N. Sestan, P. Rakic, M. Constantine-Paton and H. R. Horvitz. Microarray analysis of microRNA expression in the developing mammalian brain Genome Biol Epub Aug. 31, 2004 R68 5.

Wang, X. J., J. L. Reyes, N. H. Chua and T. Gaasterland. Prediction and identification of Arabidopsis thaliana microRNAs and their mRNA targets Genome Biol Epub Aug. 31, 2004 2004 R65 5.

Bagasra, O. and K. R. Prilliman. RNA interference: the molecular immune system J Mol Histol Aug. 2004 545-553 35.

He, Z. and E. J. Sontheimer. "siRNAs and miRNAs": a meeting report on RNA silencing Rna Aug. 2004 1165-1173 10.

Luciano, D. J., H. Mirsky, N. J. Vendetti and S. Maas. RNA editing of a miRNA precursor Rna Aug. 2004 1174-1177 10.

Levanon, E. Y., E. Eisenberg, R. Yelin, S. Nemzer, M. Hallegger, R. Shemesh, Z. Y. Fligelman, A. Shoshan, S. R. Pollock, D. Sztybel, M. Olshansky, G. Rechavi and M. F. Jantsch. Systematic identification of abundant A-to-I editing sites in the human transcriptome Nat Biotechnol Aug. 2004 1001-1005 22.

Friedrich, I., A. Shir, S. Klein and A. Levitzki. RNA molecules as anti-cancer agents Semin Cancer Biol Aug. 2004 223-230 14.

Mathews, D. H. Using an RNA secondary structure partition function to determine confidence in base pairs predicted by free energy minimization Rna Aug. 2004 1178-1190 10.

Aravin, A. A., M. S. Klenov, V. V. Vagin, F. Bantignies, G. Cavalli and V. A. Gvozdev. Dissection of a natural RNA silencing process in the Drosophila melanogaster germ line Mol Cell Biol Aug. 2004 6742-6750 24.

Sunkar, R. and J. K. Zhu. Novel and stress-regulated microRNAs and other small RNAs from Arabidopsis Plant Cell Aug (Epub Jul. 16, 2004) 2004 2001-2019 16.

Yoo, B. C., F. Kragler, E. Varkonyi-Gasic, V. Haywood, S. Archer-Evans, Y. M. Lee, T. J. Lough and W. J. Lucas. A systemic small RNA signaling system in plants Plant Cell Aug (Epub Jul. 16, 2004) 2004 1979-2000 16.

Gooch, B. D. and P. A. Beal. Recognition of duplex RNA by helix-threading peptides J Am Chem Soc Sep. 1, 2004 10603-10610 126.

Liu, J., M. A. Carmell, F. V. Rivas, C. G. Marsden, J. M. Thomson, J. J. Song, S. M. Hammond, L. Joshua-Tor and G. J. Hannon. Argonaute2 is the catalytic engine of mammalian RNAi Science Sep. 3, 2004 1437-1441 305.

Sontheimer, E. J. and R. W. Carthew. Molecular biology. Argonaute journeys into the heart of RISC Science Sep. 3, 2004 1409-1410 305.

Song, J. J., S. K. Smith, G. J. Hannon and L. Joshua-Tor. Crystal structure of Argonaute and its implications for RISC slicer activity Science Sep. 3, 2004 1434-1437 305.

Zeng, Y. and B. R. Cullen. Structural requirements for pre-microRNA binding and nuclear export by Exportin 5 Nucleic Acids Res Sep. 8, 2004 4776-4785 32.

Parizotto, E. A., P. Dunoyer, N. Rahm, C. Himber and O. Voinnet. In vivo investigation of the transcription, processing, endonucleolytic activity, and functional relevance of the spatial distribution of a plant miRNA Genes Dev Sep. 15, 2004 2237-2242 18.

Ambros, V. The functions of animal microRNAs Nature Sep. 16, 2004 350-355 431.

Baulcombe, D. RNA silencing in plants Nature Sep. 16, 2004 356-363 431.

Meister, G. and T. Tuschl. Mechanisms of gene silencing by double-stranded RNA Nature Sep. 16, 2004 343-349 431.

Kasashima, K., Y. Nakamura and T. Kozu. Altered expression profiles of microRNAs during TPA-induced differentiation of HL-60 cells Biochem Biophys Res Commun Sep. 17, 2004 403-410 322.

Smalheiser, N. R. and V. I. Torvik. A population-based statistical approach identifies parameters characteristic of human microRNA-mRNA interactions Bmc Bioinformatics Sep. 28, 2004 139 5.

Baba, S., M. Kajikawa, N. Okada and G. Kawai. Solution structure of an RNA stem-loop derived from the 3' conserved region of eel LINE UnaL2 Rna Sep. 2004 1380-1387 10.

Bowman, J. L. Class III HD-Zip gene regulation, the golden fleece of Argonaute activity? Bioessays Sep. 2004 938-942 26.

Ohler, U., S. Yekta, L. P. Lim, D. P. Bartel and C. B. Burge. Patterns of flanking sequence conservation and a characteristic upstream motif for microRNA gene identification Rna Sep. 2004 1309-1322 10.

Simmonds, P., A. Tuplin and D. J. Evans. Detection of genome-scale ordered RNA structure (GORS) in genomes of positive-stranded RNA viruses: Implications for virus evolution and host persistence Rna Sep. 2004 1337-1351 10.

Seitz, H., H. Royo, M. L. Bortolin, S. P. Lin, A. C. Ferguson-Smith and J. Cavaille. A large imprinted microRNA gene cluster at the mouse Dlk1-Gt12 domain Genome Res Sep. 2004 1741-1748 14.

Hobert, O. Common logic of transcription factor and microRNA action Trends Biochem Sci Sep. 2004 462-468 29.

Laufs, P., A. Peaucelle, H. Morin and J. Traas. MicroRNA regulation of the CUC genes is required for boundary size control in Arabidopsis meristems Development Sep. 2004 4311-4322 131.

Rye, P. D. and T. Stigbrand. Interfering with cancer: a brief outline of advances in RNA interference in oncology Tumour Biol Sep.-Dec. 2004 329-336 25.

Sigova, A., N. Rhind and P. D. Zamore. A single Argonaute protein mediates both transcriptional and posttranscriptional silencing in Schizosaccharomyces pombe Genes Dev Oct. 1, 2004 2359-2367 18.

Lee, Y., M. Kim, J. Han, K. H. Yeom, S. Lee, S. H. Baek and V. N. Kim. MicroRNA genes are transcribed by RNA polymerase II Embo J Oct. 13, 2004 4051-4060 23.

Nelson, P. T., D. A. Baldwin, L. M. Scearce, J. C. Oberholtzer, J. W. Tobias and Z. Mourelatos. Microarray-based, high-throughput gene expression profiling of microRNAs Nat Methods Oct 21 2004 155-161 1.

Kadotani, N., H. Nakayashiki, Y. Tosa and S. Mayama. One of the two Dicer-like proteins in the filamentous fungi Magnaporthe oryzae genome is responsible for hairpin RNA-triggered RNA silencing and related small interfering RNA accumulation J Biol Chem Oct. 22, 2004 44467-44474 279.

Duensing, S., A. Duensing, D. C. Lee, K. M. Edwards, S. O. Piboonniyom, E. Manuel, L. Skaltsounis, L. Meijer and K. Munger. Cyclin-dependent kinase inhibitor indirubin-3'-oxime selectively inhibits human papillomavirus type 16 E7-induced numerical centrosome anomalies Oncogene Oct. 28, 2004 8206-8215 23.

Antonarakis, S. E., R. Lyle, E. T. Dermitzakis, A. Reymond and S. Deutsch. Chromosome 21 and down syndrome: from genomics to pathophysiology Nat Rev Genet Oct. 2004 725-738 5.

Altuvia, S. Regulatory small RNAs: the key to coordinating global regulatory circuits J Bacteriol Oct. 2004 6679-6680 186.

Bracht, J., S. Hunter, R. Eachus, P. Weeks and A. E. Pasquinelli. Trans-splicing and polyadenylation of let-7 microRNA primary transcripts Rna Oct. 2004 1586-1594 10.

Cobb, J. and D. Duboule. Tracing microRNA patterns in mice Nat Genet Oct. 2004 1033-1034 36.

Duxbury, M. S., E. Matros, H. Ito, M. J. Zinner, S. W. Ashley and E. E. Whang. Systemic siRNA-mediated gene silencing: a new approach to targeted therapy of cancer Ann Surg Oct. 2004 667-674; discussion 675-666 240.

Dugas, D. V. and B. Bartel. MicroRNA regulation of gene expression in plants Curr Opin Plant Biol Oct. 2004 512-520 7.

Howard, M. T., R. F. Gesteland and J. F. Atkins. Efficient stimulation of site-specific ribosome frameshifting by antisense oligonucleotides Rna Oct. 2004 1653-1661 10.

Isken, O., C. W. Grassmann, H. Yu and S. E. Behrens. Complex signals in the genomic 3' nontranslated region of bovine viral diarrhea virus coordinate translation and replication of the viral RNA Rna Oct. 2004 1637-1652 10.

Mansfield, J. H., B. D. Harfe, R. Nissen, J. Obenauer, J. Srineel, A. Chaudhuri, R. Farzan-Kashani, M. Zuker, A. E. Pasquinelli, G. Ruvkun, P. A. Sharp, C. J. Tabin and M. T. McManus. MicroRNA-responsive 'sensor' transgenes uncover Hox-like and other developmentally regulated patterns of vertebrate microRNA expression Nat Genet Oct. 2004 1079-1083 36.

Opdyke, J. A., J. G. Kang and G. Storz. GadY, a small-Rna regulator of acid response genes in Escherichia coli J Bacteriol Oct. 2004 6698-6705 186.

Rehmsmeier, M., P. Steffen, M. Hochsmann and R. Giegerich. Fast and effective prediction of microRNA/target duplexes Rna Oct. 2004 1507-1517 10.

Rodriguez, A., S. Griffiths-Jones, J. L. Ashurst and A. Bradley. Identification of mammalian microRNA host genes and transcription units Genome Res Oct. 2004 1902-1910 14.

Pillai, R. S., C. G. Artus and W. Filipowicz. Tethering of human Ago proteins to mRNA mimics the miRNA-mediated repression of protein synthesis Rna Oct. 2004 1518-1525 10.

Stix, G. Hitting the genetic off switch Sci Am Oct. 2004 98-101 291.

Chen, S., A. Zhang, L. B. Blyn and G. Storz. MicC, a second small-RNA regulator of Omp protein expression in Escherichia coli J Bacterial Oct. 2004 6689-6697 186.

Gebauer, F. and M. W. Hentze. Molecular mechanisms of translational control Nat Rev Mol Cell Biol Oct. 2004 827-835 5.

Jones, S. W., P. M. Souza and M. A. Lindsay. siRNA for gene silencing: a route to drug target discovery Curr Opin Pharmacol Oct. 2004 522-527 4.

Mattick, J. S. The hidden genetic program of complex organisms Sci Am Oct. 2004 60-67 291.

Trainor, P. A. Developmental biology is "Cruzing" Dev Cell Oct. 2004 481-486 7.

Arai, R., K. Ito, M. Wakiyama, E. Matsumoto, A. Sakamoto, Y. Etou, M. Otsuki, M. Inoue, Y. Hayashizaki, M. Miyagishi, K. Taira, M. Shirouzu and S. Yokoyama. Establishment of stable hFis1 knockdown cells with an siRNA expression vector J Biochem (Tokyo) Oct. 2004 421-425 136.

Thomson, J. M., J. Parker, C. M. Perou and S. M. Hammond. A custom microarray platform for analysis of microRNA gene expression Nat Methods Oct (Epub Sep. 29, 2004) 2004 47-53 1.

Krol, J., K. Sobczak, U. Wilczynska, M. Drath, A. Jasinska, D. Kaczynska and W. J. Krzyzosiak. Structural features of microRNA (miRNA) precursors and their relevance to miRNA biogenesis and small interfering RNA/short hairpin RNA design J Biol Chem Oct. 1 (Epub Aug. 2, 2004) 2004 42230-42239 279.

Shen, B. and H. M. Goodman. Uridine addition after microRNA-directed cleavage Science Nov. 5, 2004 997 306.

Davidson, T. J., S. Harel, V. A. Arboleda, G. F. Prunell, M. L. Shelanski, L. A. Greene and C. M. Troy. Highly efficient small interfering RNA delivery to primary mammalian neurons induces MicroRNA-like effects before mRNA degradation J Neurosci Nov. 10, 2004 10040-10046 24.

Ying, S. Y. and S. L. Lin. Intron-derived microRNAs—fine tuning of gene functions Gene Nov. 10, 2004 25-28 342.

Denli, A. M., B. B. Tops, R. H. Plasterk, R. F. Ketting and G. J. Hannon. Processing of primary microRNAs by the Microprocessor complex Nature Nov. 11, 2004 231-235 432.

Gregory, R. I., K. P. Yan, G. Amuthan, T. Chendrimada, B. Doratotaj, N. Cooch and R. Shiekhattar. The Microprocessor complex mediates the genesis of microRNAs Nature Nov. 11, 2004 235-240 432.

Poy, M. N., L. Eliasson, J. Krutzfeldt, S. Kuwajima, X. Ma, P. E. Macdonald, S. Pfeffer, T. Tuschl, N. Rajewsky, P. Rorsman and M. Stoffel. A pancreatic islet-specific microRNA regulates insulin secretion Nature Nov. 11, 2004 226-230 432.

Soutschek, J., A. Akinc, B. Bramlage, K. Charisse, R. Constien, M. Donoghue, S. Elbashir, A. Geick, P. Hadwiger, J. Harborth, M. John, V. Kesavan, G. Lavine, R. K. Pandey, T. Racie, K. G. Rajeev, I. Rohl, I. Toudjarska, G. Wang, S. Wuschko, D. Bumcrot, V. Koteliansky, S. Limmer, M. Manoharan and H. P. Vornlocher. Therapeutic silencing of an endogenous gene by systemic administration of modified siRNAs Nature Nov. 11, 2004 173-178 432.

Couzin, J. Molecular biology. RNAi shows cracks in its armor Science Nov. 12, 2004 1124-1125 306.

Rao, M. Conserved and divergent paths that regulate self-renewal in mouse and human embryonic stem cells Dev Biol Nov. 15, 2004 269-286 275.

Tomari, Y., C. Matranga, B. Haley, N. Martinez and P. D. Zamore. A protein sensor for siRNA asymmetry Science Nov. 19, 2004 1377-1380 306.

Belostotsky, D. mRNA turnover meets RNA interference Mol Cell Nov. 19, 2004 498-500 16.

Bonnet, E., J. Wuyts, P. Rouze and Y. Van De Peer. Evidence that microRNA precursors, unlike other non-coding RNAs, have lower folding free energies than random sequences Bioinformatics Nov. 22, 2004 2911-2917 20.

Koziczak, M. and N. E. Hynes. Cooperation between fibroblast growth factor receptor-4 and ErbB2 in regulation of cyclin D1 translation J Biol Chem Nov. 26 (Epub Sep. 17, 2004) 2004 50004-50011 279.

Esquela-Kerscher, A. and F. J. Slack. The age of high-throughput microRNA profiling Nat Methods Nov. 2004 106-107 1.

Jackson, A. L. and P. S. Linsley. Noise amidst the silence: off-target effects of siRNAs? Trends Genet Nov. 2004 521-524 20.

Huang, M., Y. Wang, M. Collins and L. M. Graves. CPEC induces erythroid differentiation of human myeloid leukemia K562 cells through CTP depletion and p38 MAP kinase Leukemia Nov. 2004 1857-1863 18.

Lovett-Racke, A. E., A. E. Rocchini, J. Choy, S. C. Northrop, R. Z. Hussain, R. B. Ratts, D. Sikder and M. K. Racke. Silencing T-bet defines a critical role in the differentiation of autoreactive T lymphocytes Immunity Nov. 2004 719-731 21.

Jin, P., R. S. Alisch and S. T. Warren. RNA and microRNAs in fragile X mental retardation Nat Cell Biol Nov. 2004 1048-1053 6.

John, B., A. J. Enright, A. Aravin, T. Tuschl, C. Sander and D. S. Marks. Human MicroRNA targets PLoS Biol Nov. 2004 e363 2.

Bao, N., K. W. Lye and M. K. Barton. MicroRNA binding sites in Arabidopsis class III HD-ZIP MRNAs are required for methylation of the template chromosome Dev Cell Nov. 2004 653-662 7.

Eshed, Y. and J. L. Bowman. MicroRNAs guide asymmetric DNA modifications guiding asymmetric organs Dev Cell Nov. 2004 629-630 7.

Babak, T., W. Zhang, Q. Morris, B. J. Blencowe and T. R. Hughes. Probing microRNAs with microarrays: tissue specificity and functional inference Rna Nov. 2004 1813-1819 10.

Chattopadhyay, S., Y. Wang, R. Zhao and I. D. Goldman. Lack of impact of the loss of constitutive folate receptor alpha expression, achieved by RNA Interference, on the activity of the new generation antifolate pemetrexed in HeLa cells Clin Cancer Res Dec. 1, 2004 7986-7993 10.

O'Loghlen, A., V. M. Gonzalez, M. Salinas and M. E. Martin. Suppression of human Mnk1 by small interfering RNA increases the eukaryotic initiation factor 4F activity in HEK293T cells FEBS Lett Dec. 3, 2004 31-35 578.

Esau, C., X. Kang, E. Peralta, E. Hanson, E. G. Marcusson, L. V. Ravichandran, Y. Sun, S. Koo, R. J. Perera, R. Jain, N. M. Dean, S. M. Freier, C. F. Bennett, B. Lollo and R. Griffey. MicroRNA-143 regulates adipocyte differentiation J Biol Chem Dec. 10, 2004 52361-52365 279.

Valoczi, A., C. Hornyik, N. Varga, J. Burgyan, S. Kauppinen and Z. Havelda. Sensitive and specific detection of microRNAs by northern blot analysis using LNA-modified oligonucleotide probes Nucleic Acids Res Dec. 14, 2004 e175 32.

Landthaler, M., A. Yalcin and T. Tuschl. The human DiGeorge syndrome critical region gene 8 and Its D. melanogaster homolog are required for miRNA biogenesis Curr Biol Dec. 14, 2004 2162-2167 14.

Bennasser, Y., S. Y. Le, M. L. Yeung and K. T. Jeang. HIV-1 encoded candidate micro-RNAs and their cellular targets Retrovirology Dec. 15, 2004 43 1.

Han, J., Y. Lee, K. H. Yeom, Y. K. Kim, H. Jin and V. N. Kim. The Drosha-DGCR8 complex in primary microRNA processing Genes Dev Dec. 15, 2004 3016-3027 18.

Omoto, S., M. Ito, Y. Tsutsumi, Y. Ichikawa, H. Okuyama, E. A. Brisibe, N. K. Saksena and Y. R. Fujii. HIV-1 nef suppression by virally encoded microRNA Retrovirology Dec. 15, 2004 44 1.

Jin, W. and G. J. Cote. Enhancer-dependent splicing of FGFR1 alpha-exon is repressed by RNA interference-mediated down-regulation of SRp55 Cancer Res Dec. 15, 2004 8901-8905 64.

Cullen, B. R. Transcription and processing of human microRNA precursors Mol Cell Dec. 22, 2004 861-865 16.

Sun, Y., S. Koo, N. White, E. Peralta, C. Esau, N. M. Dean and R. J. Perera. Development of a micro-array to detect human and mouse microRNAs and characterization of expression in human organs Nucleic Acids Res Dec. 22, 2004 e188 32.

Kittler, R., G. Putz, L. Pelletier, I. Poser, A. K. Heninger, D. Drechsel, S. Fischer, I. Konstantinova, B. Habermann, H. Grabner, M. L. Yaspo, H. Himmelbauer, B. Korn, K. Neugebauer, M. T. Pisabarro and F. Buchholz. An endoribonuclease-prepared siRNA screen in human cells identifies genes essential for cell division Nature Dec. 23, 2004 1036-1040 432.

Bignold, L. P. The cell-type-specificity of inherited predispositions to tumours: review and hypothesis Cancer Lett Dec. 28, 2004 127-146 216.

Rapozzi, V. and L. E. Xodo. Efficient silencing of bcr/abl oncogene by single- and double-stranded siRNAs targeted against b2a2 transcripts Biochemistry Dec. 28, 2004 16134-16141 43.

Kanatsu-Shinohara, M., K. Inoue, J. Lee, M. Yoshimoto, N. Ogonuki, H. Miki, S. Baba, T. Kato, Y. Kazuki, S. Toyokuni, M. Toyoshima, O. Niwa, M. Oshimura, T. Heike, T. Nakahata, F. Ishino, A. Ogura and T. Shinohara. Generation of pluripotent stem cells from neonatal mouse testis Cell Dec. 29, 2004 1001-1012 119.

Agrawal, S. and E. R. Kandimalla. Role of Toll-like receptors in antisense and siRNA [corrected] Nat Biotechnol Dec. 2004 1533-1537 22.

Bantounas, I., L. A. Phylactou and J. B. Uney. RNA interference and the use of small interfering RNA to study gene function in mammalian systems J Mol Endocrinol Dec. 2004 545-557 33.

Barad, O., E. Meiri, A. Avniel, R. Aharonov, A. Barzilai, I. Bentwich, U. Einav, S. Gilad, P. Hurban, Y. Karov, E. K. Lobenhofer, E. Sharon, Y. M. Shiboleth, M. Shtutman, Z. Bentwich and P. Einat. MicroRNA expression detected by oligonucleotide microarrays: system establishment and expression profiling in human tissues Genome Res Dec. 2004 2486-2494 14.

Komano, J., K. Miyauchi, Z. Matsuda and N. Yamamoto. Inhibiting the Arp2/3 complex limits infection of both intracellular mature vaccinia virus and primate lentiviruses Mol Biol Cell Dec. 2004 5197-5207 15.

Lu, S. and B. R. Cullen. Adenovirus VA1 noncoding RNA can inhibit small interfering RNA and MicroRNA biogenesis AJ Virol Dec. 2004 12868-12876 78.

Ostberg, Y., I. Bunikis, S. Bergstrom and J. Johansson. The etiological agent of Lyme disease, Borrelia burgdorferi, appears to contain only a few small RNA molecules J Bacteriol Dec. 2004 8472-8477 186.

Shi, H., N. Chamond, C. Tschudi and E. Ullu. Selection and characterization of RNA interference-deficient trypanosomes impaired in target mRNA degradation Eukaryot Cell Dec. 2004 1445-1453 3.

Tan, F. L. And J. Q. Yin. RNAi, a new therapeutic strategy against viral infection Cell Res Dec. 2004 460-466 14.

Vella, M. C., K. Reinert and F. J. Slack. Architecture of a validated microRNA:target interaction Chem Biol Dec. 2004 1619-1623 11.

Allen, E., Z. Xie, A. M. Gustafson, G. H. Sung, J. W. Spatafora and J. C. Carrington. Evolution of microRNA genes by inverted duplication of target gene sequences in Arabidopsis thaliana Nat Genet Dec. 2004 1282-1290 36.

Xu, P., M. Guo and B. A. Hay. MicroRNAs and the regulation of cell death Trends Genet Dec. 2004 617-624 20.

Cai, X., C. H. Hagedorn and B. R. Cullen. Human microRNAs are processed from capped, polyadenylated transcripts that can also function as mRNAs Rna Dec (Epub Nov. 3, 2004) 2004 1957-1966 10.

Chang, J., E. Nicolas, D. Marks, C. Sander, A. Lerro, M. Annick Buendia, C. Xu, W. S. Mason, T. Moloshok, R. Bort, K. S. Zaret and J. M. Taylor. miR-122, a Mammalian Liver-Specific microRNA, is Processed from her mRNA and May Downregulate the High Affinity Cationic Amino Acid Transporter CAT-1 2004 106 1.

Gershon, D. Microarrays go mainstream Nature Methods 2004 263 1.

Joseph, R., A. Krichevsky, K. S. Kosik and R. Manchanda. Validation of miRNA microarray data using Micromax ASAP miRNA chemical labeling kit by Northern blot analysis PerkinElmer Life and Analytical Sciences 2004 1 6938.

Lund, E., S. Guttinger, A. Calado, J. E. Dahlberg and U. Kutay. Nuclear export of microRNA precursors Science Jan. 2 (Epub Nov. 20, 2003) 2004 95-98 303.

Matzke, M., W. Aufsatz, T. Kanno, L. Daxinger, I. Papp, M. F. Mette and A. J. Matzke. Genetic analysis of RNA-mediated transcriptional gene silencing 2004 129 1677.

Paradigmgenetics, I. Market Exploration: MicroRNAs Final Report 2004 1.

Soreq, H. and S. Seidman. Antisense approach to isoform specific blockade of acetylcholinesterase 2004 1.

Wang, L. C., O. C. Yen and E. Zandi. TNFa-dependent drug resistance to purine and pyrimidine analogues in human colon tumor cells mediated through IKK J.Biol Chem. 2004.

Hardy, J. Toward Alzheimer therapies based on genetic knowledge Annu Rev Med 2004 15-25 55.

Shabalina, S. A. and N. A. Spiridonov. The mammalian transcriptome and the function of non-coding DNA sequences Genome Biol 2004 105 5.

Gustafson, A. M., E. Allen, S. Givan, D. Smith, J. C. Carrington and K. D. Kasschau. ASRP: the Arabidopsis Small RNA Project Database Nucleic Acids Res Jan. 1, 2005 D637-640 33.

Pang, K. C., S. Stephen, P. G. Engstrom, K. Tajul-Arifin, W. Chen, C. Wahlestedt, B. Lenhard, Y. Hayashizaki and J. S. Mattick. RNAdb—a comprehensive mammalian noncoding RNA database Nucleic Acids Res Jan. 1, 2005 D125-130 33.

Einav, Y., R. Agami and D. Canaani. shRNA-mediated RNA interference as a tool for genetic synthetic lethality screening in mouse embryo fibroblasts FEBS Lett Jan. 3, 2005 199-202 579.

Sugiyama, T., H. Cam, A. Verdel, D. Moazed and S. I. Grewal. RNA-dependent RNA polymerase is an essential component of a self-enforcing loop coupling heterochromatin assembly to siRNA production Proc Natl Acad Sci U S A Jan. 4, 2005 152-157 102.

Huppi, K., S. E. Martin and N. J. Caplen. Defining and assaying RNAi in mammalian cells Mol Cell Jan. 7, 2005 1-10 17.

Zeng, Y., R. Yi and B. R. Cullen. Recognition and cleavage of primary microRNA precursors by the nuclear processing enzyme Drosha Embo J Jan. 12, 2005 138-148 24.

Tops, B. B., H. Tabara, T. Sijen, F. Simmer, C. C. Mello, R. H. Plasterk and R. F. Ketting. RDE-2 interacts with MUT-7 to mediate RNA interference in Caenorhabditis elegans Nucleic Acids Res Jan. 13, 2005 347-355 33.

Elmen, J., H. Thonberg, K. Ljungberg, M. Frieden, M. Westergaard, Y. Xu, B. Wahren, Z. Liang, H. Orum, T. Koch and C. Wahlestedt. Locked nucleic acid (LNA) mediated improvements in siRNA stability and functionality Nucleic Acids Res Jan. 14, 2005 439-447 33.

Lewis, B. P., C. B. Burge and D. P. Bartel. Conserved seed pairing, often flanked by adenosines, indicates that thousands of human genes are microRNA targets Cell Jan. 14, 2005 15-20 120.

Berezikov, E., V. Guryev, J. Van De Belt, E. Wienholds, R. H. Plasterk and E. Cuppen. Phylogenetic shadowing and computational identification of human microRNA genes Cell Jan. 14, 2005 21-24 120.

Tanzer, A., C. T. Amemiya, C. B. Kim and P. F. Stadler. Evolution of microRNAs located within Hox gene clusters J Exp Zoolog B Mol Dev Evol Jan. 15, 2005 75-85 304.

Yun, M. S., S. E. Kim, S. H. Jeon, J. S. Lee and K. Y. Choi. Both ERK and Wnt/beta-catenin pathways are involved in Wnt3a-induced proliferation J Cell Sci Jan. 15, 2005 313-322 118.

Watanabe, T., A. Takeda, K. Mise, T. Okuno, T. Suzuki, N. Minami and H. Imai. Stage-specific expression of microRNAs during Xenopus development FEBS Lett Jan. 17, 2005 318-324 579.

Ying, S. Y. and S. L. Lin. Intronic microRNAs Biochem Biophys Res Commun Jan. 21, 2005 515- 520 326.

Tomari, Y. and P. D. Zamore. MicroRNA biogenesis: drosha can't cut it without a partner Curr Biol Jan. 26, 2005 R61-64 15.

Fan, Q. W. and W. A. Weiss. RNA interference against a glioma-derived allele of EGFR induces blockade at G2M Oncogene Jan. 27, 2005 829-837 24.

Liang, R. Q., W. Li, Y. Li, C. Y. Tan, J. X. Li, Y. X. Jin and K. C. Ruan. An oligonucleotide microarray for microRNA expression analysis based on labeling RNA with quantum dot and nanogold probe Nucleic Acids Res Jan. 31, 2005 e17 33.

Akaneya, Y., B. Jiang and T. Tsumoto. RNAi-induced gene silencing by local electroporation in targeting brain region J Neurophysiol Jan. 2005 594-602 93.

Adai, A., C. Johnson, S. Mlotshwa, S. Archer-Evans, V. Manocha, V. Vance and V. Sundaresan. Computational prediction of miRNAs in Arabidopsis thaliana Genome Res Jan. 2005 78-91 15.

Alibu, V. P., L. Storm, S. Haile, C. Clayton and D. Horn. A doubly inducible system for RNA interference and rapid RNAi plasmid construction in Trypanosoma brucei Mol Biochem Parasitol Jan. 2005 75-82 139.

Alsford, S., L. Glover and D. Horn. Multiplex analysis of RNA interference defects in Trypanosoma brucei Mol Biochem Parasitol Jan. 2005 129-132 139.

Bedell, J. A., M. A. Budiman, A. Nunberg, R. W. Citek, D. Robbins, J. Jones, E. Flick, T. Rholfing, J. Fries, K. Bradford, J. McMenamy, M. Smith, H. Holeman, B. A. Roe, G. Wiley, I. F. Korf, P. D. Rabinowicz, N. Lakey, W. R. McCombie, J. A. Jeddeloh and R. A. Martienssen. Sorghum genome sequencing by methylation filtration PLoS Biol Jan. 2005 e13 3.

Hansen, K. R., G. Burns, J. Mata, T. A. Volpe, R. A. Martienssen, J. Bahler and G. Thon. Global effects on gene expression in fission yeast by silencing and RNA interference machineries Mol Cell Biol Jan. 2005 590-601 25.

Soldan, S. S., M. L. Plassmeyer, M. K. Matukonis and F. Gonzalez-Scarano. La Crosse virus nonstructural protein NSs counteracts the effects of short interfering RNA J Virol Jan. 2005 234-244 79.

Taylor, J. A. and N. V. Naoumov. The potential of RNA interference as a tool in the management of viral hepatitis J Hepatol Jan. 2005 139-144 42.

Wu, C. J., H. W. Huang, C. Y. Liu, C. F. Hong and Y. L. Chan. Inhibition of SARS-CoV replication by siRNA Antiviral Res Jan. 2005 45-48 65.

Weber, M. J. New human and mouse microRNA genes found by homology search Febs J Jan. 2005 59-73 272.

Zhang, Y. Q. and K. Broadie. Fathoming fragile X in fruit flies Trends Genet Jan. 2005 37-45 21.

Gitlin, L., J. K. Stone and R. Andino. Poliovirus escape from RNA interference: short interfering RNA-target recognition and implications for therapeutic approaches J Virol Jan. 2005 1027-1035 79.

Kan, L. and J. A. Kessler. New tool for an old problem: can RNAi efficiently resolve the issue of genetic redundancy? Bioessays Jan. 2005 14-16 27.

Pfeffer, S., A. Sewer, M. Lagos-Quintana, R. Sheridan, C. Sander, F. A. Grasser, L. F. Van Dyk, C. K. Ho, S. Shuman, M. Chien, J. J. Russo, J. Ju, G. Randall, B. D. Lindenbach, C. M. Rice, V. Simon, D. D. Ho, M. Zavolan and T. Tuschl. Identification of microRNAs of the herpesvirus family Nat Methods Feb. 16, 2005 269-276 2.

Saito, Y. and S. Dzik. Gene knockdown: RNA-interference is coming of age Transfusion Jan. 2005 111-114 45.

Scherr, M., K. Battmer, B. Schultheis, A. Ganser and M. Eder. Stable RNA interference (RNAi) as an option for anti-bcr-abl therapy Gene Ther Jan. 2005 12-21 12.

Article Weber, W., L. Malphettes, M. Rinderknecht, R. G. Schoenmakers, M. Spielmann, B. Keller, P. Van De Wetering, C. C. Weber and M. Fussenegger. Quorum-sensing-based toolbox for regulatable transgene and siRNA expression in mammalian cells Biotechnol Prog Jan.-Feb. 2005 178-185 21.

Zhang, W., H. Yang, X. Kong, S. Mohapatra, H. San Juan-Vergara, G. Hellermann, S. Behera, R. Singam, R. F. Lockey and S. S. Mohapatra. Inhibition of respiratory syncytial virus infection with intranasal siRNA nanoparticles targeting the viral NS1 gene Nat Med Jan. 2005 56-62 11.

Bitko, V., A. Musiyenko, O. Shulyayeva and S. Barik. Inhibition of respiratory viruses by nasally administered siRNA Nat Med Jan; Epub Dec. 26, 2004 50-55 11.

Article Weber, W., L. Malphettes, M. Rinderknecht, R. G. Schoenmakers, M. Spielmann, B. Keller, P. Van De Wetering, C. C. Weber and M. Fussenegger. Quorumsensing-based toolbox for regulatable transgene and siRNA expression in mammalian cells Biotechnol Prog Jan.-Feb. 2005 178-185 21.

Dresios, J., A. Aschrafi, G. C. Owens, P. W. Vanderklish, G. M. Edelman and V. P. Mauro. Cold stress-induced protein Rbm3 binds 60S ribosomal subunits, alters microRNA levels, and enhances global protein synthesis Proc Natl Acad Sci U S A Feb. 8, 2005 1865-1870 102.

Yu, B., Z. Yang, J. Li, S. Minakhina, M. Yang, R. W. Padgett, R. Steward and X. Chen. Methylation as a crucial step in plant microRNA biogenesis Science Feb. 11, 2005 932-935 307.

Kanellopoulou, C., S. A. Muljo, A. L. Kung, S. Ganesan, R. Drapkin, T. Jenuwein, D. M. Livingston and K. Rajewsky. Dicer-deficient mouse embryonic stem cells are defective in differentiation and centromeric silencing Genes Dev Feb. 15, 2005 489-501 19.

Pfeffer, S., A. Sewer, M. Lagos-Quintana, R. Sheridan, C. Sander, F. A. Grasser, L. F. Van Dyk, C. K. Ho, S. Shuman, M. Chien, J. J. Russo, J. Ju, G. Randall, B. D. Lindenbach, C. M. Rice, V. Simon, D. D. Ho, M. Zavolan and T. Tuschl. Identification of microRNAs of the herpesvirus family Nat Methods Feb. 16, 2005 269-276 2.

Lim, L. P., N. C. Lau, P. Garrett-Engele, A. Grimson, J. M. Schelter, J. Castle, D. P. Bartel, P. S. Linsley and J. M. Johnson. Microarray analysis shows that some microRNAs downregulate large numbers of target mRNAs Nature Feb. 17, 2005 769-773 433.

Xiao, Z., J. Xue, T. J. Sowin, S. H. Rosenberg and H. Zhang. A novel mechanism of checkpoint abrogation conferred by Chk1 downregulation Oncogene Feb. 17, 2005 1403-1411 24.

Shah, S., S. Rangarajan and S. H. Friedman. Light-activated RNA interference Angew Chem Int Ed Engl Feb. 18, 2005 1328-1332 44.

Karube, Y., H. Tanaka, H. Osada, S. Tomida, Y. Tatematsu, K. Yanagisawa, Y. Yatabe, J. Takamizawa, S. Miyoshi, T. Mitsudomi and T. Takahashi. Reduced expression of Dicer associated with poor prognosis in lung cancer patients Cancer Sci Feb. 2005 111-115 96.

Teixeira, M. R. and S. Heim. Multiple numerical chromosome aberrations in cancer: what are their causes and what are their consequences? Semin Cancer Biol Feb. 2005 3-12 15.

Kidner, C. A. and R. A. Martienssen. The developmental role of microRNA in plants Curr Opin Plant Biol Feb. 2005 38-44 8.

Li, Y., W. Li and Y. X. Jin. Computational identification of novel family members of microRNA genes in Arabidopsis thaliana and Oryza sativa Acta Biochim Biophys Sin (Shanghai) Feb. 2005 75-87 37.

Robb, G. B., K. M. Brown, J. Khurana and T. M. Rana. Specific and potent RNAi in the nucleus of human cells Nat Struct Mol Biol Feb. 2005 133-137 12.

Tang, G. siRNA and miRNA: an insight into RISCs Trends Biochem Sci Feb. 2005 106-114 30.

Westhof, E. and W. Filipowicz. From RNAi to epigenomes: how RNA rules the world Chembiochem Feb. 2005 441-443 6.

Kim, D. H., M. A. Behlke, S. D. Rose, M. S. Chang, S. Choi and J. J. Rossi. Synthetic dsRNA Dicer substrates enhance RNAi potency and efficacy Nat Biotechnol Feb. 2005 222-226 23.

Leonard, J. N. and D. V. Schaffer. Computational design of antiviral RNA interference strategies that resist human immunodeficiency virus escape J Virol Feb. 2005 1645-1654 79.

Siolas, D., C. Lerner, J. Burchard, W. Ge, P. S. Linsley, P. J. Paddison, G. J. Hannon and M. A. Cleary. Synthetic shRNAs as potent RNAi triggers Nat Biotechnol Feb. 2005 227-231 23.

Yi, R., B. P. Doehle, Y. Qin, I. G. Macara and B. R. Cullen. Overexpression of exportin 5 enhances Rna interference mediated by short hairpin RNAs and microRNAs Rna Feb (Epub Dec. 21, 2004) 2005 220-226 11.

Tomari, Y. and P. D. Zamore. Perspective: machines for RNAi Genes Dev Mar. 1, 2005 517-529 19.

Cheng, A. M., M. W. Byrom, J. Shelton and L. P. Ford. Antisense inhibition of human miRNAs and indications for an involvement of miRNA in cell growth and apoptosis Nucleic Acids Res Mar. 1, 2005 1290-1297 33.

Onishi, K. and S. Ueda. Molecular evolution of a microRNA cluster in the PWS/AS region among mammals Gene Mar. 1, 2005.

Wei, J. H., Y. F. Chou, Y. H. Ou, Y. H. Yeh, S. W. Tyan, T. P. Sun, C. Y. Shen and S. Y. Shieh. TTK/hMps1 participates in the regulation of DNA damage checkpoint response by phosphorylating CHK2 on threonine 68 J Biol Chem Mar. 4 (Epub Dec. 23, 2004) 2005 7748-7757 280.

Eis, P. S., W. Tam, L. Sun, A. Chadburn, Z. Li, M. F. Gomez, E. Lund and J. E. Dahlberg. Accumulation of miR-155 and BIC RNA in human B cell lymphomas Proc Natl Acad Sci U S A Mar. 8, 2005 3627-3632 102.

Kang, W., O. Nielsen, C. Fenger, R. G. Leslie, U. Holmskov and K. B. Reid. Induction of DMBT1 expression by reduced ERK activity during gastric mucosa differentiation-like process and its association with human gastric cancer Carcinogenesis Mar. 10, 2005.

Kessler, P. S. and M. Parsons. Probing the role of compartmentation of glycolysis in procyclic form Trypanosoma brucei: RNA interference studies of PEX14, hexokinase, and phosphofructokinase J Biol Chem Mar. 11, 2005 9030-9036 280.

Jing, Q., S. Huang, S. Guth, T. Zarubin, A. Motoyama, J. Chen, F. Di Padova, S. C. Lin, H. Gram and J. Han. Involvement of microRNA in AU-rich element-mediated mRNA instability Cell Mar. 11, 2005 623-634 120.

Johnson, S. M., H. Grosshans, J. Shingara, M. Byrom, R. Jarvis, A. Cheng, E. Labourier, K. L. Reinert, D. Brown and F. J. Slack. RAS is regulated by the let-7 microRNA family Cell Mar. 11, 2005 635-647 120.

Yang, W. J., D. D. Yang, S. Na, G. E. Sandusky, Q. Zhang and G. Zhao. Dicer is required for embryonic angiogenesis during mouse development J Biol Chem Mar. 11 (Epub Dec. 21, 2004) 2005 9330-9335 280.

Robins, H., Y. Li and R. W. Padgett. Incorporating structure to predict microRNA targets Proc Natl Acad Sci U S A Mar. 15, 2005 4006-4009 102.

Giraldez, A. J., R. M. Cinalli, M. E. Glasner, A. J. Enright, M. J. Thomson, S. Baskerville, S. M. Hammond, D. P. Bartel and A. F. Schier. MicroRNAs Regulate Brain Morphogenesis in Zebrafish Science Mar. 17, 2005.

Xie, X., J. Lu, E. J. Kulbokas, T. R. Golub, V. Mootha, K. Lindblad-Toh, E. S. Lander and M. Kellis. Systematic discovery of regulatory motifs in human promoters and 3' UTRs by comparison of several mammals Nature Mar. 17, 2005 338-345 434.

Best, A., L. Handoko, E. Schluter and H. U. Goringer. In vitro synthesized siRNAs elicit RNA interference in African trypanosomes—an in vitro and in vivo analysis J Biol Chem Mar. 21, 2005.

Lolle, S. J., J. L. Victor, J. M. Young and R. E. Pruitt. Genome-wide non-mendelian inheritance of extra-genomic information in Arabidopsis Nature Mar. 24, 2005 505-509 434.

Cai, X., S. Lu, Z. Zhang, C. M. Gonzalez, B. Damania and B. R. Cullen. Kaposi's sarcoma-associated herpesvirus expresses an array of viral microRNAs in latently infected cells Proc Natl Acad Sci U S A Mar. 30, 2005.

Rivas, F. V., N. H. Tolia, J. J. Song, J. P. Aragon, J. Liu, G. J. Hannon and L. Joshua-Tor. Purified Argonaute2 and an siRNA form recombinant human RISC Nat Struct Mol Biol Mar. 30, 2005.

Ma, J. B., Y. R. Yuan, G. Meister, Y. Pei, T. Tuschl and D. J. Patel. Structural basis for 5'-end-specific recognition of guide RNA by the A. fulgidus Piwi protein Nature Mar. 31, 2005 666-670 434.

Omoto, S. and Y. R. Fujii. Regulation of human immunodeficiency virus 1 transcription by nef microRNA J Gen Virol Mar. 2005 751-755 86.

Grosshans, H., T. Johnson, K. L. Reinert, M. Gerstein and F. J. Slack. The Temporal Patterning MicroRNA let-7 Regulates Several Transcription Factors at the Larval to Adult Transition in C. elegans Dev Cell Mar. 2005 321-330 8.

Lu, P. Y., F. Y. Xie and M. C. Woodle. Modulation of angiogenesis with siRNA inhibitors for novel therapeutics Trends Mol Med Mar. 2005 104-113 11.

Smirnova, L., A. Grafe, A. Seiler, S. Schumacher, R. Nitsch and F. G. Wulczyn. Regulation of miRNA expression during neural cell specification Eur J Neurosci Mar. 2005 1469-1477 21.

Voinnet, O. Induction and suppression of RNA silencing: insights from viral infections Nat Rev Genet Mar. 2005 206-220 6.

Guarguaglini, G., P. I. Duncan, Y. D. Stierhof, T. Holmstrom, S. Duensing and E. A. Nigg. The forkhead-associated domain protein Cep170 interacts with Polo-like kinase 1 and serves as a marker for mature centrioles Mol Biol Cell Mar. 2005 1095-1107 16.

Holway, A. H., C. Hung and W. M. Michael. Systematic, RNA-interference-mediated identification of mus-101 modifier genes in Caenorhabditis elegans Genetics Mar. 2005 1451-1460 169.

Mollinari, C., J. P. Kleman, Y. Saoudi, S. A. Jablonski, J. Perard, T. J. Yen and R. L. Margolis. Ablation of PRC1 by small interfering RNA demonstrates that cytokinetic abscission requires a central spindle bundle in mammalian cells, whereas completion of furrowing does not Mol Biol Cell Mar. 2005 1043-1055 16.

Tanno, B., V. Cesi, R. Vitali, F. Sesti, M. L. Giuffrida, C. Mancini, B. Calabretta and G. Raschella. Silencing of endogenous IGFBP-5 by micro Rna interference affects proliferation, apoptosis and differentiation of neuroblastoma cells Cell Death Differ Mar. 2005 213-223 12.

Brennecke, J., A. Stark, R. B. Russell and S. M. Cohen. Principles of microRNA-target recognition PLoS Biol Mar. 2005 e85 3.

Baskerville, S. And D. P. Bartel. Microarray profiling of microRNAs reveals frequent coexpression with neighboring miRNAs and host genes Rna Mar. 2005 241-247 11.

Legendre, M., A. Lambert and D. Gautheret. Profile-based detection of microRNA precursors in animal genomes Bioinformatics Apr. 1, 2005 841-845 21.

Walters, D. K., E. P. Stoffregen, M. C. Heinrich, M. W. Deininger and B. J. Druker. RNAi-induced down-regulation of FLT3 expression in AML cell lines increases sensitivity to MLN518 Blood Apr. 1, 2005 2952-2954 105.

Krek, A., D. Grun, M. N. Poy, R. Wolf, L. Rosenberg, E. J. Epstein, P. Macmenamin, I. Da Piedade, K. C. Gunsalus, M. Stoffel and N. Rajewsky. Combinatorial microRNA target predictions Nat Genet Apr. 3, 2005.

Vermeulen, A., L. Behlen, A. Reynolds, A. Wolfson, W. S. Marshall, J. Karpilow and A. Khvorova. The contributions of dsRNA structure to Dicer specificity and efficiency Rna Apr. 5, 2005.

Bahramian, M. B. and H. Zarbl. GENE impedance: a natural process for control of gene expression and the origin of RNA interference J Theor Biol Apr. 7, 2005 301-314 233.

Mattick, J. S. and I. V. Makunin. Small regulatory RNAs in mammals Hum Mol Genet Apr. 15, 2005 R121-132 14 Suppl 1.

Brown, J. R. and P. Sanseau. A computational view of microRNAs and their targets Drug Discov Today Apr. 15, 2005 595-601 10.

Lai, E. C., B. Tam and G. M. Rubin. Pervasive regulation of Drosophila Notch target genes by GYbox-, Brd-box-, and K-box-class microRNAs Genes Dev Apr. 15, 2005.

Kim, V. N. MicroRNA biogenesis: coordinated cropping and dicing Nat Rev Mol Cell Biol Apr. 15, 2005.

Lecellier, C. H., P. Dunoyer, K. Arar, J. Lehmann-Che, S. Eyquem, C. Himber, A. Saib and O. Voinnet. A cellular microRNA mediates antiviral defense in human cells Science Apr. 22, 2005 557-560 308.

Couzin, J. Molecular biology. Human RNA slows down a primate retrovirus Science Apr. 22, 2005 480-481 308.

Lee, Y. S., H. K. Kim, S. Chung, K. S. Kim and A. Dutta. Depletion of human micro-RNA miR-125b reveals that it is critical for the proliferation of differentiated cells but not for the down-regulation of putative targets during differentiation J Biol Chem Apr. 29, 2005 16635-16641 280.

Teixeira, D., U. Sheth, M. A. Valencia-Sanchez, M. Brengues and R. Parker. Processing bodies require RNA for assembly and contain nontranslating mRNAs RNA Apr. 2005 371-382 11.

Orban, T. I. and E. Izaurralde. Decay of mRNAs targeted by Risc requires XRN1, the Ski complex, and the exosome Rna Apr. 2005 459-469 11.

O'Toole A, S., S. Miller and M. J. Serra. Stability of 3' double nucleotide overhangs that model the 3' ends of siRNA Rna Apr. 2005 512-516 11.

Neilson, J. R. and P. A. Sharp. Herpesviruses throw a curve ball: new insights into microRNA biogenesis and evolution Nat Methods Apr. 2005 252-254 2.

Pasquinelli, A. E., S. Hunter and J. Bracht. MicroRNAs: a developing story Curr Opin Genet Dev Apr. 2005 200-205 15.

Chen, C. Z. and H. F. Lodish. MicroRNAs as regulators of mammalian hematopoiesis Semin Immunol Apr. 2005 155-165 17.

Knott, J. G., M. Kurokawa, R. A. Fissore, R. M. Schultz and C. J. Williams. Transgenic RNA interference reveals role for mouse sperm phospholipase Czeta in triggering Ca2+ oscillations during fertilization Biol Reprod Apr. 2005 992-996 72.

Latchoumycandane, C., V. Anantharam, M. Kitazawa, Y. Yang, A. Kanthasamy and A. G. Kanthasamy. Protein kinase Cdelta is a key downstream mediator of manganese-induced apoptosis in dopaminergic neuronal cells J Pharmacal Exp Ther Apr. 2005 46-55 313.

Gregory, R. I. and R. Shiekhattar. MicroRNA biogenesis and cancer Cancer Res May 1, 2005 3509-3512 65.

Jaronczyk, K., J. B. Carmichael and T. C. Hobman. Exploring the functions of RNA interference pathway proteins: some functions are more RISCy than others? Biochem J May 1, 2005 561-571 387.

Cheng, L. C., M. Tavazoie and F. Doetsch. Stem Cells From Epigeneticsto microRNAs Neuron May 5, 2005 363-367 46.

Liao, H. and J. H. Wang. Biomembrane-Permeable and Ribonuclease-Resistant siRNA with Enhanced Activity Oligonucleotides May 5, 2005.

Altuvia, Y., P. Landgraf, G. Lithwick, N. Elefant, S. Pfeffer, A. Aravin, M. J. Brownstein, T. Tuschl and H. Margalit. Clustering and conservation patterns of human microRNAs Nucleic Acids Res May 12, 2005 2697-2706 33.

Schubert, S., A. Grunweller, V. A. Erdmann and J. Kurreck. Local RNA Target Structure Influences siRNA Efficacy: Systematic Analysis of Intentionally Designed Binding Regions J Mol Biol May 13, 2005 883-893 348.

Overhoff, M., M. Alken, R. K. Far, M. Lemaitre, B. Lebleu, G. Sczakiel and I. Robbins. Local RNA Target Structure Influences siRNA Efficacy: a Systematic Global Analysis J Mol Biol May 13, 2005 871-881 348.

Li, Z., Y. Xiong, Y. Peng, J. Pan, Y. Chen, X. Wu, S. Hussain, P. Tien and D. Guo. Specific inhibition of HIV-1 replication by short hairpin RNAs targeting human cyclin T1 without inducing apoptosis FEBS Lett May 21, 2005.

Sen, G. L. and H. M. Blau. Argonaute 2/Risc resides in sites of mammalian mRNA decay known as cytoplasmic bodies Nat Cell Biol May 22, 2005.

Hobert, O. MicroRNAs: All Gone and Then What? Curr Biol May 24, 2005 R387-389 15.

Brown, K. M., C. Y. Chu and T. M. Rana. Target accessibility dictates the potency of human RiSC Nat Struct Mol Biol May 2005 469-470 12.

Bennasser, Y., S. Y. Le, M. Benkirane and K. T. Jeang. Evidence that HIV-1 Encodes an siRNA and a Suppressor of RNA Silencing Immunity May 2005 607-619 22.

Kong, Y. and J. H. Han. MicroRNA: biological and computational perspective Genomics Proteomics Bioinformatics May 2005 62-72 3.

Yu, L., X. Yu, R. Shen and Y. He. HYL1 gene maintains venation and polarity of leaves Planta May 2005 231-242 221.

Gong, H., C. M. Liu, D. P. Liu and C. C. Liang. The role of small RNAs in human diseases: potential troublemaker and therapeutic tools Med Res Rev May 2005 361-381 25.

Lee, R. C., R. L. Feinbaum and V. Ambros. The C. elegans heterochronic gene lin-4 encodes small RNAs with antisense complementarity to lin-14 Cell Dec. 3, 1993 843-854 75.

Wightman, B., I. Ha and G. Ruvkun. Posttranscriptional regulation of the heterochronic gene lin-14 by lin-4 mediates temporal pattern formation in C. elegans Cell Dec. 3, 1993 855-862 75.

Gallinaro, H., L. Domenjoud and M. Jacob. Structural study of the 5' end of a synthetic premessenger RNA from adenovirus. Evidence for a long-range exon-intron interaction J Mol Biol Jul. 15, 1994 205-225 240.

Lu, C. and R. Bablanian. Characterization of small nontranslated polyadenylylated RNAs in vaccinia virus-infected cells Proc Natl Acad Sci U S A Mar. 5, 1996 2037-2042 93.

Crawford, E. D., E. P. Deantoni, R. Etzioni, V. C. Schaefer, R. M. Olson and C. A. Ross. Serum prostate-specific antigen and digital rectal examination for early detection of prostate cancer in a national community-based program. The Prostate Cancer Education Council Urology Jun. 1996 863-869 47.

Engdahl HM, Hjalt TA, Wagner EG. A two unit antisense RNA cassette test system for silencing of target genes. Nucleic Acids Res. Aug. 15, 1997 3218-27 25.

Smith, D. S., P. A. Humphrey and W. J. Catalona. The early detection of prostate carcinoma with prostate specific antigen: the Washington University experience Cancer Nov. 1, 1997 1852-1856 80.

Dsouza, M., N. Larsen and R. Overbeek. Searching for patterns in genomic data Trends Genet Dec. 1997 497-498 13.

Moss, E. G., R. C. Lee and V. Ambros. The cold shock domain protein Lin-28 controls developmental timing C. elegans and is regulated by the lin-4 RNA Cell 1997 637 88.

Fire, A., S. Xu, M. K. Montgomery, S. A. Kostas, S. E. Driver and C. C. Mello. Potent and specific genetic interference by double-stranded RNA in Caenorhabditis elegans Nature Feb. 19, 1998 806-811 391.

Waterhouse, P. M., M. W. Graham and M. B. Wang. Virus resistance and gene silencing in plants can be induced by simultaneous expression of sense and antisense RNA Proc Natl Acad Sci U S A Nov. 10, 1998 13959-13964 95.

Ngo, H., C. Tschudi, K. Gull and E. Ullu. Double-stranded RNA induces mRNA degradation in Trypanosoma brucei Proc Natl Acad Sci U S A Dec. 8, 1998 14687-14692 95.

Verma, S. and F. Eckstein. Modified oligonucleotides: synthesis and strategy for users Annu Rev Biochem *No date in Pubmed* 1998 99-134 67.

Wuchty, S., W. Fontana, I. L. Hofacker and P. Schuster. Complete suboptimal folding of RNA and the stability of secondary structures Biopolymers Feb. 199 145-165 49.

Mathews, D. H., J. Sabina, M. Zuker and D. H. Turner. Expanded sequence dependence of thermodynamic parameters improves prediction of RNA secondary structure J Mol Biol May 21, 1999 911-940 288.

Chang, P. L. Encapsulation for somatic gene therapy Ann N Y Acad Sci Jun. 18, 199 146-158 875.

Zhang, M. Q. Large-scale gene expression data analysis: a new challenge to computational biologists Genome Res Aug. 1999 681-688 9.

Grisaru, D., M. Sternfeld, A. Eldor, D. Glick and H. Soreq. Structural roles of acetylcholinesterase variants in biology and pathology Eur J Biochem Sep. 1999 672-686 264.

Fire, A. RNA-triggered gene silencing Trends Genet Sep. 1999 358-363 15.

Tabara, H., M. Sarkissian, W. G. Kelly, J. Fleenor, A. Grishok, L. Timmons, A. Fire and C. C. Mello. The rde-1 gene, RNA interference, and transposon silencing in C. elegans Cell Oct. 15, 1999 123-132 99.

Ryo, A., Y. Suzuki, K. Ichiyama, T. Wakatsuki, N. Kondoh, A. Hada, M. Yamamoto and N. Yamamoto. Serial analysis of gene expression in HIV-1-infected T cell lines FEBS Lett Nov. 26, 1999 182-186 462.

Olsen, P. H. and V. Ambros. The lin-4 regulatory RNA controls developmental timing in Caenorhabditis elegans by blocking LIN-14 protein synthesis after the initiation of translation Dev Biol Dec. 15, 1999 671-680 216.

Tuschl, T., P. D. Zamore, R. Lehmann, D. P. Bartel and P. A. Sharp. Targeted mRNA degradation by double-stranded RNA in vitro Genes Dev Dec. 15, 1999 3191-3197 13.

Reinhart, B. J., F. J. Slack, M. Basson, A. E. Pasquinelli, J. C. Bettinger, A. E. Rougvie, H. R. Horvitz and G. Ruvkun. The 21-nucleotide let-7 RNA regulates developmental timing in Caenorhabditis elegans Nature Feb. 24, 2000 901-906 403.

Pitt, J. N., J. A. Schisa and J. R. Priess. P granules in the germ cells of Caenorhabditis elegans adults are associated with clusters of nuclear pores and contain Rna Dev Biol Mar. 15, 2000 315-333 219.

Hammond, S. M., E. Bernstein, D. Beach and G. J. Hannon. An RNA-directed nuclease mediates post-transcriptional gene silencing in Drosophila cells Nature Mar. 16, 2000 293-296 404.

Slack, F. J., M. Basson, Z. Liu, V. Ambros, H. R. Horvitz and G. Ruvkun. The lin-41 RBCC gene acts in the C. elegans heterochronic pathway between the let-7 regulatory Rna and the Lin-29 transcription factor Mol Cell Apr. 2000 659-669 5.

Fortier, E. and J. M. Belote. Temperature-dependent gene silencing by an expressed inverted repeat in Drosophila Genesis Apr. 2000 240-244 26.

Mourrain, P., C. Beclin, T. Elmayan, F. Feuerbach, C. Godon, J. B. Morel, D. Jouette, A. M. Lacombe, S. Nikic, N. Picault, K. Remoue, M. Sanial, T. A. Vo and H. Vaucheret. Arabidopsis SGS2 and SGS3 genes are required for posttranscriptional gene silencing and natural virus resistance Cell May 26, 2000 533-542 101.

Sijen, T. and J. M. Kooter. Post-transcriptional gene-silencing: RNAs on the attack or on the defense? Bioessays Jun. 2000 520-531 22.

Brenner, S., M. Johnson, J. Bridgham, G. Golda, D. H. Lloyd, D. Johnson, S. Luo, S. McCurdy, M. Foy, M. Ewan, R. Roth, D. George, S. Eletr, G. Albrecht, E. Vermaas, S. R. Williams, K. Moon, T. Burcham, M. Pallas, R. B. Dubridge, J. Kirchner, K. Fearon, J. Mao and K. Corcoran. Gene expression analysis by massively parallel signature sequencing (MPSS) on microbead arrays Nat Biotechnol Jun. 2000 630-634 18.

Ryo, A., Y. Suzuki, M. Arai, N. Kondoh, T. Wakatsuki, A. Hada, M. Shuda, K. Tanaka, C. Sato, M. Yamamoto and N. Yamamoto. Identification and characterization of differentially expressed mRNAs in HIV type 1-infected human T cells AIDS Res Hum Retroviruses Jul. 1, 2000 995 1005 16.

Nilsson, M., G. Barbany, D. O. Antson, K. Gertow and U. Landegren. Enhanced detection and distinction of RNA by enzymatic probe ligation Nat Biotechnol Jul. 2000 791-793 18.

Kent, W. J. and A. M. Zahler. Conservation, regulation, synteny, and introns in a large-scale C. briggsae-C. elegans genomic alignment Genome Res Aug. 2000 1115-1125 10.

Kennerdell, J. R. and R. W. Carthew. Heritable gene silencing in Drosophila using double-stranded RNA Nat Biotechnol Aug. 2000 896-898 18.

Smith, N. A., S. P. Singh, M. B. Wang, P. A. Stoutjesdijk, A. G. Green and P. M. Waterhouse. Total silencing by intron-spliced hairpin RNAs Nature Sep. 21, 2000 319-320 407.

Voinnet, O., C. Lederer and D. C. Baulcombe. A viral movement protein prevents spread of the gene silencing signal in Nicotiana benthamiana Cell Sep. 29, 2000 157-167 103.

Mette MF, Aufsatz W, van der Winden J, Matzke MA, Matzke AJ. Transcriptional silencing and promoter methylation triggered by double-stranded RNA. Embo J. Oct. 2, 2000 5194-201 19.

Yang, D., H. Lu and J. W. Erickson. Evidence that processed small dsRNAs may mediate sequence-specific mRNA degradation during RNAi in Drosophila embryos Curr Biol Oct. 5, 2000 1191.

Anandalakshmi, R., R. Marathe, X. Ge, J. M. Herr, Jr., C. Mau, A. Mallory, G. Pruss, L. Bowman and V. B. Vance. A calmodulin-related protein that suppresses posttranscriptional gene silencing in plants Science Oct. 6, 2000 142-144 290.

Fagard, M., S. Boutet, J. B. Morel, C. Bellini and H. Vaucheret. AGO1, QDE-2, and RDE-1 are related proteins required for post-transcriptional gene silencing in plants, quelling in fungi, and RNA interference in animals Proc Natl Acad Sci U S A Oct. 10, 2000 11650-11654 97.

Pasquinelli, A. E., B. J. Reinhart, F. Slack, M. Q. Martindale, M. I. Kuroda, B. Maller, D. C. Hayward, E. E. Ball, B. Degnan, P. Muller, J. Spring, A. Srinivasan, M. Fishman, J. Finnerty, J. Corbo, M. Levine, P. Leahy, E. Davidson and G. Ruvkun. Conservation of the sequence and temporal expression of let-7 heterochronic regulatory RNA Nature Nov. 2, 2000 86-89 408.

Llave, C., K. D. Kasschau and J. C. Carrington. Virus-encoded suppressor of posttranscriptional gene silencing targets a maintenance step in the silencing pathway Proc Natl Acad Sci U S A Nov. 21, 2000 13401-13406 9.

Cogoni, C. and G. Macino. Post-transcriptional gene silencing across kingdoms Curr Opin Genet Dev Dec. 2000 638-643 10.

Elbashir, S. M., W. Lendeckel and T. Tuschl. RNA interference is mediated by 21- and 22-nucleotide RNAs Genes Dev Jan. 15, 2001 188-200 15.

Bernstein, E., A. A. Caudy, S. M. Hammond and G. J. Hannon. Role for a bidentate ribonuclease in the initiation step of RNA interference Nature Jan. 18, 2001 363-366 409.

Vaucheret, H. and M. Fagard. Transcriptional gene silencing in plants: targets, inducers and regulators Trends Genet Jan. 2001 29-35 17.

Thomas, C. L., L. Jones, D. C. Baulcombe and A. J. Maule. Size constraints for targeting post-transcriptional gene silencing and for RNA-directed methylation in Nicotiana benthamiana using a potato virus X vector Plant J Feb. 2001 417-425 25.

Galyam, N., D. Grisaru, M. Grifman, N. Melamed-Book, F. Eckstein, S. Seidman, A. Eldor and H. Soreq. Complex host cell responses to antisense suppression of ACHE gene expression Antisense Nucleic Acid Drug Dev Feb. 2001 51-57 11.

Sharp, P. A. RNA interference—2001 Genes Dev Mar. 1, 2001 485-490 15.

Mallory, A. C., L. Ely, T. H. Smith, R. Marathe, R. Anandalakshmi, M. Fagard, H. Vaucheret, G. Pruss, L. Bowman and V. B. Vance. HC-Pro suppression of transgene silencing eliminates the small RNAs but not transgene methylation or the mobile signal Plant Cell Mar. 2001 571-583 13.

Matzke, M. A., A. J. Matzke, G. J. Pruss and V. B. Vance. RNA-based silencing strategies in plants Curr Opin Genet Dev Apr. 2001 221-227 11.

Schisa, J. A., J. N. Pitt and J. R. Priess. Analysis of RNA associated with P granules in germ cells of C elegans adults Development Apr. 2001 1287-1298 128.

Di Serio, F., H. Schob, A. Iglesias, C. Tarina, E. Bouldoires and F. Meins, Jr. Sense- and antisense-mediated gene silencing in tobacco is inhibited by the same viral suppressors and is associated with accumulation of small RNAs Proc Natl Acad Sci U S A May 22, 2001 6506-6510 98.

Elbashir, S. M., J. Harborth, W. Lendeckel, A. Yalcin, K. Weber and T. Tuschl. Duplexes of 21-nucleotide RNAs mediate RNA interference in cultured mammalian cells Nature May 24, 2001 494-498 411.

Piccin, A., A. Salameh, C. Benna, F. Sandrelli, G. Mazzotta, M. Zordan, E. Rosato, C. P. Kyriacou and R. Costa. Efficient and heritable functional knock-out of an adult phenotype in Drosophila using a GAL4-driven hairpin RNA incorporating a heterologous spacer Nucleic Acids Res Jun. 15, 2001 E55-55 29.

Vance, V. and H. Vaucheret. RNA silencing in plants—defense and counterdefense Science Jun. 22, 2001 2277-2280 292.

Argaman, L., R. Hershberg, J. Vogel, G. Bejerano, E. G. Wagner, H. Margalit and S. Altuvia. Novel small RNA-encoding genes in the intergenic regions of *Escherichia coli* Curr Biol Jun. 26, 2001 941-950 11.

Grishok, A., A. E. Pasquinelli, D. Conte, N. Li, S. Parrish, I. Ha, D. L. Baillie, A. Fire, G. Ruvkun and C. C. Mello. Genes and mechanisms related to RNA interference regulate expression of the small temporal RNAs that control C. elegans developmental timing Cell Jul. 13, 2001 23-34 106.

Hutvagner, G., J. Mclachlan, A. E. Pasquinelli, E. Balint, T. Tuschl and P. D. Zamore. A cellular function for the RNA-interference enzyme Dicer in the maturation of the let-7 small temporal RNA Science Aug. 3, 2001 834-838 293.

Hammond, S. M., S. Boettcher, A. A. Caudy, R. Kobayashi and G. J. Hannon. Argonaute2, a link between genetic and biochemical analyses of RNAi Science Aug. 10, 2001 1146-1150 293.

Vaucheret, H., C. Beclin and M. Fagard. Post-transcriptional gene silencing in plants J Cell Sci Sep. 2001 3083-3091 114.

Wesley, S. V., C. A. Helliwell, N. A. Smith, M. B. Wang, D. T. Rouse, Q. Liu, P. S. Gooding, S. P. Singh, D. Abbott, P. A. Stoutjesdijk, S. P. Robinson, A. P. Gleave, A. G. Green and P. M. Waterhouse. Construct design for efficient, effective and high-throughput gene silencing in plants J Sep. 2001 581-590 27.

Mattick, J. S. and M. J. Gagen. The evolution of controlled multitasked gene networks: the role of introns and other noncoding RNAs in the development of complex organisms Mol Biol Evol Sep. 2001 1611-1630 18.

Carter, R. J., I. Dubchak and S. R. Holbrook. A computational approach to identify genes for functional RNAs in genomic sequences Nucleic Acids Res Oct. 1, 2001 3928-3938 29.

Moss, E. G. RNA interference: it's a small RNA world Curr Biol Oct. 2, 2001 R772-775 11.

Ketting, R. F., S. E. Fischer, E. Bernstein, T. Sijen, G. J. Hannon and R. H. Plasterk. Dicer functions in RNA interference and in synthesis of small RNA involved in developmental timing in C. elegans Genes Dev Oct. 15, 2001 2564-2659 15.

Ruvkun, G. Molecular biology. Glimpses of a tiny RNA world Science Oct. 26, 2001 797-799 294

Lee, R. C. and V. Ambros. An extensive class of small RNAs in Caenorhabditis elegans Science Oct. 26, 2001 862-864 294.

Lau, N. C., L. P. Lim, E. G. Weinstein and D. P. Bartel. An abundant class of tiny RNAs with portable regulatory roles in Caenorhabditis elegans Science Oct. 26, 2001 858-862 294.

Lagos-Quintana, M., R. Rauhut, W. Lendeckel and T. Tuschl. Identification of novel genes coding for small expressed RNAs Science Oct. 26, 2001 853-858 294.

Itaya, A., A. Folimonov, Y. Matsuda, R. S. Nelson and B. Ding. Potato spindle tuber viroid as inducer of RNA silencing in infected tomato Mol Plant Microbe Interact Nov. 2001 1332-1334 14.

Mattick, J. S. Non-coding RNAs: the architects of eukaryotic complexity EMBO Rep Nov. 2001 986-991 2.

Elbashir, S. M., J. Martinez, A. Patkaniowska, W. Lendeckel and T. Tuschl. Functional anatomy of siRNAs for mediating efficient RNAi in Drosophila melanogaster embryo lysate Embo J Dec. 3, 2001 6877-6888 20.

Ambros, V. microRNAs: tiny regulators with great potential Cell Dec. 28, 2001 823-826 107.

Blaszczyk, J., J. E. Tropea, M. Bubunenko, K. M. Routzahn, D. S. Waugh, D. L. Court and X. Ji. Crystallographic and modeling studies of RNase III suggest a mechanism for double-stranded RNA cleavage Structure Dec. 2001 1225-1236 9.

Crete, P., S. Leuenberger, V. A. Iglesias, V. Suarez, H. Schob, H. Holtorf, S. Van Eeden and F. Meins. Graft transmission of induced and spontaneous post-transcriptional silencing of chitinase genes Plant J Dec. 2001 493-501 28.

Smallridge, R. A small fortune Nat Rev Mol Cell Biol Dec.2001 867 2.

Eddy, S. R. Non-coding RNA genes and the modern RNA world Nat Rev Genet Dec. 2001 919-929 2.

Lu, C. M. miRNA bead detection Genaco Biomedical Products PHS 398 2001 1.

Matzke, M., A. J. Matzke and J. M. Kooter. RNA: guiding gene silencing 2001 1080 293.

Grosshans, H. and F. J. Slack. Micro-RNAs: small is plentiful J Cell Biol Jan. 7, 2002 17-21 156.

Meshorer, E., C. Erb, R. Gazit, L. Pavlovsky, D. Kaufer, A. Friedman, D. Glick, N. Benarie and H. Soreq. Alternative splicing and neuritic mRNA translocation under long-term neuronal hypersensitivity Science Jan. 18, 2002 508-512 295.

Paddison, P. J., A. A. Caudy and G. J. Hannon. Stable suppression of gene expression by RNAi in mammalian cells Proc Natl Acad Sci U S A Feb. 5, 2002 1443-1448 99.

Moss, E. G. MicroRNAs: hidden in the genome Curr Biol Feb. 19, 2002 R138-140 12.

Banerjee, D. and F. Slack. Control of developmental timing by small temporal RNAs: a paradigm for RNA-mediated regulation of gene expression Bioessays Feb. 2002 119-129 24.

Elbashir, S. M., J. Harborth, K. Weber and T. Tuschl. Analysis of gene function in somatic mammalian cells using small interfering RNAs Methods Feb. 2002 199-213 26.

Han, Y. and D. Grierson. Relationship between small antisense RNAs and aberrant RNAs associated with sense transgene mediated gene silencing in tomato Plant J Feb. 2002 509-519 29.

Nicholson, R. H. and A. W. Nicholson. Molecular characterization of a mouse cDNA encoding Dicer, a ribonuclease III ortholog involved in RNA interference Mamm Genome Feb. 2002 67-73 13.

Puerta-Fernandez, E., A. Barroso-Deljesus and A. Berzal-Herranz. Anchoring hairpin ribozymes to long target RNAs by loop-loop RNA interactions Antisense Nucleic Acid Drug Dev Feb. 2002 1-9 12.

Giordano, E., R. Rendina, I. Peluso and M. Furia. RNAi triggered by symmetrically transcribed transgenes in Drosophila melanogaster Genetics Feb. 2002 637-648 160.

Martens, H., J. Novotny, J. Oberstrass, T. L. Steck, P. Postlethwait and W. Nellen. RNAi in Dictyostelium: the role of RNA-directed RNA polymerases and double-stranded RNase Mol Biol Cell Feb. 2002 445-453 13.

Mourelatos, Z., J. Dostie, S. Paushkin, A. Sharma, B. Charroux, L. Abel, J. Rappsilber, M. Mann and G. Dreyfuss. miRNPs: a novel class of ribonucleoproteins containing numerous microRNAs Genes Dev Mar. 15, 2002 720-728 16.

Seggerson, K., L. Tang and E. G. Moss. Two genetic circuits repress the Caenorhabditis elegans heterochronic gene lin-28 after translation initiation Dev Biol Mar. 15, 2002 215-225 243.

Morel, J. B., C. Godon, P. Mourrain, C. Beclin, S. Boutet, F. Feuerbach, F. Proux and H. Vaucheret. Fertile hypomorphic Argonaute (ago1) mutants impaired in post-transcriptional gene silencing and virus resistance Plant Cell Mar. 2002 629-639 14.

Catalanotto, C., G. Azzalin, G. Macino and C. Cogoni. Involvement of small RNAs and role of the qde genes in the gene silencing pathway in Neurospora Genes Dev Apr. 1, 2002 790-795 16.

Boutla, A., K. Kalantidis, N. Tavernarakis, M. Tsagris and M. Tabler. Induction of RNA interference in Caenorhabditis elegans by RNAs derived from plants exhibiting post-transcriptional gene silencing Nucleic Acids Res Apr. 1, 2002 1688-1694 30.

Pasquinelli, A. E. and G. Ruvkun. Control of developmental timing by micrornas and their targets Annu Rev Cell Dev Biol Epub 2002 Apr. 2, 2002 495-513 18.

Paddison, P. J., A. A. Caudy, E. Bernstein, G. J. Hannon and D. S. Conklin. Short hairpin RNAs (shRNAs) induce sequence-specific silencing in mammalian cells Genes Dev Apr. 15, 2002 948-958 16.

Beclin, C., S. Boutet, P. Waterhouse and H. Vaucheret. A branched pathway for transgene-induced RNA silencing in plants Curr Biol Apr. 16, 2002 684-688 12.

Eddy, S. R. Computational genomics of noncoding RNA genes Cell Apr. 19, 2002 137-140 109.

Lagos-Quintana, M., R. Rauhut, A. Yalcin, J. Meyer, W. Lendeckel and T. Tuschl. Identification of tissue-specific microRNAs from mouse Curr Biol Apr. 30, 2002 735-739 12.

Kent, W. J. BLAT—the BLAST-like alignment tool Genome Res Apr. 2002 656-6654 12.

Hutvagner, G. and P. D. Zamore. RNAi: nature abhors a double-strand Curr Opin Genet Dev Apr. 2002 225-232 12.

Nilsson, M., J. Baner, M. Mendel-Hartvig, F. Dahl, D. O. Antson, M. Gullberg and U Landegren. Making ends meet in genetic analysis analysis using padlock probes Hum Mutat Apr. 2002 410-415 19.

Pasquinelli, A. E. MicroRNAs: deviants no longer Trends Genet Apr. 2002 171-173 18.

Lai, E. C. Micro RNAs are complementary to 3' UTR sequence motifs that mediate negative post-transcriptional regulation Nat Genet Apr. 2002 363-364 30.

Schwarz, D. S. and P. D. Zamore. Why do miRNAs live in the miRNP? Genes Dev May 1, 2002 1025-1031 16.

Brantl, S. Antisense-RNA regulation and RNA interference Biochim Biophys Acta May 3, 2002 15-25 1575.

Li, H., W. X. Li and S. W. Ding. Induction and suppression of RNA silencing by an animal virus Science May 17, 2002 1319-1321 296.

Zamore, P. D. Ancient pathways programmed by small RNAs Science May 17, 2002 1265-1269 296.

Chen, S., E. A. Lesnik, T. A. Hall, R. Sampath, R. H. Griffey, D. J. Ecker and L. B. Blyn. A bioinformatics based approach to discover small RNA genes in the Escherichia coli genome Biosystems Mar.-May 2002 157-177 65.

Lee, N. S., T. Dohjima, G. Bauer, H. Li, M. J. Li, A. Ehsani, P. Salvaterra and J. Rossi. Expression of small interfering RNAs targeted against HIV-1 rev transcripts in human cells Nat Biotechnol May 2002 500-505 20.

Draghici, S. Statistical intelligence: effective analysis of high-density microarray data Drug Discov Today Jun. 1, 2002 S55-63 7.

Silhavy, D., A. Molnar, A. Lucioli, G. Szittya, C. Hornyik, M. Tavazza and J. Burgyan. A viral protein suppresses RNA silencing and binds silencing-generated, 21- to 25-nucleotide double-stranded RNAs Embo J Jun. 17, 2002 3070-3080 21.

Ayash-Rashkovsky, M., Z. Weisman, J. Diveley, R. B. Moss, Z. Bentwich and G. Borkow. Generation of Th1 immune responses to inactivated, gp120-depleted HIV-1 in mice with a dominant Th2 biased immune profile via immunostimulatory [correction of imunostimulatory] oligonucleotides—relevance to AIDS vaccines in developing countries Vaccine Jun. 21, 2002 2684-2692 20.

Tabara, H., E. Yigit, H. Siomi and C. C. Mello. The dsRNA binding protein RDE-4 interacts with RDE-1, DCR-1, and a DExH-box helicase to direct RNAi in C. elegans Cell Jun. 28, 2002 861-871.

Bettencourt, R., O. Terenius and I. Faye. Hemolin gene silencing by ds-RNA injected into Cecropia pupae is lethal to next generation embryos Insect Mol Biol Jun. 2002 267-271 11.

Hooper, N. M. and A. J. Turner. The search for alpha-secretase and its potential as a therapeutic approach to Alzheimer s disease Curr Med Chem Jun. 2002 1107-1119 9.

Liu, Q., S. Singh and A. Green. High-oleic and high-stearic cottonseed oils: nutritionally improved cooking oils developed using gene silencing J Am Coll Nutr Jun. 2002 205S-211S 21.

Zeng, Y., E. J. Wagner and B. R. Cullen. Both natural and designed micro RNAs can inhibit the expression of cognate mRNAs when expressed in human cells Mol Cell Jun. 2002 1327-1333 9.

McManus, M. T., C. P. Petersen, B. B. Haines, J. Chen and P. A. Sharp. Gene silencing using micro-RNA designed hairpins Rna Jun. 2002 842-850 8.

Reinhart, B. J., E. G. Weinstein, M. W. Rhoades, B. Bartel and D. P. Bartel. MicroRNAs in plants Genes Dev Jul. 1, 2002 1616-1626 16.

McCaffrey, A. P., L. Meuse, T. T. Pham, D. S. Conklin, G. J. Hannon and M. A. Kay. RNA interference in adult mice Nature Jul. 4, 2002 38-39 418.

Hannon, G. J. RNA interference Nature Jul. 11, 2002 244-251 418.

Dennis, C. The brave new world of RNAna Nature Jul. 11, 2002 122-124 418.

Jacque, J. M., K. Triques and M. Stevenson. Modulation of HIV-1 replication by RNA interference Nature Jul. 25, 2002 435-438 418.

Cullen, B. R. RNA interference: antiviral defense and genetic tool Nat Immunol Jul. 2002 597-599 3.

Ma, C. and A. Mitra. Intrinsic direct repeats generate consistent post-transcriptional gene silencing in tobacco Plant J Jul. 2002 37-49 31.

Novina, C. D., M. F. Murray, D. M. Dykxhoorn, P. J. Beresford, J. Riess, S. K. Lee, R. G. Collman, J. Lieberman, P. Shankar and P. A. Sharp. siRNA-directed inhibition of HIV-1 infection Nat Med Jul. 2002 681-686 8.

Pomerantz, R, J. RNA interference meets HIV-1: will silence be golden? Nat Med Jul. 2002 659-660 8.

Zeng, Y. and B. R. Cullen. RNA interference in human cells is restricted to the cytoplasm RNA Jul. 2002 855-860 8.

Xiang, C. C., O. A. Kozhich, M. Chen, J. M. Inman, Q. N. Phan, Y. Chen and M. J. Brownstein. Amine-modified random primers to label probes for DNA microarrays Nat Biotechnol Jul. 2002 738-742 20.

Llave, C., K. D. Kasschau, M. A. Rector and J. C. Carrington. Endogenous and silencing-associated small RNAs in plants Plant Cell Jul. 2002 1605-1619 14.

Rhoades, M. W., B. J. Reinhart, L. P. Lim, C. B. Burge, B. Bartel and D. P. Bartel. Prediction of plant microRNA targets Cell Aug. 23, 2002 513-520 110.

Hipfner, D. R., K. Weigmann and S. M. Cohen. The bantam gene regulates Drosophila growth Aug. 2002 1527-1537 161.

Liu, Q., S. P. Singh and A. G. Green. High-stearic and High-oleic cottonseed oils produced by hairpin RNA-mediated post-transcriptional gene silencing Plant Physiol Aug. 2002 1732-1743 129.

Stoutjesdijk, P. A., S. P. Singh, Q. Liu, C. J. Hurlstone, P. A. Waterhouse and A. G. Green. hpRNA-mediated targeting of the Arabidopsis FAD2 gene gives highly efficient and stable silencing Plant Physiol Aug. 2002 1723-1731 129.

Suzuma, S., S. Asari, K. Bunai, K. Yoshino, Y. Ando, H. Kakeshita, M. Fujita, K. Nakamura and K. Yamane. Identification and characterization of novel small RNAs in the aspS-yrvM intergenic region of the Bacillus subtilis genome Microbiology Aug. 2002 2591-2598 148.

Milligan, L., T. Forne, E. Antoine, M. Weber, B. Hemonnot, L. Dandolo, C. Brunel and G. Cathala. Turnover of primary transcripts is a major step in the regulation of mouse H19 gene expression EMBO Rep Aug. 2002 774-779 3.

Hamilton, A., O. Voinnet, L. Chappell and D. Baulcombe. Two classes of short interfering RNA in RNA silencing Embo J Sep. 2, 2002 4671-4679 21.

Lee, Y., K. Jeon, J. T. Lee, S. Kim and V. N. Kim. MicroRNA maturation: stepwise processing and subcellular localization Embo J Sep. 2, 2002 4663-4670 21.

Klahre, U., P. Crete, S. A. Leuenberger, V. A. Iglesias and F. Meins, Jr. High molecular weight RNAs and small interfering RNAs induce systemic posttranscriptional gene silencing in plants Proc Natl Acad Sci U S A Sep. 3, 2002 11981-11986 99.

Park, W., J. Li, R. Song, J. Messing and X. Chen. Carpel Factory, a Dicer homolog, and HEN1, a novel protein, act in microRNA metabolism in Arabidopsis thaliana Curr Biol Sep. 3, 2002 1484-1495 12.

Jiang, M. And J. Milner. Selective silencing of viral gene expression in Hpv-positive human cervical carcinoma cells treated with siRNA, a primer of RNA interference Oncogene Sep. 5, 2002 6041-6048 21.

Martinez, J., A. Patkaniowska, H. Urlaub, R. Luhrmann and T. Tuschl. Single-stranded antisense siRNAs guide target RNA cleavage in RNAi Cell Sep. 6, 2002 563-574 110.

Allshire, R. Molecular biology. RNAi and heterochromatin—a hushed-up affair Science Sep. 13, 2002 1818-1819 297.

Reinhart, B. J. and D. P. Bartel. Small RNAs correspond to centromere heterochromatic repeats Science Sep. 13, 2002 1831 297.

Volpe, T. A., C. Kidner, I. M. Hall, G. Teng, S. I. Grewal and R. A. Martienssen. Regulation of heterochromatic silencing and histone H3 lysine-9 methylation by RNAi Science Sep. 13, 2002 1833-1837 297.

Baulcombe, D. DNA events. An RNA microcosm Science Sep. 20, 2002 2002-2003 297.

Llave, C., Z. Xie, K. D. Kasschau and J. C. Carrington. Cleavage of Scarecrow-like mRNA targets directed by a class of Arabidopsis miRNA Science Sep. 20, 2002 2053-2056 297.

Mochizuki, K., N. A. Fine, T. Fujisawa and M. A. Gorovsky. Analysis of a piwi-related gene implicates small RNAs in genome rearrangement in tetrahymena Cell Sep. 20, 2002 689-699 110.

Hutvagner, G. and P. D. Zamore. A microRNA in a multiple-turnover RNAi enzyme complex Science Sep. 20, 2002 2056-2060 297.

Coburn, G. A. and B. R. Cullen. Potent and specific inhibition of human immunodeficiency virus type 1 replication by RNA interference J Virol Sep. 2002 9225-9231 76.

Caudy, A. A., M. Myers, G. J. Hannon and S. M. Hammond. Fragile X-related protein and VIG associate with the RNA interference machinery Genes Dev Oct. 1, 2002 2491-2496 16.

Ishizuka, A., M. C. Siomi and H. Siomi. A Drosophila fragile X protein interacts with components of RNAi and ribosomal proteins Genes Dev Oct. 1, 2002 2497-2508 16.

Voinnet, O. RNA silencing: small RNAs as ubiquitous regulators of gene expression Curr Opin Plant Biol Oct. 2002 444-451 5.

Golden, T. A., S. E. Schauer, J. D. Lang, S. Pien, A. R. Mushegian, U. Grossniklaus, D. W. Meinke and A. Ray. Short INTEGUMENTS1/SUSPENSOR1/Carpel Factory, a Dicer homolog, is a maternal effect gene required for embryo development in Arabidopsis Plant Physiol Oct. 2002 808-822 130.

Merkle, I., M. J. Van Ooij, F. J. Van Kuppeveld, D. H. Glaudemans, J. M. Galama, A. Henke, R. Zell and W. J. Melchers. Biological significance of a human enterovirus B-specific RNA element in the 3' nontranslated region J Virol Oct. 2002 9900-9909 76.

Froeyen, M. and P. Herdewijn. RNA as a target for drug design, the example of Tat-TAR interaction Curr Top Med Chem Oct. 2002 1123-1145 2.

Carmell, M. A., Z. Xuan, M. Q. Zhang and G. J. Hannon. The Argonaute family: tentacles that reach into RNAi, developmental control, stem cell maintenance, and tumorigenesis Genes Dev Nov. 1, 2002 2733-2742 16.

Provost, P., D. Dishart, J. Doucet, D. Frendewey, B. Samuelsson and O. Radmark. Ribonuclease activity and RNA binding of recombinant human Dicer Embo J Nov. 1, 2002 5864-5874.

Zhang, H., F. A. Kolb, V. Brondani, E. Billy and W. Filipowicz. Human Dicer preferentially cleaves dsRNAs at their termini without a requirement for Atp Embo J Nov. 1, 2002 5875-5885 21.

Mallory, A. C., B. J. Reinhart, D. Bartel, V. B. Vance and L. H. Bowman. A viral suppressor of RNA silencing differentially regulates the accumulation of short interfering RNAs and micro-RNAs in tobacco Proc Natl Acad Sci U S A Nov. 12, 2002 15228-15233 99.

Gottesman, S. Stealth regulation: biological circuits with small RNA switches Genes Dev Nov. 15, 2002 2829-2842 16.

Calin, G. A., C. D. Dumitru, M. Shimizu, R. Bichi, S. Zupo, E. Noch, H. Aldler, S. Rattan, M. Keating, K. Rai, L. Rassenti, T. Kipps, M. Negrini, F. Bullrich and C. M. Croce. Frequent deletions and downregulation of micro- RNA genes miR15 and miR16 at 13q14 in chronic lymphocytic leukemia Proc Natl Acad Sci U S A Nov. 26, 2002 15524-15529 99.

Gaudilliere, B., Y. Shi and A. Bonni. RNA interference reveals a requirement for myocyte enhancer factor 2A in activity-dependent neuronal survival J Biol Chem Nov. 29, 2002 46442-46446.

Jones, L. Revealing micro-RNAs in plants Trends Plant Sci Nov. 2002 473-475 7.

Schauer, S. E., S. E. Jacobsen, D. W. Meinke and a. Ray. Dicer-LIKE1: blind men and elephants in Arabidopsis development Trends Plant Sci Nov. 2002 487-491 7.

Okazaki, Y., M. Furuno, T. Kasukawa, J. Adachi, H. Bono, S. Kondo, et al. Analysis of the mouse transcriptome based on functional annotation of 60,770 full-length cDNAs Nature Dec. 5, 2002.

Dennis, C. Small RNAs: the genome's guiding hand? Nature Dec. 19-26, 2002 732 420.

Uchida, N., S. Hoshino, H. Imataka, N. Sonenberg and T. Katada. A novel role of the mammalian GSPT/eRF3 associating with poly(A)-binding protein in Cap/Poly(A)-dependent translation J Biol Chem Dec. 27, 2002 50286-50292 277.

Huttenhofer, A., J. Brosius and J. P. Bachellerie. RNomics: identification and function of small, non-messenger RNAs Curr Opin Chem Biol Dec. 2002 835-843 6.

Wood, N. T. Unravelling the molecular basis of viral suppression of PTGS Trends Plant Sci 2002 384 7.

Cohen, O., C. Erb, D. Ginzberg, Y. Pollak, S. Seidman, S. Shoham, R. Yirmiya and H. Soreq. Neuronal overexpression of "readthrough" acetylcholinesterase is associated with antisense-suppressible behavioral impairments Mol Psychiatry *No date in pubmed* 2002 874-885 7.

Mlotshwa, S., O. Voinnet, M. F. Mette, M. Matzke, H. Vaucheret, S. W. Ding, G. Pruss and V. B. Vance. RNA silencing and the mobile silencing signal Plant Cell *No date in pubmed* 2002 S289-301 14 Suppl.

Tang, G., B. J. Reinhart, D. P. Bartel and P. D. Zamore. A biochemical framework for RNA silencing in plants Genes Dev Jan. 1, 2003 49-63 17.

Kawasaki, H. and K. Taira. Short hairpin type of dsRNAs that are controlled by tRNA(Val) promoter significantly induce RNAi-mediated gene silencing in the cytoplasm of human cells Nucleic Acids Res Jan. 15, 2003 700-707 31.

Ashrafi, K., F. Y. Chang, J. L. Watts, A. G. Fraser, R. S. Kamath, J. Ahringer and G. Ruvkun. Genome-wide RNAi analysis of Caenorhabditis elegans fat regulatory genes Nature Jan. 16, 2003 268-272 421.

Kamath, R. S., A. G. Fraser, Y. Dong, G. Poulin, R. Durbin, M. Gotta, A. Kanapin, N. Le Bot, S. Moreno, M. Sohrmann, D. P. Welchman, P. Zipperlen and J. Ahringer. Systematic functional analysis of the Caenorhabditis elegans genome using RNAi Nature Jan. 16, 2003 231-237 421.

Tuschl, T. Functional genomics: RNA sets the standard Nature Jan. 16, 2003 220-221 421.

Iyer, L. M., E. V. Koonin and L. Aravind. Evolutionary connection between the catalytic subunits of DNA-dependent RNA polymerases and eukaryotic RNA-dependent RNA polymerases and the origin of RNA polymerases BMC Struct Biol Jan. 28, 2003 1 3.

Shi, Y. Mammalian RNAi for the masses Trends Genet Jan. 2003 9-12 19.

Cerutti, H. RNA interference: traveling in the cell and gaining functions? Trends Genet Jan. 2003 39-46 19.

Zeng, Y. and B. R. Cullen. Sequence requirements for micro RNA processing and function in human cells RNA Jan. 2003 112-123 9.

Kawasaki, H., E. Suyama, M. Iyo and K. Taira. siRNAs generated by recombinant human Dicer induce specific and significant but target site-independent gene silencing in human cells Nucleic Acids Res Feb. 1, 2003 981-987 31.

Reiner, A., D. Yekutieli and Y. Benjamin I. Identifying differentially expressed genes using false discovery rate controlling procedures Bioinformatics Feb. 12, 2003 368-375 19.

Doench, J. G., C. P. Petersen and P. A. Sharp. siRNAs can function as miRNAs Genes Dev Feb. 15, 2003 438-442 17.

Gupta, V., A. Cherkassky, P. Chatis, R. Joseph, A. L. Johnson, J. Broadbent, T. Erickson and J. Dimeo. Directly labeled mRNA produces highly precise and unbiased differential gene expression data Nucleic Acids Res Feb. 15, 2003 e13 31.

Boffelli, D., J. Mcauliffe, D. Ovcharenko, K. D. Lewis, I. Ovcharenko, L. Pachter and E. M. Rubin. Phylogenetic shadowing of primate sequences to find functional regions of the human genome Science Feb. 28, 2003 1391-1394 299.

Kasschau, K. D., Z. Xie, E. Allen, C. Llave, E. J. Chapman, K. A. Krizan and J. C. Carrington. P1/HC-Pro, a viral suppressor of RNA silencing, interferes with Arabidopsis development and miRNA unction Dev Cell Feb. 2003 205-217 4.

Carmell, M. A., L. Zhang, D. S. Conklin, G. J. Hannon and T. A. Rosenquist. Germline transmission of RNAi in mice Nat Struct Biol Feb. 2003 91-92 10.

Dostie, J., Z. Mourelatos, M. Yang, A. Sharma and G. Dreyfuss. Numerous microRNPs in neuronal cells containing novel microRNAs RNA Feb. 2003 180-186 9.

Lagos-Quintana, M., R. Rauhut, J. Meyer, A. Borkhardt and T. Tuschl. New microRNAs from mouse and human Rna Feb. 2003 175-179 9.

Wilson, J. A., S. Jayasena, A. Khvorova, S. Sabatinos, I. G. Rodrigue-Gervais, S. Arya, F. Sarangi, M. Harris-Brandts, S. Beaulieu and C. D. Richardson. RNA interference blocks gene expression and RNA synthesis from hepatitis C replicons propagated in human liver cells Proc Natl Acad Sci U S Aa Mar. 4, 2003 2783-2788 100.

Lim, L. P., M. E. Glasner, S. Yekta, C. B. Burge and D. P. Bartel. Vertebrate microRNA genes Science Mar. 7, 2003 1540 299.

Maniataki, E., A. E. Martinez De Alba, R. Sagesser, M. Tabler and M. Tsagris. Viroid RNA systemic spread may depend on the interaction of a 71-nucleotide bulged hairpin with the host protein VirP1 Rna Mar. 2003 346-354 9.

Ambros, V., B. Bartel, D. P. Bartel, C. B. Burge, J. C. Carrington, X. Chen, G. Dreyfuss, S. R. Eddy, S. Griffiths-Jones, M. Marshall, M. Matzke, G. Ruvkun and T. Tuschl. A uniform system for microRNA annotation Rna Mar. 2003 277-279 9.

Findley, S. D., M. Tamanaha, N. J. Clegg and H. Ruohola-Baker. Maelstrom, a Drosophila spindle-class gene, encodes a protein that colocalizes with Vasa and RDE1/AGO1 homolog, Aubergine, in nuage Development Mar. 2003 859-871 130.

Hershberg, R., S. Altuvia and H. Margalit. A survey of small RNA-encoding genes in Escherichia coli Nucleic Acids Res Apr. 1, 2003 1813-1820 31.

Zhou, A., S. Scoggin, R. B. Gaynor and N. S. Williams. Identification of Nf-kappa B-regulated genes induced by TNFalpha utilizing expression profiling and RNA interference Oncogene Apr. 3, 2003 2054-2064 22.

Brennecke, J., D. R. Hipfner, a. Stark, R. B. Russell and S. M. Cohen. bantam encodes a developmentally regulated microRNA that controls cell proliferation and regulates the proapoptotic gene hid in Drosophila Cell Apr. 4, 2003 25-36 113.

Lim, L. P., N. C. Lau, E. G. Weinstein, A. Abdelhakim, S. Yekta, M. W. Rhoades, C. B. Burge and D. P. Bartel. The microRNAs of Caenorhabditis elegans Genes Dev Apr. 15, 2003 991-1008 17.

Xu, P., S. Y. Vernooy, M. Guo and B. A. Hay. The Drosophila microRNA Mir-14 suppresses cell death and is required for normal fat metabolism Curr Biol Apr. 29, 2003 790-795 13.

Xie, Z., K. D. Kasschau and J. C. Carrington. Negative feedback regulation of Dicer-Like1 in Arabidopsis by microRNA-guided mRNA degradation Curr Biol Apr. 29, 2003 784-789 13.

Masse, E., N. Majdalani and S. Gottesman. Regulatory roles for small RNAs in bacteria Curr. Opin Microbiol Apr. 2003 120-124 6.

Carmichael, G. G. Antisense starts making more sense Nat Bioctechnol Apr. 2003 371-372 21.

Yelin, R., D. Dahary, R. Sorek, E. Y. Levanon, O. Goldstein, A. Shoshan, A. Diber, S. Biton, Y. Tamir, R. Khosravi, S. Nemzer, E. Pinner, S. Walach, J. Bernstein, K. Savitsky and G. Rotman. Widespread occurrence of antisense transcription in the human genome.

Boutet, S., F. Vazquez, J. Liu, C. Beclin, M. Fagard, A. Gratias, J. B. Morel, P. Crete, X. Chen and H. Vaucheret. Arabidopsis HEN1: a genetic link between endogenous miRNA controlling development and siRNA controlling transgene silencing and virus resistance Curr Biol May13, 2003 843-848 13.

Ambros, V., R. C. Lee, A. Lavanway, P. T. Williams and D. Jewell. MicroRNAs and other tiny endogenous RNAs in C. elegans Curr Biol May 13, 2003 807-818 13.

Liang, X. S., J. Q. Lian, Y. X. Zhou, Q. H. Nie and C. Q. Hao. A small yeast RNA inhibits HCV IRES mediated translation and inhibits replication of poliovirus in vivo World J Gastroenterol May 2003 1008-1013 9.

Grad, Y., J. Aach, G. D. Hayes, B. J. Reinhart, G. M. Church, G. Ruvkun and J. Kim. Computational and experimental identification of C. elegans microRNAs Mol Cell May 2003 1253-1263 11.

Abrahante, J. E., A. L. Daul, M. Li, M. L. Volk, J. M. Tennessen, E. A. Miller and A. E. Rougvie. The Caenorhabditis elegans hunchback-like gene lin-57/hbl-1 controls developmental time and is regulated by microRNAs Dev Cell May 2003 625-637 4.

Lin, S. Y., S. M. Johnson, M. Abraham, M. C. Vella, A. Pasquinelli, C. Gamberi, E. Gottlieb and F. J. Slack. The C elegans hunchback homolog, hbl-1, controls temporal patterning and is a probable microRNA target Dev Cell May 2003 639-650 4.

Zamvil, S. S. and L. Steinman. Diverse targets for intervention during inflammatory and neurodegenerative phases of multiple sclerosis Neuron Jun. 5, 2003 685-688 38.

Ambros, V. MicroRNA pathways in flies and worms: growth, death, fat, stress, and timing Cell Jun. 13, 2003 673-676 113.

Moss, E. G. and L. Tang. Conservation of the heterochronic regulator Lin-28, its developmental expression and microRNA complementary sites Dev Biol Jun. 15, 2003 432-442 258.

Smalheiser, N. R. EST analyses predict the existence of a population of chimeric microRNA precursor-mRNA transcripts expressed in normal human and mouse tissues Genome Biol Epub 2003 Jun. 18, 2003 403 4.

Kawasaki, H. And K. Taira. Hes1 is a target of microRNA-23 during retinoic-acid-induced neuronal differentiation of NT2 cells Nature Jun. 19, 2003 838-842 423.

Lai, E. C., P. Tomancak, R. W. Williams and G. M. Rubin. Computational identification of Drosophila microRNA genes Genome Biol Epub 2003 Jun. 30, 2003 R42 4.

No author listed. Whither RNAi? Nat Cell Biol Jun. 2003 489-490 5.

Bartel, B. and D. P. Bartel. MicroRNAs: at the root of plant development? Plant Physiol Jun. 2003 709-717 132.

Dykxhoorn, D. M., C. D. Novina and P. A. Sharp. Killing the messenger: short RNAs that silence gene expression Nat Rev Mol Cell Biol Jun. 2003 457-467 4.

Saunders, L. R. and G. N. Barber. The dsRNA binding protein family: critical roles, diverse cellular functions FASEB J Jun. 2003 961-983 17.

Steinman, L. and S. Zamvil. Transcriptional analysis of targets in multiple sclerosis Nat Rev Immunol Jun. 2003 483-492 3.

Qi, Y. and B. Ding. Inhibition of cell growth and shoot development by a specific nucleotide sequence in a noncoding viroid RNA Plant Cell Jun. 2003 1360-1374 15.

Jackson, A. L., S. R. Bartz, J. Schelter, S. V. Kobayashi, J. Burchard, M. Mao, B. Li, G. Cavet and P. S. Linsley. Expression profiling reveals off-target gene regulation by RNAi Nat Biotechnol Jun. 2003 635-637 21.

Bashirullah, A., A. E. Pasquinelli, A. A. Kiger, N. Perrimon, G. Ruvkun and C. S. Thummel. Coordinate regulation of small temporal RNAs at the onset of Drosophila metamorphosis Dev Biol Jul. 1, 2003 1-8 259.

Sempere, L. F., N. S. Sokol, E. B. Dubrovsky, E. M. Berger and V. Ambros. Temporal regulation of microRNA expression in Drosophila melanogaster mediated by hormonal signals and broad-Complex gene activity Dev Biol Jul. 1, 2003 9-18 259.

Heetebrij, R. J., E. G. Talman, M. A. V Velzen, R. P. Van Gijlswijk, S. S. Snoeijers, M. Schalk, J. Wiegant, F. V D Rijke, R. M. Kerkhoven, A. K. Raap, H. J. Tanke, J. Reedijk and H. J. Houthoff. Platinum(II)-based coordination compounds as nucleic acid labeling reagents: synthesis, reactivity, and applications in hybridization assays Chembiochem Jul. 7, 2003 573-583 4.

Borodina, T. A., H. Lehrach and A. V. Soldatov. Ligation-based synthesis of oligonucleotides with block structure Anal Biochem Jul. 15, 2003 309-313 318.

Johnson, S. M., S. Y. Lin and F. J. Slack. The time of appearance of the C. elegans let-7 microRNA is transcriptionally controlled utilizing a temporal regulatory element in its promoter Dev Biol Jul. 15, 2003 364-379 259.

Carrington, J. C. and V. Ambros. Role of microRNAs in plant and animal development Science Jul. 18, 2003 336-338 301.

Smale, S. T. The establishment and maintenance of lymphocyte identity through gene silencing Nat Immunol Jul. 2003 607-615 4.

Bridge, A. J., S. Pebernard, A. Ducraux, A. L. Nicoulaz and R. Iggo. Induction of an interferon response by RNAi vectors in mammalian cells Nat Genet Jul. 2003 263-264 34.

Seitz, H., N. Youngson, S. P. Lin, S. Dalbert, M. Paulsen, J. P. Bachellerie, A. C. Ferguson-Smith and J. Cavaille. Imprinted microRNA genes transcribed antisense to a reciprocally imprinted retrotransposon-like gene Nat Genet Jul. 2003 261-262 34.

Zeng, Y., R. Yi and B. R. Cullen. MicroRNAs and small interfering RNAs can inhibit mRNA expression by similar mechanisms Proc Nat; Acad Sci U S A Aug. 19, 2003 9779-9784 100.

Schramke, V. and R. Allshire. Hairpin RNAs and retrotransposon LTRs effect RNAi and chromatin-based gene silencing Science Aug. 22, 2003 1069-1074 301.

Wiznerowicz, M. and D. Trono. Conditional suppression of cellular genes: lentivirus vector-mediated drug-inducible RNA interference J Virol Aug. 2003 8957-8961 77.

Lau, N. C. and D. P. Bartel. Censors of the genome Sci Am Aug. 2003 34-41 289.

Houbaviy, H. B., M. F. Murray and P. A. Sharp. Embryonic stem cell-specific MicroRNAs Dev Cell Aug. 2003 351-358 5.

Aravin, A. A., M. Lagos-Quintana, A. Yalcin, M. Zavolan, D. Marks, B. Snyder, T. Gaasterland, J. Meyer and T. Tuschl. The small RNA profile during Drosophila melanogaster development Dev Cell Aug. 2003 337-350 5.

McManus, M. T. MicroRNAs and cancer Semin Cancer Biol Aug. 2003 253-258 13.

Baner, J., A. Isaksson, E. Waldenstrom, J. Jarvius, U. Landegren and M. Nilsson. Parallel gene analysis with allele-specific padlock probes and tag microarrays Nucleic Acids Res Sep. 1, 2003 e103 31.

Boutla, A., C. Delidakis and M. Tabler. Developmental defects by antisense-mediated inactivation of micro-RNAs 2 and 13 in Drosophila and the identification of putative target genes Nucleic Acids Res Sep. 1, 2003 4973-4980 31.

Palatnik, J. F., E. Allen, X. Wu, C. Schommer, R. Schwab, J. C. Carrington and D. Weigel. Control of leaf morphogenesis by microRNAs Nature Sep. 18, 2003 257-263 425.

Klein, R. J. and S. R. Eddy. Rsearch: finding homologs of single structured RNA sequences BMC Bioinformatics Sep. 22, 2003 44 4.

Caudy, A. A., R. F. Ketting, S. M. Hammond, A. M. Denli, A. M. Bathoorn, B. B. Tops, J. M. Silva, M. M. Myers, G. J. Hannon and R.

H. Plasterk. A micrococcal nuclease homologue in RNAi effector complexes Nature Sep. 25, 2003 411-414 425.

Lee, Y., C. Ahn, J. Han, H. Choi, J. Kim, J. Yim, J. Lee, P. Provost, O. Radmark, S. Kim and V. N. Kim. The nuclear RNase III Drosha initiates microRNA processing Nature Sep. 25, 2003 415-419 425.

Sledz, C. A., M. Holko, M. J. De Veer, R. H. Silverman and B. R. Williams. Activation of the interferon system by short-interfering RNAs Nat Cell Biol Sep. 2003 834-839 5.

Bergmann, A. and M. E. Lane. HIDden targets of microRNAs for growth control Trends Biochem Sci Sep. 2003 461-463 28.

Khvorova, A., A. Reynolds and S. D. Jayasena. Functional siRNAs and miRNAs exhibit strand bias Cell Oct. 17, 2003 209-216 115.

Schwarz, D. S., G. Hutvagner, T. Du, Z. Xu, N. Aronin and P. D. Zamore. Asymmetry in the assembly of the RNAi enzyme complex Cell Oct. 17, 2003 199-208 115.

Abbott, A. L. Heterochronic genes Curr Biol Oct. 28, 2003 R824-825 13.

Hake, S. MicroRNAs: a role in plant development Curr Biol Oct. 28, 2003 R851-852 13.

Carthew, R. W. Making and breaking with nucleases and small RNAs Nat Struct Biol Oct. 2003 776-777 10.

Krichevsky, A. M., K. S. King, C. P. Donahue, K. Khrapko and K. S. Kosik. A microRNA array reveals extensive regulation of microRNAs during brain development Rna Oct. 2003 1274-1281 9.

Mattick, J. S. Challenging the dogma: the hidden layer of non-protein-coding RNAs in complex organisms Bioessays Oct. 2003 930-939 25.

Nelson, P., M. Kiriakidou, A. Sharma, E. Maniataki and Z. Mourelatos. The microRNA world: small is mighty Trends Biochem Sci Oct. 2003 534-540 28.

Michael, M. Z., O. C. Sm, N. G. Van Holst Pellekaan, G. P. Young and R. J. James. Reduced accumulation of specific microRNAs in colorectal neoplasia Mol Cancer Res Oct. 2003 882- 891 1.

Allinson, T. M., E. T. Parkin, A. J. Turner and N. M. Hooper. ADAMs family members as amyloid precursor protein alpha-secretases J Neurosci Res Nov. 1, 2003 342-352 74.

Kawasaki, H. and K. Taira. Retraction: Hes1 is a target of microRNA-23 during retinoic-acid-induced neuronal differentiation of NT2 cells Nature Nov. 6, 2003 100 426.

Saxena, S., Z. O. Jonsson and A. Dutta. Small RNAs with imperfect match to endogenous mRNA repress translation. Implications for off-target activity of small inhibitory RNA in mammalian cells J Biol Chem Nov. 7, 2003 44312-44319 278.

Basyuk, E., F. Suavet, A. Doglio, R. Bordonne and E. Bertrand. Human let-7 stem-loop precursors harbor features of RNase III cleavage products Nucleic Acids Res Nov. 15, 2003 6593-6597 31.

Stevenson, M. Dissecting HIV-1 through RNA interference Nat Rev Immunol Nov. 2003 851-858 3.

Wienholds, E., M. J. Koudijs, F. J. Van Eeden, E. Cuppen and R. H. Plasterk. The microRNA-producing enzyme Dicer1 is essential for zebrafish development Nat Genet Nov. 2003 217-218 35.

Gibbs, W. W. The unseen genome: gems among the junk Sci Am Nov. 2003 26-33 289.

Chang, J., P. Provost and J. M. Taylor. Resistance of human hepatitis delta virus RNAs to dicer activity J Virol Nov. 2003 11910-11917 77.

Wang, D., A. Urisman, Y. T. Liu, M. Springer, T. G. Ksiazek, D. D. Erdman, E. R. Mardis, M. Hickenbotham, V. Magrini, J. Eldred, J. P. Latreille, R. K. Wilson, D. Ganem and J. L. Derisi. Viral discovery and sequence recovery using DNA microarrays PLoS Biol Nov. 2003 E2 1.

Aukerman, M. J. and H. Sakai. Regulation of flowering time and floral organ identity by a MicroRNA and its APETALA2-like target genes Plant Cell Nov. 2003 2730-2741 15.

Finnegan, E. J. and M. A. Matzke. The small RNA world J Cell Sci Dec. 1, 2003 4689-4693 116.

Enright, A. J., B. John, U. Gaul, T. Tuschl, C. Sander and D. S. Marks. MicroRNA targets in *Drosophila* Genome Biol Epub Dec. 12, 2003 R1 5.

Rosok, O. and M. Sioud. Systematic identification of sense-antisense transcripts in mammalian cells Nat Biotechnol Jan (Epub Dec. 14, 2003) 2004 104-108 22.

Yi, R., Y. Qin, I. G. Macara and B. R. Cullen. Exportin-5 mediates the nuclear export of premicroRNAs and short hairpin RNAs Genes Dev Dec. 15, 2003 3011-3016 17.

Cao, X., W. Aufsatz, D. Zilberman, M. F. Mette, M. S. Huang, M. Matzke and S. E. Jacobsen. Role of the DRM and CMT3 methyltransferases in RNA-directed DNA methylation Curr Biol Dec. 16, 2003 2212-2217 13.

Ye, K., L. Malinina and D. J. Patel. Recognition of small interfering RNA by a viral suppressor of RNA silencing Nature Dec. 18, 2003 874-878 426.

Johnston, R. J. and O. Hobert. A microRNA controlling left/right neuronal asymmetry in *Caenorhabditis elegans* Nature Dec. 18, 2003 845-849 426.

Xayaphoummine, A., T. Bucher, F. Thalmann and H. Isambert. Prediction and statistics of pseudoknots in RNA structures using exactly clustered stochastic simulations Proc Natl Acad Sci U S A Dec. 23, 2003 15310-15315 100.

Lewis, B. P., I. H. Shih, M. W. Jones-Rhoades, D. P. Bartel and C. B. Burge. Prediction of mammalian microRNA targets Cell Dec. 26, 2003 787-798 115.

Robinson, W. H., P. J. Utz and L. Steinman. Genomic and proteomic analysis of multiple sclerosis. Opinion Curr Opin Immunol Dec. 2003 660-667 15.

Gibbs, W. W. The unseen genome: beyond DNA Sci Am Dec. 2003 106-113 289.

Stark, A., J. Brennecke, R. B. Russell and S. M. Cohen. Identification of *Drosophila* MicroRNA targets PLoS Biol Dec. 2003 E60 1.

Konforti, B. The news and you Nat Struct Biol 2003 147 10.

Stein, T. D. and J. A. Johnson. Genetic programming by the proteolytic fragments of the amyloid precursor protein: somewhere between confusion and clarity Rev Neurosci *no. date in pubmed* 2003 317-341 14.

Szymanski, M., M. Z. Barciszewska, M. Zywicki and J. Barciszewski. Noncoding RNA transcripts J Appl Genet *No. Datein Pubmed* 2003 1-19 44.

Griffiths-Jones, S. The microRNA Registry Nucleic Acids Res Jan. 1, 2004 D109-111 32.

Chen, C. Z., L. Li, H. F. Lodish and D. P. Bartel. MicroRNAs modulate hematopoietic lineage differentiation Science Jan. 2, 2004 83-86 303.

Kim, J., A. Krichevsky, Y. Grad, G. D. Hayes, K. S. Kosik, G. M. Church and G. Ruvkun. Identification of many microRNAs that copurify with polyribosomes in mammalian neurons Proc Natl Acad Sci U S A Jan. 6, 2004 360-365 101.

Ohno, M., E. A. Sametsky, L. H. Younkin, H. Oakley, S. G. Younkin, M. Citron, R. Vassar and J. F. Disterhoft. BACE1 deficiency rescues memory deficits and cholinergic dysfunction in a mouse model of Alzheimer's disease Neuron Jan. 8, 2004 27-33 41.

Vella, M. C., E. Y. Choi, S. Y. Lin, K. Reinert and F. J. Slack. The C. elegans microRNA let-7 binds to imperfect let-7 complementary sites from the lin-41 3'UTR Genes Dev Jan. 15, 2004 132-137.

Kao, S. C., A. M. Krichevsky, K. S. Kosik and L. H. Tsai. BACE1 suppression by RNA interference in primary cortical neurons J Biol Chem Jan. 16, 2004 1942-1949 279.

Hofacker, I. L., B. Priwitzer and P. F. Stadler. Prediction of locally stable RNA secondary structures for genome-wide surveys Bioinformatics Jan. 22, 2004 186-190 20.

Ruvkun, G., B. Wightman and I. Ha. The 20 years it took to recognize the importance of tiny RNAs Cell Jan. 23, 2004 S93-96, 92 p. following S96 116.

Bartel, D. P. MicroRNAs: genomics, biogenesis, mechanism, and function Cell Jan. 23, 2004 281-297 116.

Han, M. H., S. Goud, L. Song and N. Fedoroff. The Arabidopsis double-stranded RNA-binding protein HYL1 plays a role in microRNA-mediated gene regulation Proc Natl Acad Sci U S A Jan. 27, 2004 1093-1098 101.

Hartig, J. S., I. Grune, S. H. Najafi-Shoushtari and M. Famulok. Sequence-specific detection of MicroRNAs by signal-amplifying ribozymes J Am Chem Soc Jan. 28, 2004 722-723 126.

Nishitsuji, H., T. Ikeda, H. Miyoshi, T. Ohashi, M. Kannagi and T. Masuda. Expression of small hairpin RNA by lentivirus-based vector confers efficient and stable gene-suppression of HIV-1 on human cells including primary non-dividing cells Microbes Infect Jan. 2004 76-85 6.

Ota, T., Y. Suzuki, T. Nishikawa, T. Otsuki, T. Sugiyama, R. Irie, A., et al. Complete sequencing and characterization of 21,243 full-length human cDNAs Nat Genet Jan. 2004 40-45 36.

Colciaghi, F., E. Marcello, B. Borroni, M. Zimmermann, C. Caltagirone, F. Cattabeni, A. Padovani and M. Di Luca. Platelet App, Adam 10 and BACE alterations in the early stages of Alzheimer disease Neurology Feb. 10, 2004 498-501 62.

Boden, D., O. Pusch, R. Silbermann, F. Lee, L. Tucker and B. Ramratnam. Enhanced gene silencing of HIV-1 specific siRNA using microRNA designed hairpins Nucleic Acids Res Feb. 13, 2004 1154-1158 32.

Sempere, L. F., S. Freemantle, I. Pitha-Rowe, E. Moss, E. Dmitrovsky and V. Ambros. Expression profiling of mammalian microRNAs uncovers a subset of brain-expressed microRNAs with possible roles in murine and human neuronal differentiation Genome Biol Epub 2004 Feb. 16, 2004 R13 5.

Scacheri, P. C., O. Rozenblatt-Rosen, N. J. Caplen, T. G. Wolfsberg, L. Umayam, J. C. Lee, C. M. Hughes, K. S. Shanmugam, A. Bhattacharjee, M. Meyerson and F. S. Collins. Short interfering RNAs can induce unexpected and divergent changes in the levels of untargeted proteins in mammalian cells Proc Natl Acad Sci U S A Feb. 17, 2004 1892-1897 101.

Xie, Z., L. K. Johansen, A. M. Gustafson, K. D. Kasschau, A. D. Lellis, D. Zilberman, S. E. Jacobsen and J. C. Carrington. Genetic and functional diversification of small RNA pathways in plants PLoS Biol May (Epub Feb. 18, 2004) 2004 E104 2.

Cawley, S., S. Bekiranov, H. H. Ng, P. Kapranov, E. A. Sekinger, D. Kampa, A. Piccolboni, V. Sementchenko, J. Cheng, A. J. Williams, R. Wheeler, B. Wong, J. Drenkow, M. Yamanaka, S. Patel, S. Brubaker, H. Tammana, G. Helt, K. Struhl and T. R. Gingeras. Unbiased mapping of transcription factor binding sites along human chromosomes 21 and 22 points to widespread regulation of noncoding RNAs Cell Feb 20, 2004 499-509 116.

Dandekar, D. H., K. N. Ganesh and D. Mitra. HIV-1 Tat directly binds to NFkappaB enhancer sequence: role in viral and cellular gene expression Nucleic Acids Res Feb 23, 2004 1270-1278 32.

Hutvagner, G., M. J. Simard, C. C. Mello and P. D. Zamore. Sequence-specific inhibition of small RNA function PLoS Biol Apr. (Epub Feb. 24, 2004) 2004 E98 2.

Schmittgen, T. D., J. Jiang, Q. Liu and L. Yang. A high-throughput method to monitor the expression of microRNA precursors Nucleic Acids Res Feb. 25, 2004 e43 32.

Stremlau, M., C. M. Owens, M. J. Perron, M. Kiessling, P. Autissier and J. Sodroski. The cytoplasmic body component TRIM5alpha restricts HIV-1 infection in Old World monkeys Nature Feb. 26, 2004 848-853 427.

Bohnsack, M. T., K. Czaplinski and D. Gorlich. Exportin 5 is a RanGTP-dependent dsRNA-binding protein that mediates nuclear export of pre-miRNAs Rna Feb. 2004 185-191 10.

Demidov, V. V. and M. D. Frank-Kamenetskii. Two sides of the coin: affinity and specificity of nucleic acid interactions Trends Biochem Sci Feb. 2004 62-71 29.

Maquat, L. E. Nonsense-mediated mRNA decay: splicing, translation and mRNP dynamics Nat Rev Mol Cell Biol Feb. 2004 89-99 5.

Nijholt, I., N. Farchi, M. Kye, E. H. Sklan, S. Shoham, B. Verbeure, D. Owen, B. Hochner, J. Spiess, H. Soreq and T. Blank. Stress-induced alternative splicing of acetylcholinesterase results in enhanced fear memory and long-term potentiation Mol Psychiatry Feb. 2004 174-183 9.

Sengupta, P. Taking sides in the nervous system with miRNA Nat Neurosci Feb. 2004 100-102 7.

Zerhouni, B., J. A. Nelson and K. Saha. Isolation of CD4-independent primary human immunodeficiency virus type 1 isolates that are syncytium inducing and acutely cytopathic for CD8+ lymphocytes J Virol Feb. 2004 1243-1255 78.

Jin, P., D. C. Zarnescu, S. Ceman, M. Nakamoto, J. Mowrey, T. A. Jongens, D. L. Nelson, K. Moses and S. T. Warren. Biochemical and genetic interaction between the fragile X mental retardation protein and the microRNA pathway Nat Neurosci Feb. 2004 113-117 7.

Lai, E. C., C. Wiel and G. M. Rubin. Complementary miRNA pairs suggest a regulatory role for miRNA:miRNA duplexes Rna Feb. 2004 171-175 10.

Metzler, M., M. Wilda, K. Busch, S. Viehmann and A. Borkhardt. High expression of precursor microRNA-155/BIC RNA in children with Burkitt lymphoma Genes Chromosomes Cancer Feb. 2004 167-169 39.

Doench, J. G. and P. A. Sharp. Specificity of microRNA target selection in translational repression Genes Dev Mar. 1, 2004 504-511 18.

Liang, X. S., J. Q. Lian, Y. X. Zhou and M. B. Wan. Inhibitor RNA blocks the protein translation mediated by hepatitis C virus internal ribosome entry site in vivo World J Gastroenterol Mar. 1, 2004 664-667 10.

Calin, G. A., C. Sevignani, C. D. Dumitru, T. Hyslop, E. Noch, S. Yendamuri, M. Shimizu, S. Rattan, F. Bullrich, M. Negrini and C. M. Croce. Human microRNA genes are frequently located at fragile sites and genomic regions involved in cancers Proc Natl Acad Sci U S A Mar. 2, 2004 2999-3004 101.

Juarez, M. T., J. S. Kui, J. Thomas, B. A. Heller and M. C. Timmermans. microRNA-mediated repression of rolled leaf1 specifies maize leaf polarity Nature Mar. 4, 2004 84-88 428.

Kidner, C. A. And R. A. Martienssen. Spatially restricted microRNA directs leaf polarity through Argonaute1 Nature Mar. 4, 2004 81-84 428.

Zamore, P. D. Plant RNAi: How a viral silencing suppressor inactivates siRNA Curr Biol Mar. 9, 2004 R198-200 14.

Wang, J. F., H. Zhou, Y. Q. Chen, Q. J. Luo and L. H. Qu. Identification of 20 microRNAs from Oryza sativa Nucleic Acids Res Mar. 12, 2004 1688-1695 32.

Jack, T. Molecular and genetic mechanisms of floral control Plant Cell Epub 2004 Mar. 12, 2004 2004 S1-17 16 Suppl.

Roth, M. E., L. Feng, K. J. McConnell, P. J. Schaffer, C. E. Guerra, J. P. Affourtit, K. R. Piper, L. Guccione, J. Hariharan, M. J. Ford, S. W. Powell, H. Krishnaswamy, J. Lane, L. Guccione, G. Intrieri, J. S. Merkel, C. Perbost, A. Valerio, B. Zolla, C. D. Graham, J. Hnath, C. Michaelson, R. Wang, B. Ying, C. Halling, C. E. Parman, D. Raha, B. Orr, B. Jedrzkiewicz, J. Liao, A. Tevelev, M. J. Mattessich, D. M. Kranz, M. Lacey, J. C. Kaufman, J. Kim, D. R. Latimer and P. M. Lizardi. Expression profiling using a hexamer-based universal microarray Nat Biotechnol Apr. (Epub Mar. 14, 2004) 2004 418-426 22.

Rajewsky, N. and N. D. Socci. Computational identification of microRNA targets Dev Biol Mar. 15, 2004 529-535 267.

Winkler, W. C., A. Nahvi, A. Roth, J. A. Collins and R. R. Breaker. Control of gene expression by a natural metabolite-responsive ribozyme Nature Mar. 18, 2004 281-286 428.

Kuwabara, T., J. Hsieh, K. Nakashima, K. Taira and F. H. Gage. A small modulatory dsRNA specifies the fate of adult neural stem cells Cell Mar. 19, 2004 779-793 116.

Chen, X. A microRNA as a translational repressor of APETALA2 in *Arabidopsis* flower development Science Mar. 26, 2004 2022-2025 303.

Carmell, M. A. and G. J. Hannon. RNase III enzymes and the initiation of gene silencing Nat Struct Mol Biol Mar. 2004 214-218 11.

Davidson, B. L. and H. L. Paulson. Molecular medicine for the brain: silencing of disease genes with RNA interference Lancet Neurol Mar. 2004 145-149 3.

Kawasaki, H., R. Wadhwa and K. Taira. World of small RNAs: from ribozymes to siRNA and miRNA Differentiation Mar. 2004 58-64 72.

Meister, G., M. Landthaler, Y. Dorsett and T. Tuschl. Sequence-specific inhibition of microRNA- and siRNA-induced RNA silencing Rna Mar. 2004 544-550 10.

Nelson, P. T., A. G. Hatzigeorgiou and Z. Mourelatos. miRNP:mRNA association in polyribosomes in a human neuronal cell line Rna Mar. 2004 387-394 10.

Floyd, S. K. and J. L. Bowman. Gene regulation: ancient microRNA target sequences in plants Nature Apr. 1, 2004 485-486 428.

Dorsett, Y. and T. Tuschl. siRNAs: applications in functional genomics and potential as therapeutics Nat Rev Drug Discov Apr. 2004 318-329 3.

Mallory, A. C. and H. Vaucheret. MicroRNAs: something important between the genes Curr Opin Plant Biol Apr. 2004 120-125 7.

Ogita, S., H. Uefuji, M. Morimoto and H. Sano. Application of RNAi to confirm theobromine as the major intermediate for caffeine biosynthesis in coffee plants with potential for construction of decaffeinated varieties Plant Mol Biol Apr. 2004 931-941 54.

Storz, G., J. A. Opdyke and A. Zhang. Controlling mRNA stability and translation with small, noncoding RNAs Curr Opin Microbiol Apr. 2004 140-144 7.

Kim, V. N. MicroRNA precursors in motion: exportin-5 mediates their nuclear export Trends Cell Biol Apr. 2004 156-159 14.

Jabri, E. RISCy business Nat Struct Mol Biol Apr. 2004 300 11.

Nakahara, K. and R. W. Carthew. Expanding roles for miRNAs and siRNAs in cell regulation Curr Opin Cell Biol Apr. 2004 127-133 16.

Ambinder, R.F. et al. "Epstein-Barr virus genome B95-8." XP002500226. Retrieved from EBI Database accession No. ADN12161. Database EMBL Jun. 17, 2004.

"Human herpesvirus 4 complete wild type genome." XP002500227. Retrieved from EBI Database accession No. AJ507799. Abstract. Database EMBL Oct. 9, 2002.

European Search Report for European Pat. App. No. 05774516.8, mailed by European Patent Office on Nov. 27, 2008.

\* cited by examiner

FIG. 2A

5'UTR SEQUENCE (5' TO 3') OF HIV-1 (U5-R)

GGTCTCTCTGGTTAGACCAGATCTGAGCCTGGGAGCTCTCTGGCTAACT
AGGGAACCCACTGCTTAAGCCTCAATAAAGCTTGCCTTGAGTGCTTCAAGTA
GTGTGTGCCCGTCTGTTGTGTGACTCTGGTAACTAGAGATCCCTCAGACCCTT
TTAGTCAGTGTGGAAAATCTCTAGCAGTGGCGCCCGAACAGGGACCTGAAAG
CGAAAGGGAAACCAGAGGAGCTCTCTCGACGCAGGACTCGGCTTGCTGAA
GCGCGCACG<u>GCAAGAGGCGAGGGGCG</u>GCGACTGGTGAGTACGCCAAAAA
TTTTGACTAGCGGAGGCTAGAAGGAGAGAG

FIG. 2B

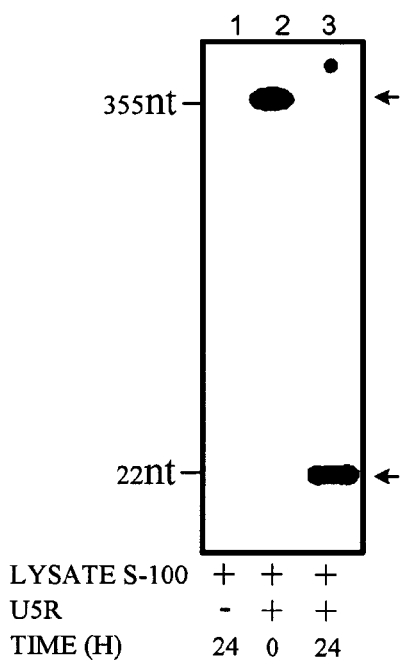

FIG. 2C

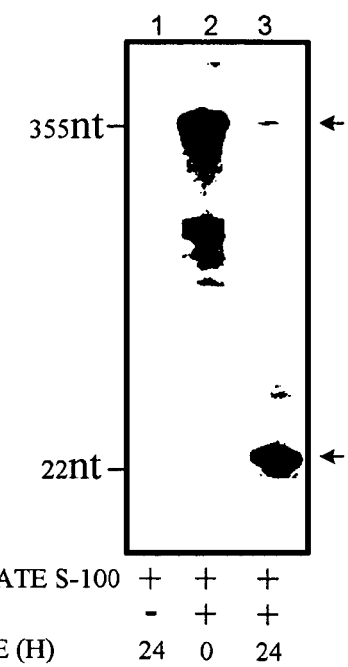

Fig 2E

TRANSCRIPT SEQUENCE (5' TO 3'):

TGGGAAGCCCTCAAATATTGGTGG
AATCTCCTACAGTATTGGAGTCAG
GAACTAAAGAATAGTGCTGTTAGC
TTGCTCAATGCCACAGCCATAGCA
GTAGCTGAGGGGACAGATAGGGTT
ATAGAAGTAGTACAAGGAGCTTGT
AGAGCTATTCGCCACATACCTAGA
AGAATAAGACAGGGCTTGGAAAGG
ATTTTGCT

GAM RNA:
TGAGGGGACAGATAGGGTTATAGA

200nt —
22nt —

| | 1 | 2 |
|---|---|---|
| LYSATE S-100 | + | + |
| TRANSCRIPT | + | + |
| TIME (H) | 0 | 24 |

Fig 2D

TRANSCRIPT SEQUENCE (5' TO 3'):

ACAGGGCTGCTATTAACAAGAGAT
GGTGGTAATAGCAACAATGAGTCC
GAGATCTTCAGACCTGGAGGAGGA
GATATGAGGGACAATTGGAGAAGT
GAATTATATAAATATAAAGTAGTA
AAAATTGAACCATTAGGAGTAGCA
CCCACCAAGGCAAAGAGAA

GAM RNA:
TGAGTCCGAGATCTTCAGACCTGG

163nt —
22nt —

| | 1 | 2 |
|---|---|---|
| LYSATE S-100 | + | + |
| TRANSCRIPT | + | + |
| TIME (H) | 0 | 24 |

VIRAL AND VIRAL ASSOCIATED MIRNAS AND USES THEREOF

CROSS REFERENCE TO RELATED APPLICATIONS

The present application is a continuation of International Application No. PCT/IB2005/002352, filed May 26, 2005, which is a continuation-in-part of U.S. patent application Ser. No. 10/709,739, filed May 26, 2004 and which claims the benefit of U.S. Provisional Application No. 60/522,459, filed Oct. 4, 2004, U.S. Provisional Application No. 60/665,094, filed Mar. 25, 2005, U.S. Provisional Application No. 60/522,450, filed Oct. 3, 2004, and U.S. Provisional Application No. 60/522,451, filed Oct. 3, 2004, each of which is incorporated herein by reference.

FIELD OF THE INVENTION

The invention relates in general to viral microRNA molecules and to a group of human microRNA molecules associated with viral infections, as well as various nucleic acid molecules relating thereto or derived therefrom.

BACKGROUND OF THE INVENTION

MicroRNAs (miRNAs) are short RNA oligonucleotides of approximately 22 nucleotides that are involved in gene regulation. MicroRNAs regulate gene expression by targeting miRNAs for cleavage or translational repression. Although miRNAs are present in a wide range of species including *C. elegans, Drosophila* and humans, they have only recently been identified. More importantly, the role of miRNAs in the development and progression of disease has only recently become appreciated.

As a result of their small size, miRNAs have been difficult to identify using standard methodologies. A limited number of miRNAs have been identified by extracting large quantities of RNA. MiRNAs have also been identified that contribute to the presentation of visibly discernable phenotypes. Expression array data shows that miRNAs are expressed in different developmental stages or in different tissues. The restriction of miRNAs to certain tissues or at limited developmental stages indicates that the miRNAs identified to date are likely only a small fraction of the total miRNAs.

Computational approaches have recently been developed to identify the remainder of miRNAs in the genome. Tools such as MiRscan and MiRseeker have identified miRNAs that were later experimentally confirmed. Based on these computational tools, it has been estimated that the human genome contains 200-255 miRNA genes. These estimates are based on an assumption, however, that the miRNAs remaining to be identified will have the same properties as those miRNAs already identified. Based on the fundamental importance of miRNAs in mammalian biology and disease, the art needs to identify unknown miRNAs. The present invention satisfies this need and provides a significant number of miRNAs and uses therefore. To date, no viral miRNAs have been detected.

SUMMARY OF THE INVENTION

The present invention is related to an isolated nucleic acid comprising a sequence of a pri-miRNA, pre-miRNA, miRNA, miRNA*, anti-miRNA, or a miRNA binding site, or a variant thereof. The nucleic acid may comprise SEQS: 4097721-4204913; the sequence of a precursor referred to in Table 1, 11-12 or 21-23; SEQS: 1-1142416 or 4204914-4204915; the sequence of a miRNA referred to in Table 1, 13-14 or 21-23; SEQS: 1142417-4097720; the sequence of a target gene binding site referred to in Tables 4, 10 or 15-16; a complement thereof; or a sequence comprising at least 12 contiguous nucleotides at least 70% identical thereto. The isolated nucleic acid may be from 5-250 nucleotides in length.

The present invention is also related to a probe comprising the nucleic acid. The probe may comprise at least 8-22 contiguous nucleotides complementary to SEQS: 1-1142416 or 4204914-4204915, a miRNA referred to in Table 1, 13-14 or 21-23, or a variant thereof. The probe may also comprise at least 8-22 contiguous nucleotides complementary to a human miRNA differentially expressed in viral infection, or variant thereof.

The present invention is also related to a plurality of the probes. The plurality of probes may comprise at least ten of the probes. The plurality of probes may also comprise at least 100 of the probes. The present invention is also related to a composition comprising a probe or plurality of probes. The present invention is also related to a biochip comprising a solid substrate, said substrate comprising a plurality of the probes. Each of the probes may be attached to the substrate at a spatially defined address. The biochip may comprise probes that are complementary to a viral miRNA. The biochip may also comprise probes that are complementary to a human miRNA characterized by expression during viral infection.

The present invention is also related to a method of detecting differential expression of a disease-associated miRNA. A biological sample may be provided and the level of a nucleic acid measured that is at least 70% identical to SEQS: 1-1142416 or 4204914-4204915; the sequence of a miRNA referred to in Table 1, 13-14 and 21-23; or a variant thereof. A difference in the level of the nucleic acid compared to a control is indicative of differential expression.

The present invention is also related to a method of identifying a compound that modulates a pathological condition. A cell may be provided that is capable of expressing a nucleic acid at least 70% identical to SEQS: 1-1142416; the sequence of a miRNA referred to in Table 1, 13-14 and 21-23; or a variant thereof. The cell may be contacted with a candidate modulator and then measuring the level of expression of the nucleic acid. A difference in the level of the nucleic acid compared to a control identifies the compound as a modulator of a pathological condition associated with the nucleic acid.

The present invention is also related to a method of inhibiting expression of a target gene in a cell. Into the cell, a nucleic acid may be introduced in an amount sufficient to inhibit expression of the target gene. The target gene may comprise a binding site substantially identical to a binding site referred to in Tables 4, 10 or 15-16, or a variant thereof. The nucleic acid may comprise a portion of SEQS: 1-1142416 or 4204914-4204915; the sequence of a miRNA referred to in Table 1, 13-14 or 21-23; or a variant thereof. Expression of the target gene may be inhibited in vitro or in vivo.

The present invention is also related to a method of increasing expression of a target gene in a cell. Into the cell, a nucleic acid may be introduced in an amount sufficient to increase expression of the target gene. The target gene may comprise a binding site substantially identical to a binding site referred to in Tables 4, 10 or 15-16, or a variant thereof. A portion of the nucleic acid may be substantially complementary to SEQS: 1-1142416 or 4204914-4204915; the sequence of a miRNA referred to in Table 1, 13-14 or 21-23; or a variant thereof. Expression of the target gene may be inhibited in vitro or in vivo. Expression of the target gene may be increased in vitro or in vivo.

The present invention is also related to a method of treating a patient with a disorder set forth on Table 6 comprising administering to a patient in need thereof a nucleic acid comprising a sequence of SEQS: 1-760616; a sequence set forth on Table 10; a sequence set forth on Table 17; or a variant thereof.

The present invention is also related to a method of treating a patient with a viral infection or a condition associated with a viral infection comprising administering to a patient in need thereof a nucleic acid, wherein a portion of the nucleic acid is substantially complementary to SEQ ID NOS: 1-1142416 or 4204914-4204915; the sequence of a miRNA referred to in Table 1, 13-14, or 21-23; or a variant thereof.

BRIEF DESCRIPTION OF SEQUENCE LISTING AND TABLES

Reference is made to the appendix submitted herewith. The appendix contains the following: Patent45 U.S. Ser. No. 11/511,035 Sequence Listing January 2008 Amended 01.tx t (20,000 KB); Patent45 U.S. Ser. No. 11/511,035 Sequence Listing January 2008 Amended 02.tx t (20,001 KB), Patent45 U.S. Ser. No. 11/511,035 Sequence Listing January 2008 Amended 03.tx t (20,001 KB); Patent45 U.S. Ser. No. 11/511, 035 Sequence Listing January 2008 Amended 04.tx t (20,000 KB); Patent45 U.S. Ser. No. 11/511,035 Sequence Listing January 2008 Amended 05.tx t (20,001 KB); and Patent45 U.S. Ser. No. 11/511,035 Sequence Listing January 2008 Amended 06.tx t (16,700 KB), which were all created on Jan. 8, 2008 and are altogether a sequence listing in accordance with 37 C.F.R. §§1.821-1.825, the contents of which are incorporated by reference herein.

Reference is made to the tables submitted in electronic form herewith. The tables consist of the following: "Table1.txt" (4 KB), "Table2.txt" (2 KB), "Table3.txt" (1 KB), "Table4.txt" (244 KB), "Table5.txt" (1 KB), "Table6.txt" (1 KB), "Table7.txt" (5 KB), "Table8.txt" (190 KB), "Table9.txt" (1 KB), "Table10.txt" (2 KB), which were all created on Sep. 19, 2008, the contents of all of which are incorporated by reference herein.

otide different from the miRNA presented in FIG. 2B. FIGS. 2B and 2C depict Northern blot analysis of miRNA oligonucleotides that are present in U5R, hybridized with predicted mature miRNA probes. The upper arrow indicates the molecular size of the entire 355 nt U5R transcript. The predicted molecular sizes of the two GAM RNAs are 22 nt and 17 nt, respectively. The lower arrow indicates the 22 nt molecular marker. Lanes: 1—Hela lysate; 2—U5R transcript in HeLa Lysate without incubation; and 3—U5R transcript incubated for 24 hours with Hela lysate. FIGS. 2D and 2E present partial transcripts of HIV1 RNA (SEQ ID NOS: 547374 and 547375) reacted with predicted mature HIV1 miRNA probes (SEQ ID NOS: 547376 and 547377). In each figure, the experimental transcript sequence is shown, and the predicted mature miRNA is underlined. Northern blot analyses of miRNA precursors are presented. It is demonstrated that one miRNA precursor transcript is 163 nt and the other miRNA precursor transcript is 200 nt. The predicted molecular sizes of mature miRNA are both 24 nt. The 22 nt molecular marker is indicated. Lanes: 1—Transcript in HeLa Lysate without incubation and 2—Transcript incubated for 24 hours with HeLa lysate. arrow indicates the 22 nt molecular marker. Lanes: 1—Hela lysate; 2—U5R transcript in HeLa Lysate without incubation; and 3—U5R transcript incubated for 24 hours with Hela lysate. FIGS. 2D and 2E present partial transcripts of HIV1 RNA (SEQ ID NOS: 547374 and 547375) reacted with predicted mature HIV1 miRNA probes (SEQ ID NOS: 547376 and 547377). In each figure, the experimental transcript sequence is shown, and the predicted mature miRNA is underlined. Northern blot analyses of miRNA precursors are presented. It is demonstrated that one miRNA precursor transcript is 163 nt and the other miRNA precursor transcript is 200 nt. The predicted molecular sizes of mature miRNA are both 24 nt. The 22 nt molecular marker is indicated. Lanes: 1—Transcript in HeLa Lysate without incubation and 2—Transcript incubated for 24 hours with HeLa lysate.

FIG. 3 shows the results of a Northern Blot. The expression profile of GAM506333 and GAM506336 in EBV-infected (B95/8 EBV) and non-infected (PBMC) cells are presented. The expression of these miRNAs was demonstrated on a miRNA microarray hybridized with RNA from B-95/8 cell

LENGTHY TABLES

The patent contains a lengthy table section. A copy of the table is available in electronic form from the USPTO web site (http://seqdata.uspto.gov/?pageRequest=docDetail&DocID=US07795419B2). An electronic copy of the table will also be available from the USPTO upon request and payment of the fee set forth in 37 CFR 1.19(b)(3).

BRIEF DESCRIPTION OF THE DRAWINGS

FIG. 2A shows the 5'UTR of HIV1 (U5R)(SEQ ID NO: 547373) containing two predicted miRNAs in bold. The mature miRNAs are underlined, one closer to the 5' end (FIG. 2B) and the second closer to the 3' end (FIG. 2C). The 5'-most miRNA matches the known HIV1 RNA structure named TAR to which the TAT protein binds (Nature 1987. 330:489-93). A similar miRNA (GAM NAME 506033) was also lit on the chip. This miRNA probe was designed based on the sequence of T-tropic HIV-1 (LAV-1), Subtype B, which is one nuclelines infected with EBV. Probes against these validated miRNA predictions were hybridized with total RNA on a Northern blot. Northern blots confirmed high expression of these two miRNAs in the infected cells on the microarray.

DETAILED DESCRIPTION

Figure 1:
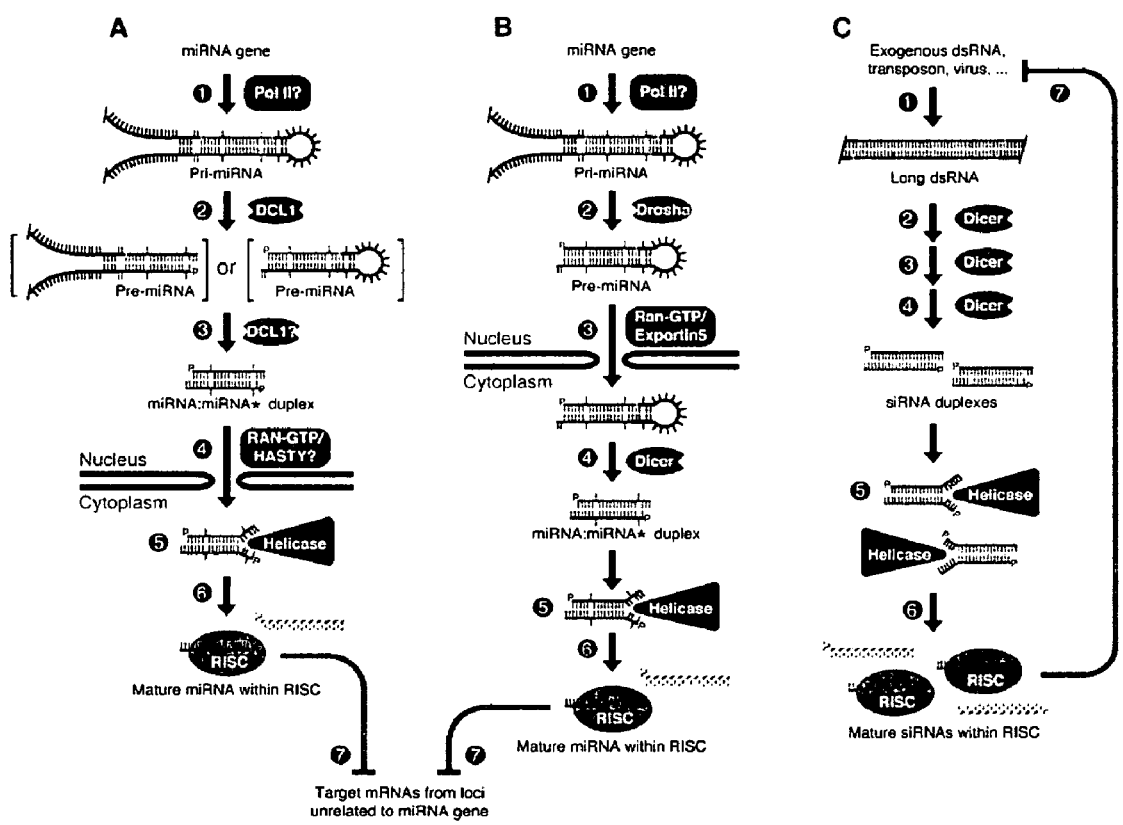
FIG. 1 demonstrates a model of maturation for miRNAs.

The present invention provides nucleotide sequences of viral and viral-associated miRNAs, precursors thereto, targets thereof and related sequences. Such nucleic acids are useful for diagnostic purposes, and also for modifying target gene expression. Other aspects of the invention will become apparent to the skilled artisan by the following description of the invention.

1. Definitions

Before the present compounds, products and compositions and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise. It must further be noted that the terms "and" and "or" may encompass both conjunctive and disjunctive meaning unless the context clearly dictates otherwise.

"Animal" as used herein may mean fish, amphibians, reptiles, birds, and mammals, such as mice, rats, rabbits, goats, cats, dogs, cows, apes and humans.

"Attached" or "immobilized" as used herein to refer to a probe and a solid support may mean that the binding between the probe and the solid support is sufficient to be stable under conditions of binding, washing, analysis, and removal. The binding may be covalent or non-covalent. Covalent bonds may be formed directly between the probe and the solid support or may be formed by a cross linker or by inclusion of a specific reactive group on either the solid support or the probe or both molecules. Non-covalent binding may be one or more of electrostatic, hydrophilic, and hydrophobic interactions. Included in non-covalent binding is the covalent attachment of a molecule, such as streptavidin, to the support and the non-covalent binding of a biotinylated probe to the streptavidin. Immobilization may also involve a combination of covalent and non-covalent interactions.

"Biological sample" as used herein may mean a sample of biological tissue or fluid that comprises nucleic acids. Such samples include, but are not limited to, tissue isolated from animals. Biological samples may also include sections of tissues such as biopsy and autopsy samples, frozen sections taken for histologic purposes, blood, plasma, serum, sputum, stool, tears, mucus, hair, and skin. Biological samples also include explants and primary and/or transformed cell cultures derived from patient tissues. A biological sample may be provided by removing a sample of cells from an animal, but can also be accomplished by using previously isolated cells (e.g., isolated by another person, at another time, and/or for another purpose), or by performing the methods of the invention in vivo. Archival tissues, such as those having treatment or outcome history, may also be used.

"Complement" or "complementary" as used herein may mean Watson-Crick or Hoogsteen base pairing between nucleotides or nucleotide analogs of nucleic acid molecules.

"Differential expression" may mean qualitative or quantitative differences in the temporal and/or cellular gene expression patterns within and among cells and tissue. Thus, a differentially expressed gene can qualitatively have its expression altered, including an activation or inactivation, in, e.g., normal versus disease tissue. Genes may be turned on or turned off in a particular state, relative to another state thus permitting comparison of two or more states. A qualitatively regulated gene will exhibit an expression pattern within a state or cell type which may be detectable by standard techniques. Some genes will be expressed in one state or cell type, but not in both. Alternatively, the difference in expression may be quantitative, e.g., in that expression is modulated, either up-regulated, resulting in an increased amount of transcript, or down-regulated, resulting in a decreased amount of transcript. The degree to which expression differs need only be large enough to quantify via standard characterization techniques such as expression arrays, quantitative reverse transcriptase PCR, northern analysis, and RNase protection.

"Gene" used herein may be a genomic gene comprising transcriptional and/or translational regulatory sequences and/or a coding region and/or non-translated sequences (e.g., introns, 5'- and 3'-untranslated sequences). The coding region of a gene may be a nucleotide sequence coding for an amino acid sequence or a functional RNA, such as tRNA, rRNA, catalytic RNA, siRNA, miRNA and antisense RNA. A gene may also be an miRNA or cDNA corresponding to the coding regions (e.g., exons and miRNA) optionally comprising 5'- or 3'-untranslated sequences linked thereto. A gene may also be an amplified nucleic acid molecule produced in vitro comprising all or a part of the coding region and/or 5'- or 3'-untranslated sequences linked thereto.

"Host cell" used herein may be a naturally occurring cell or a transformed cell that contains a vector and supports the replication of the vector. Host cells may be cultured cells, explants, cells in vivo, and the like. Host cells may be prokaryotic cells such as E. coli, or eukaryotic cells such as yeast, insect, amphibian, or mammalian cells, such as CHO, HeLa.

"Identical" or "identity" as used herein in the context of two or more nucleic acids or polypeptide sequences, may mean that the sequences have a specified percentage of nucleotides or amino acids that are the same over a specified region. The percentage may be calculated by comparing optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces staggered end and the specified region of comparison includes only a single sequence, the residues of single sequence are included in the denominator but not the numerator of the calculation. When comparing DNA and RNA, thymine (T) and uracil (U) are considered equivalent. Identity may be performed manually or by using computer sequence algorithm such as BLAST or BLAST 2.0.

"Inhibit" as used herein may mean prevent, suppress, repress, reduce or eliminate.

"Label" as used herein may mean a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and other entities which can be made detectable. A label may be incorporated into nucleic acids and proteins at any position.

"Nucleic acid" or "oligonucleotide" or "polynucleotide" used herein may mean at least two nucleotides covalently linked together. As will be appreciated by those in the art, the depiction of a single strand also defines the sequence of the complementary strand. Thus, a nucleic acid also encompasses the complementary strand of a depicted single strand. As will also be appreciated by those in the art, many variants of a nucleic acid may be used for the same purpose as a given nucleic acid. Thus, a nucleic acid also encompasses substantially identical nucleic acids and complements thereof. As will also be appreciated by those in the art, a single strand provides a probe for a probe that may hybridize to the target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

A nucleic acid will generally contain phosphodiester bonds, although nucleic acid analogs may be included that may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference. Nucleic acids containing one or more non-naturally occurring or modified nucleotides are also included within one definition of nucleic acids. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e.g. 7-deaza-adenosine; O- and N-alkylated nucleotides, e.g. N6-methyl adenosine are suitable. The 2'-OH-group may be replaced by a group selected from H, OR, R, halo, SH, SR, $NH_2$, NHR, $NR_2$ or CN, wherein R is $C_1$-$C_6$ alkyl, alkenyl or alkynyl and halo is F, Cl, Br or I. Modifications of the ribose-phosphate backbone may be done for a variety of reasons, e.g., to increase the stability and half-life of such molecules in physiological environments or as probes on a biochip. Mixtures of naturally occurring nucleic acids and analogs may be made; alternatively, mixtures of different nucleic acid analogs, and mixtures of naturally occurring nucleic acids and analogs may be made.

"Operably linked" used herein may mean that expression of a gene is under the control of a promoter with which it is spatially connected. A promoter may be positioned 5' (upstream) or 3' (downstream) of the gene under its control. The distance between the promoter and the gene may be approximately the same as the distance between that promoter and the gene it controls in the gene from which the promoter is derived. As is known in the art, variation in this distance can be accommodated without loss of promoter function.

"Probe" as used herein may mean an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence. A probe may be single stranded or partially single and partially double stranded. The strandedness of the probe is dictated by the structure, composition, and properties of the target sequence. Probes may be directly labeled or indirectly labeled such as with biotin to which a streptavidin complex may later bind.

"Promoter" as used herein may mean a synthetic or naturally-derived molecule which is capable of conferring, activating or enhancing expression of a nucleic acid in a cell. A promoter may comprise one or more specific regulatory elements to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Selectable marker" used herein may mean any gene which confers a phenotype on a cell in which it is expressed to facilitate the identification and/or selection of cells which are transfected or transformed with a genetic construct. Representative examples of selectable markers include the ampicillin-resistance gene ($Amp^r$), tetracycline-resistance gene ($Tc^r$), bacterial kanamycin-resistance gene ($Kan^r$), zeocin resistance gene, the AURI-C gene which confers resistance to the antibiotic aureobasidin A, phosphinothricin-resistance gene, neomycin phosphotransferase gene (nptII), hygromycin-resistance gene, beta-glucuronidase (GUS) gene, chloramphenicol acetyltransferase (CAT) gene, green fluorescent protein-encoding gene and luciferase gene.

"Stringent hybridization conditions" used herein may mean conditions under which a first nucleic acid sequence (e.g., probe) will hybridize to a second nucleic acid sequence (e.g., target), such as in a complex mixture of nucleic acids, but to no other sequences. Stringent conditions are sequence-dependent and will be different in different circumstances. Generally, stringent conditions are selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, typically about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

"Substantially complementary" used herein may mean that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50 or more nucleotides, or that the two sequences hybridize under stringent hybridization conditions.

"Substantially identical" used herein may mean that a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50 or more nucleotides or amino acids, or with respect to nucleic acids, if the first sequence is substantially complementary to the complement of the second sequence.

"Target" as used herein may mean a polynucleotide that may be bound by one or more probes under stringent hybridization conditions.

"Terminator" used herein may mean a sequence at the end of a transcriptional unit which signals termination of transcription. A terminator may be a 3'-non-translated DNA sequence containing a polyadenylation signal, which may facilitate the addition of polyadenylate sequences to the 3'-end of a primary transcript. A terminator may be derived from sources including viral, bacterial, fungal, plants, insects, and animals. Representative examples of terminators include the SV40 polyadenylation signal, HSV TK polyadenylation signal, CYC1 terminator, ADH terminator, SPA terminator, nopaline synthase (NOS) gene terminator of *Agrobacterium tumefaciens*, the terminator of the Cauliflower mosaic virus (CaMV) 35S gene, the zein gene terminator from *Zea mays*, the Rubisco small subunit gene (SSU) gene terminator sequences, subclover stunt virus (SCSV) gene sequence terminators, rho-independent *E. coli* terminators, and the lacZ alpha terminator.

"Treat" or "treating" used herein when referring to protection of an animal from a condition, means preventing, suppressing, repressing, or eliminating the condition. Preventing the condition involves administering a composition of the present invention to an animal prior to onset of the condition. Suppressing the condition involves administering a composition of the present invention to an animal after induction of the condition but before its clinical appearance. Repressing the condition involves administering a composition of the present invention to an animal after clinical appearance of the condition such that the condition is reduced or prevented from worsening. Elimination of the condition involves administering a composition of the present invention to an animal after clinical appearance of the condition such that the animal no longer suffers from the condition.

"Vector" used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

2. MicroRNA

While not being bound by theory, the current model for the maturation of mammalian miRNAs is shown in FIG. 1. A gene coding for a miRNA may be transcribed leading to production of an miRNA precursor known as the pri-miRNA. The pri-miRNA may be part of a polycistronic RNA comprising multiple pri-miRNAs. The pri-miRNA may form a hairpin with a stem and loop. As indicated on FIG. 1, the stem may comprise mismatched bases.

The hairpin structure of the pri-miRNA may be recognized by Drosha, which is an RNase III endonuclease. Drosha may recognize terminal loops in the pri-miRNA and cleave approximately two helical turns into the stem to produce a 60-70 nt precursor known as the pre-miRNA. Drosha may cleave the pri-miRNA with a staggered cut typical of RNase III endonucleases yielding a pre-miRNA stem loop with a 5' phosphate and ~2 nucleotide 3' overhang. Approximately one helical turn of stem (~10 nucleotides) extending beyond the Drosha cleavage site may be essential for efficient processing. The pre-miRNA may then be actively transported from the nucleus to the cytoplasm by Ran-GTP and the export receptor Ex-portin-5.

The pre-miRNA may be recognized by Dicer, which is also an RNase III endonuclease. Dicer may recognize the double-stranded stem of the pre-miRNA. Dicer may also recognize the 5' phosphate and 3' overhang at the base of the stem loop. Dicer may cleave off the terminal loop two helical turns away from the base of the stem loop leaving an additional 5' phosphate and ~2 nucleotide 3' overhang. The resulting siRNA-like duplex, which may comprise mismatches, comprises the mature miRNA and a similar-sized fragment known as the miRNA*. The miRNA and miRNA* may be derived from opposing arms of the pri-miRNA and pre-miRNA. miRNA* sequences may be found in libraries of cloned miRNAs but typically at lower frequency than the miRNAs.

Although initially present as a double-stranded species with miRNA*, the miRNA may eventually become incorporated as single-stranded RNAs into a ribonucleoprotein complex known as the RNA-induced silencing complex (RISC). Various proteins can form the RISC, which can lead to variability in specificity for miRNA/miRNA* duplexes, binding site of the target gene, activity of miRNA (repress or activate), which strand of the miRNA/miRNA* duplex is loaded in to the RISC.

When the miRNA strand of the miRNA:miRNA* duplex is loaded into the RISC, the miRNA* may be removed and degraded. The strand of the miRNA:miRNA* duplex that is loaded into the RISC may be the strand whose 5' end is less tightly paired. In cases where both ends of the miRNA:miRNA* have roughly equivalent 5' pairing, both miRNA and miRNA* may have gene silencing activity.

The RISC may identify target nucleic acids based on high levels of complementarity between the miRNA and the miRNA, especially by nucleotides 2-8 of the miRNA. Only one case has been reported in animals where the interaction between the miRNA and its target was along the entire length of the miRNA. This was shown for mir-196 and Hox B8 and it was further shown that mir-196 mediates the cleavage of the Hox B8 miRNA (Yekta et al 2004, Science 304-594). Otherwise, such interactions are known only in plants (Bartel & Bartel 2003, Plant Physiol 132-709).

A number of studies have looked at the base-pairing requirement between miRNA and its miRNA target for achieving efficient inhibition of translation (reviewed by Bartel 2004, Cell 116-281). In mammalian cells, the first 8 nucleotides of the miRNA may be important (Doench & Sharp 2004 GenesDev 2004-504). However, other parts of the microRNA may also participate in miRNA binding. Moreover, sufficient base pairing at the 3' can compensate for insufficient pairing at the 5' (Brennecke at al, 2005 PLoS 3-e85). Computation studies, analyzing miRNA binding on whole genomes have suggested a specific role for bases 2-7 at the 5' of the miRNA in target binding but the role of the first nucleotide, found usually to be "A" was also recognized (Lewis et at 2005 Cell 120-15). Similarly, nucleotides 1-7 or 2-8 were used to identify and validate targets by Krek et al (2005, Nat Genet 37-495).

The target sites in the miRNA may be in the 5' UTR, the 3' UTR or in the coding region. Interestingly, multiple miRNAs may regulate the same miRNA target by recognizing the same or multiple sites. The presence of multiple miRNA complementarity sites in most genetically identified targets may indicate that the cooperative action of multiple RISCs provides the most efficient translational inhibition.

MiRNAs may direct the RISC to downregulate gene expression by either of two mechanisms: miRNA cleavage or translational repression. The miRNA may specify cleavage of the miRNA if the miRNA has a certain degree of complementarity to the miRNA. When a miRNA guides cleavage, the cut may be between the nucleotides pairing to residues 10 and 11 of the miRNA. Alternatively, the miRNA may repress translation if the miRNA does not have the requisite degree of complementarity to the miRNA. Translational repression may be more prevalent in animals since animals may have a lower degree of complementarity.

It should be notes that there may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA* may also be due to mismatches in the stem structures of the pri-miRNA and pre-miRNA. The mismatches of the stem strands may lead to a population of different hairpin structures. Variability in the stem structures may also lead to variability in the products of cleavage by Drosha and Dicer.

3. Nucleic Acid

The present invention relates to an isolated nucleic acid comprising a nucleotide sequence referred to in SEQS: 1-4204915, the sequences referred to in Tables 1, 4, 10-14 and 21-23, and variants thereof. The variant may be a complement of the referenced nucleotide sequence. The variant may also be a nucleotide sequence that is substantially identical to the referenced nucleotide sequence or the complement thereof. The variant may also be a nucleotide sequence which hybridizes under stringent conditions to the referenced nucleotide sequence, complements thereof, or nucleotide sequences substantially identical thereto.

The nucleic acid may have a length of from 10 to 100 nucleotides. The nucleic acid may have a length of at least 10, 11, 12, 13, 14, 15, 16, 17, 18, 19, 20, 21, 22, 23, 24, 25, 26, 27, 28, 29, 30, 35, 40, 45, 50, 60, 70, 80 or 90 nucleotides. The nucleic acid may be synthesized or expressed in a cell (in vitro or in vivo) using a synthetic gene described below. The nucleic acid may be synthesized as a single strand molecule and hybridized to a substantially complementary nucleic acid to form a duplex, which is considered a nucleic acid of the invention. The nucleic acid may be introduced to a cell, tissue or organ in a single- or double-stranded form or capable of being expressed by a synthetic gene using methods well known to those skilled in the art, including as described in U.S. Pat. No. 6,506,559 which is incorporated by reference.

a. Pri-miRNA

The nucleic acid of the invention may comprise a sequence of a pri-miRNA or a variant thereof. The pri-miRNA sequence may comprise from 45-250, 55-200, 70-150 or 80-100 nucleotides. The sequence of the pri-miRNA may comprise a pre-miRNA, miRNA and miRNA* as set forth below. The pri-miRNA may also comprise a miRNA or miRNA* and the complement thereof, and variants thereof.

The pri-miRNA may comprise at least 19% adenosine nucleotides, at least 16% cytosine nucleotides, at least 23% thymine nucleotides and at least 19% guanine nucleotides.

The pri-miRNA may form a hairpin structure. The hairpin may comprise a first and second nucleic acid sequence that are substantially complementary. The first and second nucleic acid sequence may be from 37-50 nucleotides. The first and second nucleic acid sequence may be separated by a third sequence of from 8-12 nucleotides. The hairpin structure may have a free energy less than −25 Kcal/mole as calculated by the Vienna algorithm with default parameters, as described in Hofacker et al., Monatshefte f. Chemie 125: 167-188 (1994), the contents of which are incorporated herein. The hairpin may comprise a terminal loop of 4-20, 8-12 or 10 nucleotides.

The sequence of the pri-miRNA may comprise SEQS: 4097721-4204913, a precursor referred to in Table 1, the sequence of a sequence referred to in Tables 11-12 and 21-23, or a variant thereof.

b. Pre-miRNA

The nucleic acid of the invention may also comprise a sequence of a pre-miRNA or a variant thereof. The pre-miRNA sequence may comprise from 45-90, 60-80 or 60-70 nucleotides. The sequence of the pre-miRNA may comprise a miRNA and a miRNA* as set forth below. The pre-miRNA may also comprise a miRNA or miRNA* and the complement thereof, and variants thereof. The sequence of the pre-miRNA may also be that of a pri-miRNA excluding from 0-160 nucleotides from the 5' and 3' ends of the pri-miRNA.

The sequence of the pre-miRNA may comprise SEQS: 4097721-4204913, a precursor referred to in Table 1, the sequence of a sequence referred to in Tables 11-12 and 21-23, or a variant thereof.

c. MiRNA

The nucleic acid of the invention may also comprise a sequence of a miRNA, miRNA* or a variant thereof. The miRNA sequence may comprise from 13-33, 18-24 or 21-23 nucleotides. The sequence of the miRNA may be the first 13-33 nucleotides of the pre-miRNA. The sequence of the miRNA may be the last 13-33 nucleotides of the pre-miRNA.

The sequence of the miRNA may comprise SEQS: 1-1142416 or 4204914-4204915, a miRNA referred to in Table 1, the sequence of a sequence referred to in Tables 11-12 and 21-23, or a variant thereof.

d. Anti-miRNA

The nucleic acid of the invention may also comprise a sequence of an anti-miRNA that is capable of blocking the activity of a miRNA or miRNA*. The anti-miRNA may comprise a total of 5-100 or 10-60 nucleotides. The anti-miRNA may also comprise a total of at least 5, 6, 7, 8, 9, 10, 11, 12, 13, 14, 15, 16, 17, 18, 19, 20, 21, 22, 23, 24, 25 or 26 nucleotides. The sequence of the anti-miRNA may comprise (a) at least 5 nucleotides that are substantially identical to the 5' of a miRNA and at least 5-12 nucleotide that are substantially complementary to the flanking regions of the target site from the 5' end of said miRNA, or (b) at least 5-12 nucleotides that are substantially identical to the 3' of a miRNA and at least 5 nucleotide that are substantially complementary to the flanking region of the target site from the 3' end of said miRNA.

The sequence of the anti-miRNA may comprise the complement of SEQS: 1-1142416 or 4204914-4204915, a sequence of a miRNA referred to in Tables 1, 13-14 or 21-23, or a variant thereof.

e. Binding Site of Target

The nucleic acid of the invention may also comprise a sequence of a target miRNA binding site, or a variant thereof. The target site sequence may comprise a total of 5-100 or 10-60 nucleotides. The target site sequence may comprise at least 5 nucleotides of SEQS: 1142417-4097720, the sequence of a target gene binding site referred to in Tables 4, 10 or 15-16, or a variant thereof.

4. Synthetic Gene

The present invention also relates to a synthetic gene comprising a nucleic acid of the invention operably linked to a transcriptional and/or translational regulatory sequences. The synthetic gene may be capable of modifying the expression of a target gene with a binding site for the nucleic acid of the invention. Expression of the target gene may be modified in a cell, tissue or organ. The synthetic gene may be synthesized or derived from naturally-occurring genes by standard recombinant techniques. The synthetic gene may also comprise terminators at the 3'-end of the transcriptional unit of the synthetic gene sequence. The synthetic gene may also comprise a selectable marker.

5. Vector

The present invention also relates to a vector comprising a synthetic gene of the invention. The vector may be an expression vector. An expression vector may comprise additional elements. For example, the expression vector may have two replication systems allowing it to be maintained in two organisms, e.g., in mammalian or insect cells for expression and in a prokaryotic host for cloning and amplification. For integrating expression vectors, the expression vector may contain at least one sequence homologous to the host cell genome, and preferably two homologous sequences which flank the expression construct. The integrating vector may be directed to a specific locus in the host cell by selecting the appropriate homologous sequence for inclusion in the vector. The vector may also comprise a selectable marker gene to allow the selection of transformed host cells.

6. Host Cell

The present invention also relates to a host cell comprising a vector of the invention. The cell may be a bacterial, fungal, plant, insect or animal cell.

7. Probes

The present invention also relates to a probe comprising a nucleic acid of the invention. Probes may be used for screening and diagnostic methods, as outlined below. The probe may be attached or immobilized to a solid substrate, such as a biochip.

The probe may have a length of from 8 to 500, 10 to 100 or 20 to 60 nucleotides. The probe may also have a length of at least 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 220, 240, 260, 280 or 300 nucleotides. The probe may further comprise a linker sequence of from 10-60 nucleotides.

8. Biochip

The present invention also relates to a biochip. The biochip may comprise a solid substrate comprising an attached probe or plurality of probes of the invention. The probes may be capable of hybridizing to a target sequence under stringent hybridization conditions. The probes may be attached at spatially defined address on the substrate. More than one probe per target sequence may be used, with either overlapping probes or probes to different sections of a particular target sequence. The probes may be capable of hybridizing to target sequences associated with a single disorder.

The probes may be attached to the biochip in a wide variety of ways, as will be appreciated by those in the art. The probes may either be synthesized first, with subsequent attachment to the biochip, or may be directly synthesized on the biochip.

The solid substrate may be a material that may be modified to contain discrete individual sites appropriate for the attachment or association of the probes and is amenable to at least one detection method. Representative examples of substrates include glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses and plastics. The substrates may allow optical detection without appreciably fluorescing.

The substrate may be planar, although other configurations of substrates may be used as well. For example, probes may be placed on the inside surface of a tube, for flow-through sample analysis to minimize sample volume. Similarly, the substrate may be flexible, such as a flexible foam, including closed cell foams made of particular plastics.

The biochip and the probe may be derivatized with chemical functional groups for subsequent attachment of the two. For example, the biochip may be derivatized with a chemical functional group including, but not limited to, amino groups, carboxyl groups, oxo groups or thiol groups. Using these functional groups, the probes may be attached using functional groups on the probes either directly or indirectly using a linker. The probes may be attached to the solid support by either the 5' terminus, 3' terminus, or via an internal nucleotide.

The probe may also be attached to the solid support non-covalently. For example, biotinylated oligonucleotides can be made, which may bind to surfaces covalently coated with streptavidin, resulting in attachment. Alternatively, probes may be synthesized on the surface using techniques such as photopolymerization and photolithography.

9. MiRNA Expression Analysis

The present invention also relates to a method of identifying miRNAs that are associated with disease or a pathological condition, such as viral infection, comprising contacting a biological sample with a probe or biochip of the invention and detecting the amount of hybridization. PCR may be used to amplify nucleic acids in the sample, which may provide higher sensitivity.

The ability to identify miRNAs that are overexpressed or underexpressed in pathological cells compared to a control can provide high-resolution, high-sensitivity datasets which may be used in the areas of diagnostics, therapeutics, drug development, pharmacogenetics, biosensor development, and other related areas. An expression profile generated by the current methods may be a "fingerprint" of the state of the sample with respect to a number of miRNAs. While two states may have any particular miRNA similarly expressed, the evaluation of a number of miRNAs simultaneously allows the generation of a gene expression profile that is characteristic of the state of the cell. That is, normal tissue may be distinguished from diseased tissue. By comparing expression profiles of tissue in known different disease states, information regarding which miRNAs are associated in each of these states may be obtained. Then, diagnosis may be performed or confirmed to determine whether a tissue sample has the expression profile of normal or disease tissue. This may provide for molecular diagnosis of related conditions.

10. Determining Expression Levels

The present invention also relates to a method of determining the expression level of a disease-associated miRNA comprising contacting a biological sample with a probe or biochip of the invention and measuring the amount of hybridization.

The expression level of a disease-associated miRNA is information in a number of ways. For example, a differential expression of a disease-associated miRNA compared to a control may be used as a diagnostic that a patient suffers from the disease. Expression levels of a disease-associated miRNA may also be used to monitor the treatment and disease state of a patient. Furthermore, expression levels of a disease-associated miRNA may allow the screening of drug candidates for altering a particular expression profile or suppressing an expression profile associated with disease.

A target nucleic acid may be detected by contacting a sample comprising the target nucleic acid with a biochip comprising an attached probe sufficiently complementary to the target nucleic acid and detecting hybridization to the probe above control levels.

The target nucleic acid may also be detected by immobilizing the nucleic acid to be examined on a solid support such as nylon membranes and hybridizing a labeled probe with the sample. Similarly, the target nucleic may also be detected by immobilizing the labeled probe to the solid support and hybridizing a sample comprising a labeled target nucleic acid. Following washing to remove the non-specific hybridization, the label may be detected.

The target nucleic acid may also be detected in situ by contacting permeabilized cells or tissue samples with a labeled probe to allow hybridization with the target nucleic acid. Following washing to remove the non-specifically bound probe, the label may be detected.

These assays can be direct hybridization assays or can comprise sandwich assays, which include the use of multiple probes, as generally outlined in U.S. Pat. Nos. 5,681,702; 5,597,909; 5,545,730; 5,594,117; 5,591,584; 5,571,670; 5,580,731; 5,571,670; 5,591,584; 5,624,802; 5,635,352; 5,594,118; 5,359,100; 5,124,246; and 5,681,697, each of which is hereby incorporated by reference.

A variety of hybridization conditions may be used, including high, moderate and low stringency conditions as outlined above. The assays may be performed under stringency conditions which allow hybridization of the probe only to the target. Stringency can be controlled by altering a step parameter that is a thermodynamic variable, including, but not limited to, temperature, formamide concentration, salt concentration, chaotropic salt concentration pH, or organic solvent concentration.

Hybridization reactions may be accomplished in a variety of ways. Components of the reaction may be added simultaneously, or sequentially, in different orders. In addition, the reaction may include a variety of other reagents. These include salts, buffers, neutral proteins, e.g., albumin, detergents, etc. which may be used to facilitate optimal hybridization and detection, and/or reduce non-specific or background interactions. Reagents that otherwise improve the efficiency of the assay, such as protease inhibitors, nuclease inhibitors and anti-microbial agents may also be used as appropriate, depending on the sample preparation methods and purity of the target.

a. Diagnostic

The present invention also relates to a method of diagnosis comprising detecting a differential expression level of a disease- or infection-associated miRNA in a biological sample. The miRNA may be a viral miRNA, which may be expressed in the infected subject. The miRNA may also be from the subject, the expression level of which is modified due to a viral infection. The sample may be derived from a patient. Diagnosis of a disease state in a patient allows for prognosis and selection of therapeutic strategy. Further, the developmental stage of cells may be classified by determining temporarily expressed miRNA-molecules.

In situ hybridization of labeled probes to tissue arrays may be performed. When comparing the fingerprints between an individual and a standard, the skilled artisan can make a diagnosis, a prognosis, or a prediction based on the findings. It is further understood that the genes which indicate the diagnosis may differ from those which indicate the prognosis and molecular profiling of the condition of the cells may lead to distinctions between responsive or refractory conditions or may be predictive of outcomes.

b. Drug Screening

The present invention also relates to a method of screening therapeutics comprising contacting a pathological cell capable of expressing a disease related miRNA with a candidate therapeutic and evaluating the effect of a drug candidate on the expression profile of the disease associated miRNA. Having identified the differentially expressed miRNAs, a variety of assays may be executed. Test compounds may be screened for the ability to modulate gene expression of the disease associated miRNA. Modulation includes both an increase and a decrease in gene expression.

The test compound or drug candidate may be any molecule, e.g., protein, oligopeptide, small organic molecule, polysaccharide, polynucleotide, etc., to be tested for the capacity to directly or indirectly alter the disease phenotype or the expression of the disease associated miRNA. Drug candidates encompass numerous chemical classes, such as small organic molecules having a molecular weight of more than 100 and less than about 500, 1,000, 1,500, 2,000 or 2,500 daltons. Candidate compounds may comprise functional groups necessary for structural interaction with proteins, particularly hydrogen bonding, and typically include at least an amine, carbonyl, hydroxyl or carboxyl group, preferably at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Combinatorial libraries of potential modulators may be screened for the ability to bind to the disease associated miRNA or to modulate the activity thereof. The combinatorial library may be a collection of diverse chemical compounds generated by either chemical synthesis or biological synthesis by combining a number of chemical building blocks such as reagents. Preparation and screening of combinatorial chemical libraries is well known to those of skill in the art. Such combinatorial chemical libraries include, but are not limited to, peptide libraries encoded peptides, benzodiazepines, diversomers such as hydantoins, benzodiazepines and dipeptide, vinylogous polypeptides, analogous organic syntheses of small compound libraries, oligocarbamates, and/or peptidyl phosphonates, nucleic acid libraries, peptide nucleic acid libraries, antibody libraries, carbohydrate libraries, and small organic molecule libraries.

11. Gene Silencing

The present invention also relates to a method of using the nucleic acids of the invention to reduce expression of a target gene in a cell, tissue or organ. Expression of the target gene may be reduced by expressing a nucleic acid of the invention that comprises a sequence substantially complementary to one or more binding sites of the target miRNA. The nucleic acid may be a miRNA or a variant thereof. The nucleic acid may also be pri-miRNA, pre-miRNA, or a variant thereof, which may be processed to yield a miRNA. The expressed miRNA may hybridize to a substantially complementary binding site on the target miRNA, which may lead to activation of RISC-mediated gene silencing. An example for a study employing over-expression of miRNA is Yekta et al 2004, Science 304-594, which is incorporated herein by reference. One of ordinary skill in the art will recognize that the nucleic acids of the present invention may be used to inhibit expression of target genes using antisense methods well known in the art, as well as RNAi methods described in U.S. Pat. Nos. 6,506,559 and 6,573,099, which are incorporated by reference.

The target gene may be a viral gene, which may be reduced by expressing a viral or human miRNA. The target gene may also be a human gene that is expressed upon viral infection, which may be reduced by expressing a viral or human miRNA. The target of gene silencing may be a protein that causes the silencing of a second protein. By repressing expression of the target gene, expression of the second protein may be increased. Examples for efficient suppression of miRNA expression are the studies by Esau et al 2004 JBC 275-52361; and Cheng et al 2005 Nucleic Acids Res. 33-1290, which is incorporated herein by reference.

12. Gene Enhancement

The present invention also relates to a method of using the nucleic acids of the invention to increase expression of a target gene in a cell, tissue or organ. Expression of the target gene may be increased by expressing a nucleic acid of the invention that comprises a sequence substantially complementary to a pri-miRNA, pre-miRNA, miRNA or a variant thereof. The nucleic acid may be an anti-miRNA. The anti-miRNA may hybridize with a pri-miRNA, pre-miRNA or miRNA, thereby reducing its gene repression activity. Expression of the target gene may also be increased by expressing a nucleic acid of the invention that is substantially complementary to a portion of the binding site in the target gene, such that binding of the nucleic acid to the binding site may prevent miRNA binding.

The target gene may be a viral gene, expression of which may reduce infectivity of the virus. The target gene may also be a human gene, expression of which may reduce infectivity of the virus or increase resistance or immunity to the viral infection.

13. Therapeutic

The present invention also relates to a method of using the nucleic acids of the invention as modulators or targets of disease or disorders, such as those associated with viral infection. In general, the claimed nucleic acid molecules may be used as a modulator of the expression of genes which are at least partially complementary to said nucleic acid. Further, miRNA molecules may act as target for therapeutic screening procedures, e.g. inhibition or activation of miRNA molecules might modulate a cellular differentiation process, e.g. apoptosis.

Furthermore, existing miRNA molecules may be used as starting materials for the manufacture of sequence-modified miRNA molecules, in order to modify the target-specificity thereof, e.g. an oncogene, a multidrug-resistance gene or another therapeutic target gene. Further, miRNA molecules can be modified, in order that they are processed and then generated as double-stranded siRNAs which are again directed against therapeutically relevant targets. Furthermore, miRNA molecules may be used for tissue reprogramming procedures, e.g. a differentiated cell line might be transformed by expression of miRNA molecules into a different cell type or a stem cell.

14. Compositions

The present invention also relates to a pharmaceutical composition comprising the nucleic acids of the invention and optionally a pharmaceutically acceptable carrier. The compositions may be used for diagnostic or therapeutic applications. The administration of the pharmaceutical composition may be carried out by known methods, wherein a nucleic acid is introduced into a desired target cell in vitro or in vivo. Commonly used gene transfer techniques include calcium phosphate, DEAE-dextran, electroporation, microinjection, viral methods and cationic liposomes.

15. Kits

The present invention also relates to kits comprising a nucleic acid of the invention together with any or all of the following: assay reagents, buffers, probes and/or primers, and sterile saline or another pharmaceutically acceptable emulsion and suspension base. In addition, the kits may include instructional materials containing directions (e.g., protocols) for the practice of the methods of this invention.

EXAMPLE 1

Prediction of miRNAs

We surveyed a number of viral genomes for potential miRNA coding genes using three computational approaches similar to those described in U.S. patent application Ser. Nos. 60/522,459, 10/709,577 and 10/709,572, the contents of which are incorporated herein by reference, for predicting miRNAs. The predicted hairpins and potential miRNAs were scored by thermodynamic stability, as well as structural and contextual features. The algorithm was calibrated by using miRNAs in the Sanger Database which had been validated.

1. First and Second Screen

Tables 11 and 12 show the sequence ("PRECURSOR SEQUENCE"), sequence identifier ("PRECUR SEQ-ID") and organism of origin ("GAM ORGANISM") for each predicted hairpin from the first computational screen, together with the predicted miRNAs ("GAM NAME"). Tables 13 and 14 show the sequence ("GAM RNA SEQUENCE") and sequence identifier ("GAM SEQ-ID") for each miRNA ("GAM NAME"), along with the organism of origin ("GAM ORGANISM") and Dicer cut location ("GAM POS").

2. Third Screen

Table 1 lists the SEQ ID NO for each predicted hairpin ("HID") of the third computational screen of a particular viral genome ("V"; See also Table 10). Table 1 also lists the genomic location for each hairpin ("Hairpin Location"). The format for the genomic location is a concatenation of <strand><start position>. The genetic location is based on the NCBI-Entrez Nucleotides database. The Entrez Nucleotides database is a collection of sequences from several sources, including GenBank, RefSeq, and PDB. Table 10 shows the accession number and the build (version) are presented for each of the genomes used in this screen.

Table 1 also lists the SEQ ID NO ("MID") for each predicted miRNA and miRNA*. Table 1 also lists the prediction score grade for each hairpin ("P") on a scale of 0-1 (1 the hairpin is the most reliable), as described in Hofacker et al., Monatshefte f. Chemie 125: 167-188, 1994. Table 1 also lists the p-value ("Pval") calculated out of background hairpins for the values of each P scores. All the p-values are significantlower than 0.05. As shown in Table 1, there are few instances where the Pval is 0.0. In each of these cases, the value is less than 0.0001. The p-values were calculated by comparing the palgrade of the tested hairpin to the palgrade of other sequences without pre-selection of hairpins.

Table 1 also lists whether the miRNAs were validated by expression analysis ("E") (Y=Yes, N=No), as detailed in Table 2. Table 1 also lists whether the miRNAs were validated by sequencing ("S") (Y=Yes, N=No), as detailed in Table 3. If there was a difference in sequences between the predicted and sequenced miRNAs, the sequenced sequence is presented. It should be noted that failure to sequence or detect expression of a miRNA does not necessarily mean that a miRNA does not exist. Such undetected miRNAs may be expressed in tissues other than those tested. In addition, such undetected miRNAs may be expressed in the test tissues, but at a difference stage or under different condition than those of the experimental cells.

Table 1 also listed whether the miRNAs were shown to be differentially expressed ("D") (Y=Yes, N=No) in at least one disease, as detailed in Table 2). Table 1 also whether the miRNAs were present ("F") (Y=Yes, N=No) in Sanger DB Release 6.0 (April 2005) as being detected in humans or mice predicted in humans. As discussed above, the miRNAs listed in the Sanger database are a component of the prediction algorithm and a control for the output.

Table 1 also lists a genetic location cluster ("LC") for those hairpins that are within 1,000 nucleotides of each other of a particular virus. Each miRNA that has the same LC share the same genetic cluster. Those hairpins that overlap are not clustered. Table 1 also lists a seed cluster ("SC") to group miRNAs by their seed of 2-7 by an exact match, regardless of the source virus. Each miRNA that has the same SC have the same seed. For a discussion of seed lengths of 6 nucleotides, see Lewis et al., Cell, 120; 15-20 (2005).

EXAMPLE 2

Prediction of Target Genes

The predicted miRNAs from the three computational screens of Example 1 were then used to predict human and viral target genes and their binding sites using two computational approaches similar to those described in U.S. patent application Ser. Nos. 60/522,459, 10/709,577 and 10/709,572, the contents of which are incorporated herein by reference, for predicting miRNAs.

1. First and Second Screen

Tables 15 and 16 list the predicted target genes ("TARGET") and binding site sequence ("TARGET BINDING SITE SEQUENCE") and binding site sequence identifier ("TARGET BINDING SITE SEQ-ID") from the first computational screen, as well as the organism of origin for the target ("TARGET ORGANISM").

2. Third Screen a. Human Target Genes

Table 4 lists the predicted human target gene for each miRNA (MID) from a particular virus (V) and its hairpin (HID) from the third computational screen. The names of the target genes were taken from NCBI Reference Sequence release 9 (Pruitt et al., Nucleic Acids Res, 33(1):D501-D504, 2005; Pruitt et al., Trends Genet., 16(1):44-47, 2000; and Tatusova et al., Bioinformatics, 15(7-8):536-43, 1999). Target genes were identified by having a perfect complementary match of a 7 nucleotide miRNA seed (positions 2-8) and an A on the UTR (total=8 nucleotides). For a discussion on identifying target genes, see Lewis et al., Cell, 120: 15-20, (2005). For a discussion of the seed being sufficient for binding of a miRNA to a UTR, see Lim Lau et al., (Nature 2005) and Brenneck et al, (PLoS Biol 2005).

The binding site screen only considered the first 4000 nucleotides per UTR and considered the longest transcript when there were several transcripts per gene. The filtering reduced the total number of transcripts from 23626 to 14239. Table 4 lists the SEQ ID NO for the predicted binding sites for each target gene. The sequence of the binding site includes the 20 nucleotides 5' and 3' of the binding site as they are located on the spliced miRNA. In cases that the binding site is comprised from 2 exons, 20 nucleotides are included from both 5' and 3' ends of both exons.

Table 5 shows the relationship between the miRNAs ("MID")/hairpins ("HID") of a particular virus ("V") and diseases by their human target genes. The name of the diseases are taken from OMIM. For a discussion of the rationale for connecting the host gene the hairpin is located upon to disease, see Baskerville and Bartel, RNA, 11: 241-247 (2005) and Rodriguez et al., Genome Res., 14: 1902-1910 (2004). Table 5 shows the number of miRNA target genes ("N") that are related to the disease. Table 5 also shows the total number of genes that are related to the disease ("T"), which is taken from the genes that were predicted to have binding sites for miRNAs. Table 5 also shows the percentage of N out of T and the p-value of hypergeometric analysis ("Pval"). In cases that the pval is listed as 0.0, it means that the value is less than 0.0001. For a reference of hypergeometric analysis, see Schaum's Outline of Elements of Statistics II: Inferential Statistics. Table 7 shows the disease codes for Tables 5 and 6.

b. Viral Target Genes

Similar to the date described above in Table 4 for human target genes, Table 10 lists the predicted viral target gene for each miRNA (MID) from the same particular virus (V) and its hairpin (HID) from the third computational screen. The prediction of viral binding sites used complete genes not UTRs as in the Table 4 in the method described above for human target genes Table 10. Candidate target genes were included in the screen if they were known to have a role in the virus life cycle. Those miRNAs that have binding sites on a viral gene that takes part in the virus life cycle they may affect the diseases that may be related to the virus Human Herpes virus 1 and 2 are related to any of several inflammatory diseases caused by a herpesvirus and marked in one case by groups of watery blisters on the skin or mucous membranes (as of the mouth and lips) above the waist and in the other by such blisters on the genitals. Human herpesvirus 4 (Epstein-Barr virus) causes infectious mononucleosis and is associated with Burkitt's lymphoma and nasopharyngeal carcinoma. HIV strains are related to Acquired Immune Deficiency Syndrome (AIDS). Hepatitis B and C viruses cause inflammation of the liver.

EXAMPLE 3

Validation of miRNAs

To confirm the hairpins and miRNAs predicted in Example 1, we detected expression in various tissues using the high-throughput microarrays similar to those described in U.S. patent application Ser. Nos. 60/522,459, 10/709,577 and 10/709,572, the contents of which are incorporated herein by reference. For each predicted precursor miRNA, mature miRNAs derived from both stems of the hairpin were tested.

1. Expression Analysis—Set 1 and Set 2

Tables 17-19 list the results of microarray expression analysis to detch miRNA sequence ("GAM RNA SEQUENCE").

2. Expression Analysis—Set 3

Table 2 shows the hairpins ("HID") of the third prediction set that were validated by detecting expression of related miRNAs ("MID") from a particular virus ("V"), as well as a code for the tissue ("Tissue") that expression was detected. In cases where there is more than one score from the same miRNA in the same tissue, only the one with the higher score is presented.

The tissue and diseases codes are listed in Table 6 and Table 7, respectively. Table 8 shows the relationship between gene and disease. This enables the connection of all miRNAs to disease. Table 4 assign at least one target gene to each miRNA. Table 5 presents the outcome of statistical analysis of table 4 and OMIM to depict significant relations of miRNAs and disease. Table 8 is basically a condensed version of OMIM. It lists for each gene all the numeric codes of the diseases that are related to it.

All the tissues disclosed give an indication of a viral disease. The fact that significant expression of the virus was measured implies that in this tissue it may be involve in a viral disease(s). E.g. when a mir from HIV was expressed in T cell line it may have an effect on AIDS. Of course cell lines represent only subset of the features of a tissue as it function in an organ however we can deduce from the expression as it is measured in the cell line.

Table 2 also shows the chip expression score grade (range of 500-65000)("S"). A threshold of 500 was used to eliminate non-significant signals and the score was normalized by Mir-Chip probe signals from different experiments. Variations in the intensities of fluorescence material between experiments may be due to variability in RNA preparation or labeling efficiency. We normalized based on the assumption that the total amount of miRNAs in each sample is relatively constant. First we subtracted the background signal from the raw signal of each probe, where the background signal is defined as 400. Next, we divided each miRNA probe signal by the average signal of all miRNAs, multiplied the result by 10000 and added back the background signal of 400. Thus, by definition, the sum of all miRNA probe signals in each experiment is 10400.

Table 2 also shows a statistical analysis of the normalized signal ("Spval") calculated on the normalized score. For each miRNA, we used a relevant control group out of the full predicted miRNA list. Each miRNA has an internal control of probes with mismatches. The relevant control group contained probes with similar C and G percentage (abs diff <5%) in order to have similar Tm. The probe signal P value is the ratio over the relevant control group probes with the same or higher signals. The results are p-value $\leq 0.05$ and score is above 500. In those cases that the SPVal is listed as 0.0, the value is less than 0.0001.

3. Sequencing—Set 3

To further validate the hairpins ("HID") of the second prediction, a number of miRNAs were validated by sequencing methods similar to those described in U.S. patent application Ser. Nos. 60/522,459, 10/709,577 and 10/709,572, the contents of which are incorporated herein by reference. Table 3 shows the hairpins ("HID") that were validated by sequencing a miRNA (MID") from a virus ("V") in the indicated tissue ("Tissue").

4. Northern Analysis

Figure 3:
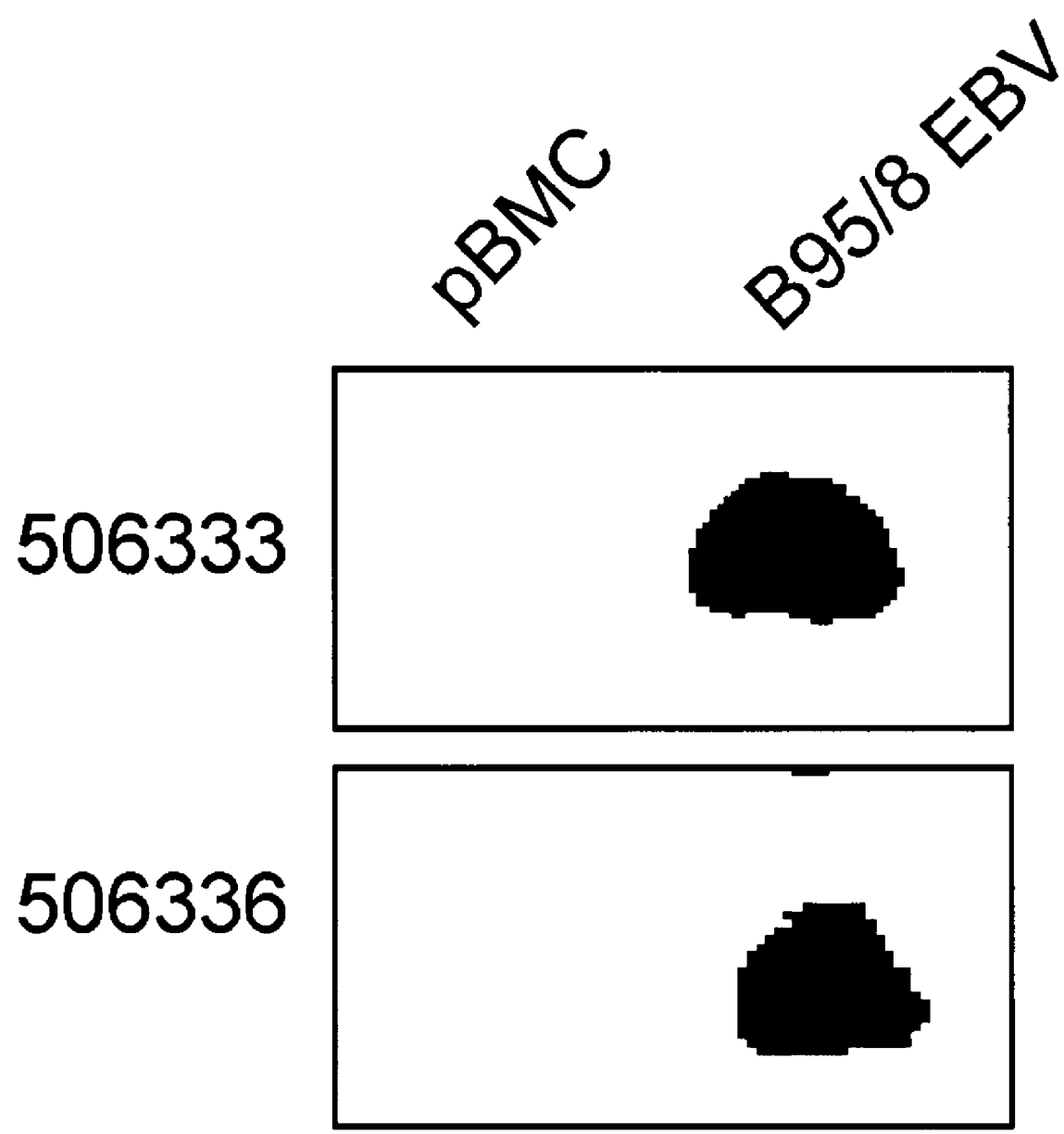

A group of miRNA were validated by Northern analysis, as shown in FIGS. 2 and 3.

EXAMPLE 4

Differential Expression of miRNAs

1. Viral miRNAs

Table 20 provides validated viral miRNAs that were demonstrated to be differentially expressed in diseased compared to healthy human tissue or human-derived cell lines. All miRNA sequences were validated using a miRNA microarray as described hereinabove. For Alzheimer Disease, GAM RNA expression was studied in a mixture of tissue from diseased and healthy human amygdala, cingulate cortex, caudate nucleus, globus pallidus, posterior parietal cortex, and superior parietal cortex, all brain regions that were shown to be affected mildly, moderately, or severely by Alzheimer pathology. For Parkinson Disease, GAM RNA expression was studied in substantia nigra tissue from diseased and healthy human tissue. MT2 cell lines were infected with a T-tropic clinical isolation of Clade A Human Immunodeficiency Virus (HIV), while healthy controls were not infected. cMagi cell lines were infected with a M-tropic Clade B HIV, while healthy controls were not infected. Human fibroblast cells (TC) were infected with HSV1 or HSV2 or were not infected and served as controls. GAM RNA SEQUENCE: the sequence (5' to 3') of the mature, "diced" GAM RNA. CHIP SEQUENCE is the sequence of the oligonucleotide including the predicted GAM RNA that was placed on the microarray (not including the non-genomic sequence used as a separator from the microarray surface). DISEASE: the disease in which the GAM RNA was differentially expressed—BAL refers to M-tropic HIV1 Subtype B, lab strain, and BLAI refers to T-tropic HIV-1 (LAV-1), Subtype B; SIGNAL (HEALTHY): the signal on the microarray for the GAM RNA in samples comprised of human tissue or human-derived cell lines that are not afflicted with the specified disease; SIGNAL (DISEASE): the signal on the microarray for the GAM RNA in samples comprised of human tissue or human-derived cell lines that are afflicted with the specified disease.

2. Human miRNAs

Table 21 lists expression data of miRNAs by the following: HID: hairpin SEQ; MID: miRNA SEQ; Tissue: tested tissue; S: chip expression score grade (range=100-65000); Dis. Diff. Exp.: disease related differential expression and the tissue it was tested in; R: ratio of disease related expression (range=0.01-99.99); and abbreviations: Brain Mix A—a mixture of brain tissue that are affected in Alzheimer; Brain Mix B—a mixture of all brain tissues; and Brain SN—Substantia Nigra. Tables 22 and 23 provide the details regarding the differentially expressed miRNAs by the following: HID: hairpin SEQ; Hairpin_Loc: hairpin genomic hocation, concatenating <chr_id><strand>space<start position> (e.g., 19+135460000 means chr19+strand, start position 135460000); C: conservation in evolution (Yes/No and "-" when data is not available; Yes-conservation level above threshold of 0.7); T: genomic type, InterGenic (G), Intron (I), Exon (E); MID: miRNA SEQ; Target Gene, Disease: target gene (HUGO database) and related disease (OMIM database); P: prediction score grade, on range 0-9; E: chip expression information—Yes/No (Y/N); S: validation by eequencing—Yes/No (Y/N); HID: hairpin SEQ. Table 24 provides the sequence for the sequences referred to in Tables 21-23.

EXAMPLE 4

Analysis of EBV miRNAs

1. Validation of Expression

Figure 4:
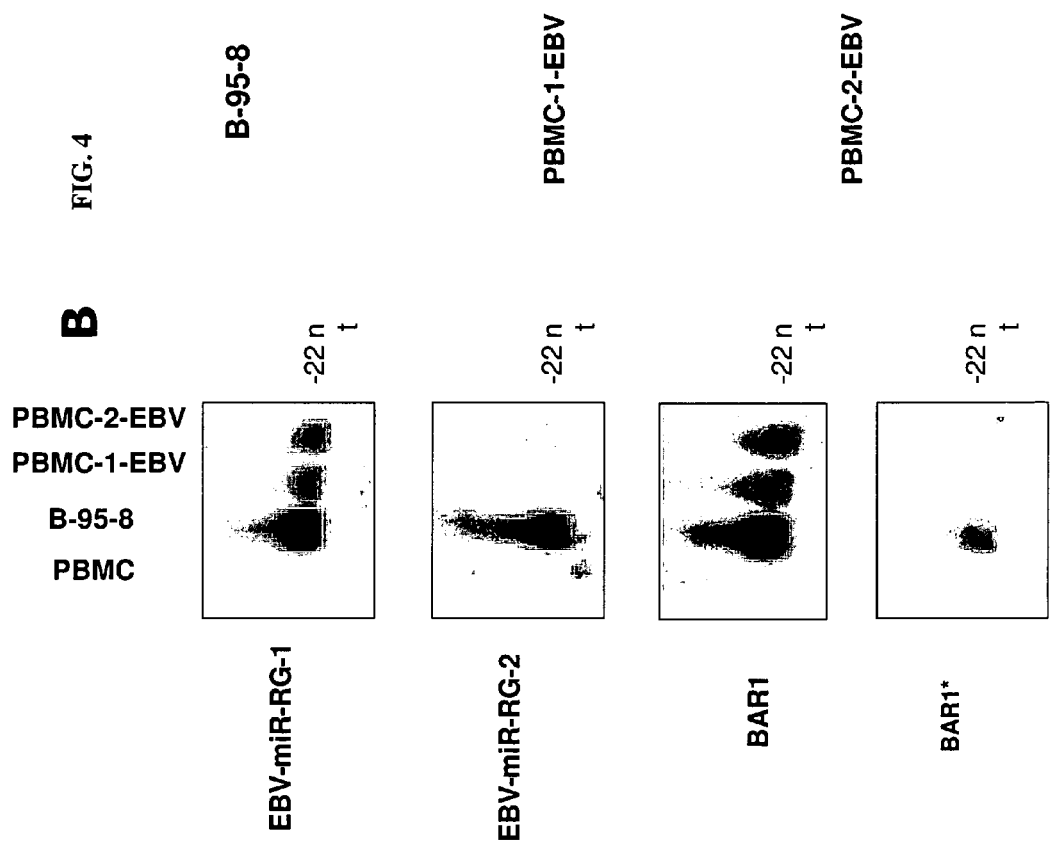
FIG. 4 shows validation of miRNAs expressed by EBV.

FIG. 4 shows the validation of expression of miRNAs predicted in EBV (Epstein's Barr Virus) miRNAs; expression validation. Three cell line were tested. Two were freshly infected normal B-cells (PBMC-1/2-EBV), and one EBV-transformed cell line (B-95-8). The 3 cell lines exhibit the same extent of EBV infection (FIG. 4A). However, in contrast to the freshly infected B cells, EBV-miR-RG-1 and -2 are highly expressed in the B-95-8 cell-line (FIG. 4B).

2. Knockout of Expression

Figure 5:
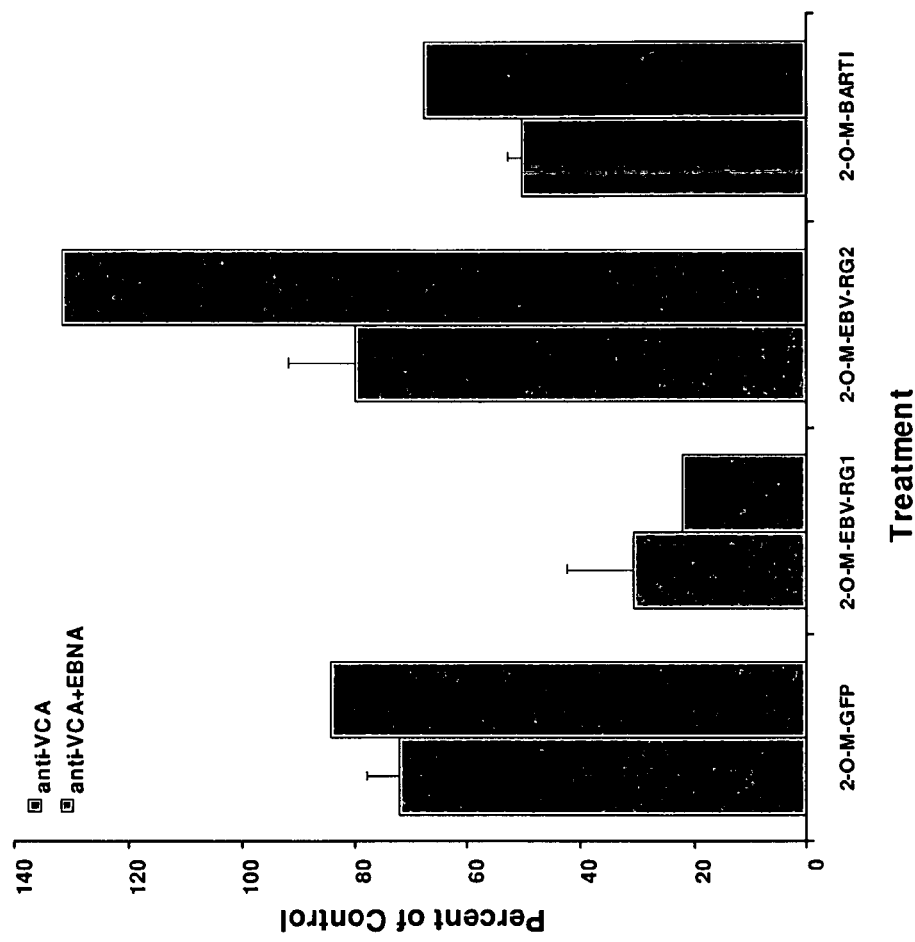
FIG. 5 shows the knockout of EBV miRNAs.

FIG. 5 shows the knockout of EBV miRNAs. Addition of 2-O-Methyl against EBV-miR-RG-1 to B-95-8 cell line resulted is dramatic reduction of cells expressing EBV antigens. Addition of 2-O-Methyl against EBV-miR-RG-2 to B-95-8, had a moderate effect, slightly increasing EBV expression.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07795419B2). An electronic copy of the "Sequence Listing" will also be available from the USPTO upon request and payment of the fee set forth in 37 CFR 1.19(b)(3).

The invention claimed is:

1. An isolated nucleic acid, wherein the sequence of the nucleic acid is selected from the group consisting of:
   (a) SEQ ID NO: 906;
   (b) a DNA encoding (a), wherein the DNA is identical in length to (a);
   (c) a sequence at least 80% identical to (a) or (b), wherein the identity is over the length of (a) and the sequence is 70-150 nucleotides in length; and
   (d) the complement of any one of (a)-(c), wherein the complement is identical in length to (a).

2. An isolated nucleic acid, wherein the sequence of the nucleic acid is selected from the group consisting of:
   (a) SEQ ID NO: 3107;
   (b) a DNA encoding (a), wherein the DNA is identical in length to (a);
   (c) a sequence at least 80% identical to (a) or (b), wherein the identity is over the length of (a) and the sequence is 18-24 nucleotides in length;
   (d) the complement of any one of (a)-(c), wherein the complement is identical in length to (a).

* * * * *